US009376720B2

(12) United States Patent
Wirtz

(10) Patent No.: US 9,376,720 B2
(45) Date of Patent: Jun. 28, 2016

(54) METHOD TO ASSESS PROGNOSIS AND TO PREDICT THERAPEUTIC SUCCESS IN CANCER BY DETERMINING HORMONE RECEPTOR EXPRESSION LEVELS

(76) Inventor: Ralph Wirtz, Cologne (DE)

( * ) Notice: Subject to any disclaimer, the term of this patent is extended or adjusted under 35 U.S.C. 154(b) by 0 days.

(21) Appl. No.: 13/284,759

(22) Filed: Oct. 28, 2011

(65) Prior Publication Data

US 2012/0157542 A1 Jun. 21, 2012

Related U.S. Application Data

(63) Continuation of application No. PCT/EP2010/055745, filed on Apr. 28, 2010.

(30) Foreign Application Priority Data

Apr. 29, 2009 (EP) .................................... 09159005

(51) Int. Cl.
*C12Q 1/68* (2006.01)

(52) U.S. Cl.
CPC ............ *C12Q 1/6886* (2013.01); *C12Q 1/6809* (2013.01); *C12Q 2600/118* (2013.01)

(58) Field of Classification Search
CPC ............... C12Q 1/6886; C12Q 1/6809; C12Q 2600/118
See application file for complete search history.

(56) References Cited

U.S. PATENT DOCUMENTS

| | | | | |
|---|---|---|---|---|
| 2005/0266561 | A1* | 12/2005 | Wells | 435/455 |
| 2007/0275398 | A1* | 11/2007 | Kiefer et al. | 435/6 |
| 2009/0023137 | A1* | 1/2009 | Van Der Zee et al. | 435/6 |
| 2009/0075257 | A1* | 3/2009 | Pollock et al. | 435/6 |
| 2010/0266540 | A1* | 10/2010 | Craven | 424/85.4 |
| 2012/0129262 | A1* | 5/2012 | West et al. | 435/455 |

FOREIGN PATENT DOCUMENTS

| | | |
|---|---|---|
| WO | 2006/052731 | 5/2006 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Zhang et al, Chin. J. Clin. Oncol. 5: 418 (2008).*
Watson, Molecular Biology of the Gene, 3rd edition, (1976), W.A. Benjamin, Inc., Menlo Park, CA, pp. 281-282.*
Fujimoto, J. et al.: "Clinical significance of expression of estrogen receptor alpha and beta mRNAs in ovarian cancers" *Oncology* 58(4): 334-341 (2000).
Kawai, H., et al.: "Estrogen receptor alpha and beta are prognostic factors in non-small cell lung cancer" *Clinical Cancer Research* 11(14): 5084-5089 (2005).
Lee, E.S., et al.: "Prediction of Recurrence-free survival in postoperative non-small cell lung cancer patients by using an integrated model of clinical and gene expression" *Clin Cancer Res* 14(22): 7397-7404 (2008).
Nose, N., et al.: "Association between estrogen receptor-beta expression and epidermal growth factor receptor mutation in the postoperative prognosis of adenocarcinoma of the lung" *Journal of Clinical Oncology* 27(3): 411-417 (2009).
Paik S., et al.:"A Multigene Assay to Predict Recurrence of Tamoxifen-treated, Node-Negative Breast Cancer" *New England Journal of Medicine*, 351(27); 2817-2826 (2004).
Poola, I., et al.: "Quantitation of estrogen receptor mRNA copy numbers in breast cancer call lines and tumors" *Analytical Biochemistry* 258(2): 209-215 (1998).
EP Examination Report in corresponding European Application No. 10721373.8, pp: 1-5 (Jan. 21, 2013).

* cited by examiner

*Primary Examiner* — James Martinell
(74) *Attorney, Agent, or Firm* — David G. Rosenbaum; J. Peter Paredes; Rosenbaum IP, P.C.

(57) ABSTRACT

The present invention is related to a method of classifying a sample of a patient who suffers from or being at risk of developing cancer, said method comprising the steps of determining in said sample from said patient, on a non protein basis, the expression level of at least one gene encoding for a hormone receptor selected from the group comprising estrogen receptor, progesterone receptor and/or androgen receptor in said sample; comparing the one or more expression level(s) determined with one or more expression level(s) of one or more reference genes, and classifying the sample of said patient from the outcome of the comparison into one of at least two classifications.

17 Claims, 20 Drawing Sheets

| | | | |
|---|---|---|---|
| ESR1 > Median | Liver Metastasis | 0,2381 | 0,1894 |
| ESR1 > Median | Brain Metastasis | -0,0727 | 0,6924 |
| ESR1 > Median | Bone Metastasis | 0,4476 | 0,0102 |
| ESR1 > Median | Lung Metastasis | 0,1260 | 0,4920 |
| ESR1 > Median | Pleural Metastasis | 0,0605 | 0,7421 |
| ESR1 > Median | Adrenal Metastasis | 0,2952 | 0,1009 |

| Variable | by Variable | Spearman Rhc | Prob>\|Rho |
|---|---|---|---|
| CDH11 | SNAI2 | 0,6651 | <.0001 |
| CDH1 | ESR1 | 0,4497 | 0,0059 |
| CDH11 | CDH1 | -0,2891 | 0,0873 |
| SNAI2 | CDH1 | -0,3586 | 0,0318 |
| CDH11 | ESR1 | -0,4368 | 0,0077 |
| SNAI2 | ESR1 | -0,5570 | 0,0004 |

FIGURE 8

SEQ ID No 1

ESR1 Estrogen receptor 1

NM_000125.2

Hs.208124 gagttgtgcctggagtgatgtttaagccaatgtcagggcaaggcaacagtccctggccgtcctccagcacctttg
taatgcatatgagctcgggagaccagtacttaaagttggaggcccgggagcccaggagctggcggagggcgttcg
tcctgggactgcacttgctcccgtcgggtcgcccggcttcaccggacccgcaggctcccggggcagggccggggc
cagagctcgcgtgtcggcgggacatgcgctgcgtcgcctctaacctcgggctgtgctctttttccaggtggcccg
ccggtttctgagccttctgccctgcggggacacggtctgcaccctgcccgcggccacggaccatgaccatgaccc
tccacaccaaagcatccgggatggccctactgcatcagatccaagggaacgagctggagcccctgaaccgtccgc
agctcaagatccccctggagcggcccctgggcgaggtgtacctggacagcagcaagcccgccgtgtacaactacc
ccgagggcgccgcctacgagttcaacgccgcggccgccgccaacgcgcaggtctacggtcagaccggcctcccct
acggcccgggtctgaggctgcggcgttcggctccaacggcctggggggtttcccccactcaacagcgtgtctc
cgagcccgctgatgctactgcacccgccgccgcagctgtcgcctttcctgcagccccacggccagcaggtgccct
actacctggagaacgagcccagcggctacacggtgcgcgaggccggcccgccggcattctacaggccaaattcag
ataatcgacgccagggtggcagagaaagattggccagtaccaatgacaagggaagtatggctatggaatctgcca
aggagactcgctactgtgcagtgtgcaatgactatgcttcaggctaccattatggagtctggtcctgtgagggct
gcaaggccttcttcaagagaagtattcaaggacataacgactatatgtgtccagccaccaaccagtgcaccattg
ataaaaacaggaggaagagctgccaggcctgccggctccgcaaatgctacgaagtgggaatgatgaaaggtggga
tacgaaaagaccgaagaggagggagaatgttgaaacacaagcgccagagagatgatggggagggcaggggtgaag
tggggtctgctggagacatgagagctgccaacctttggccaagcccgctcatgatcaaacgctctaagaagaaca
gcctggccttgtccctgacggccgaccagatggtcagtgccttgttggatgctgagccccccatactctattccg
agtatgatcctaccagacccttcagtgaagcttcgatgatgggcttactgaccaacctggcagacagggagctgg
ttcacatgatcaactgggcgaagagggtgccaggctttgtggatttgaccctccatgatcaggtccaccttctag
aatgtgcctggctagagatcctgatgattggtctcgtctggcgctccatggagcacccagggaagctactgtttg
ctcctaacttgctcttggacaggaaccagggaaaatgtgtagagggcatggtggagatcttcgacatgctgctgg
ctacatcatctcggttccgcatgatgaatctgcagggagaggagtttgtgtgcctcaaatctattatttgctta
attctggagtgtacacatttctgtccagcaccctgaagtctctggaagagaaggaccatatccaccgagtcctgg
acaagatcacagacactttgatccacctgatggccaaggcaggcctgaccctgcagcagcagcaccagcggctgg
cccagctcctcctcatcctctcccacatcaggcacatgagtaacaaaggcatggagcatctgtacagcatgaagt
gcaagaacgtggtgcccctctatgacctgctgctggagatgctggacgcccaccgcctacatgcgcccactagcc
gtggaggggcatccgtggaggagacggaccaaagccacttggccactgcgggctctacttcatcgcattccttgc
aaaagtattacatcacggggggaggcagagggtttccctgccacggtctgagagctccctggctcccacacggttc
agataatccctgctgcattttaccctcatcatgcaccactttagccaaattctgtctcctgcatacactccggca
tgcatccaacaccaatggctttctagatgagtggccattcatttgcttgctcagttcttagtggcacatcttctg
tcttctgttgggaacagccaaagggattccaaggctaaatctttgtaacagctctctttcccccttgctatgtta
ctaagcgtgaggattcccgtagctcttcacagctgaactcagtctatgggttggggctcagataactctgtgcat
ttaagctacttgtagagacccaggcctggagagtagacattttgccctctgataagcactttttaaatggctctaa
gaataagccacagcaaagaatttaaagtggctcctttaattggtgacttggagaaagctaggtcaagggtttatt
atagcaccctcttgtattcctatggcaatgcatccttttatgaaagtggtacaccttaaagcttttatatgactg
tagcagagtatctggtgattgtcaattcattccccctataggaatacaaggggcacacagggaaggcagatcccc
tagttggcaagactattttaacttgatacactgcagattcagatgtgctgaaagctctgcctctggctttccggt
catgggttccagttaattcatgcctcccatggacctatggagagcagcaagttgatcttagttaagtctccctat
atgagggataagttcctgatttttgtttttatttttgtgttacaaaagaaagccctccctccctgaacttgcagt
aaggtcagcttcaggacctgtttccagtgggcactgtacttggatcttcccggcgtgtgtgtgccttacacagggg tgaactgttcactgtggtgatgcatgatgagggtaaatggtagttgaaaggagcaggggccctggtgttgcattt
agccctggggcatggagctgaacagtacttgtgcaggattgttgtggctactagagaacaagagggaaagtaggg
cagaaactggatacagttctgaggcacagccagacttgctcagggtggccctgccacaggctgcagctacctagg
aacattccttgcagaccccgcattgccctttggggtgccctgggatccctggggtagtccagctcttcttcatt
tcccagcgtggccctggttggaagaagcagctgtcacagctgctgtagacagctgtgttcctacaattggcccag
caccctggggcacgggagaagggtggggaccgttgctgtcactactcaggctgactggggcctggtcagattacg
tatgcccttggtggtttagagataatccaaaatcagggtttggtttggggaagaaaatcctccccccttcctcccc
cgccccgttccctaccgcctccactcctgccagctcatttcctcaatttcctttgaacctataggctaaaaaag
aaaggctcattccagccacagggcagccttccctgggcctttgcttctctagcacaattatgggttacttccttt
ttcttaacaaaaaagaatgtttgatttcctctgggtgaccttattgtctgtaattgaaaccctattgagaggtga
tgtctgtgttagccaatgacccaggtgagctgctcgggcttctcttggtatgtcttgtttggaaaagtggatttc
attcatttctgattgtccagttaagtgatcaccaaaggactgagaatctgggagggcaaaaaaaaaaaaaaagtt
tttatgtgcacttaaatttggggacaattttatgtatctgtgttaaggatatgtttaagaacataattcttttgt
tgctgtttgtttaagaagcaccttagtttgtttaagaagcaccttatatagtataatatatatttttttgaaatt
acattgcttgtttatcagacaattgaatgtagtaattctgttctggatttaatttgactgggttaacatgcaaaa
accaaggaaaaatatttagttttttttttttttttttgtatactttcaagctaccttgtcatgtatacagtcatt
tatgcctaaagcctggtgattattcatttaaatgaagatcacatttcatatcaacttttgtatccacagtagaca
aaatagcactaatccagatgcctattgttggatattgaatgacagacaatcttatgtagcaaagattatgcctga
aaaggaaaattattcagggcagctaattttgcttttaccaaaatatcagtagtaatatttttggacagtagctaa
tgggtcagtgggttctttttaatgtttatacttagattttcttttaaaaaaattaaaataaaacaaaaaaaaatt
tctaggactagacgatgtaataccagctaaagccaaacaattatacagtggaaggttttacattattcatccaat
gtgtttctattcatgttaagatactactacatttgaagtgggcagagaacatcagatgattgaaatgttcgccca
ggggtctccagcaactttggaaatctctttgtatttttacttgaagtgccactaatggacagcagatattttctg
gctgatgttggtattgggtgtaggaacatgatttaaaaaaaaactcttgcctctgctttcccccactctgaggca
agttaaaatgtaaaagatgtgatttatctggggggctcaggtatggtggggaagtggattcaggaatctggggaa
tggcaaatatattaagaagagtattgaaagtatttggaggaaaatggttaattctgggtgtgcaccagggttcag
tagagtccacttctgccctggagaccacaaatcaactagctccatttacagccatttctaaaatggcagcttcag
ttctagagaagaaagaacaacatcagcagtaaagtccatggaatagctagtggtctgtgtttcttttcgccattg
cctagcttgccgtaatgattctataatgccatcatgcagcaattatgagaggctaggtcatccaaagagaagacc
ctatcaatgtaggttgcaaaatctaacccctaaggaagtgcagtctttgatttgatttccctagtaaccttgcag
atatgtttaaccaagccatagcccatgccttttgagggctgaacaaataagggacttactgataatttactttg
atcacattaaggtgttctcaccttgaaatcttatacactgaaatggccattgatttaggccactggcttagagta
ctccttcccctgcatgacactgattacaaatactttcctattcatactttccaattatgagatggactgtgggta
ctgggagtgatcactaacaccatagtaatgtctaatattcacaggcagatctgcttggggaagctagttatgtga
aaggcaaatagagtcatacagtagctcaaaaggcaaccataattctctttggtgcaggtcttgggagcgtgatct
agattacactgcaccattcccaagttaatcccctgaaaacttactctcaactggagcaaatgaactttggtccca
aatatccatcttttcagtagcgttaattatgctctgtttccaactgcatttcctttccaattgaattaaagtgtg
gcctcgtttttagtcattaaaattgtttctaagtaattgctgcctctattatggcacttcaattttgcactgt
cttttgagattcaagaaaaatttctattcttttttttgcatccaattgtgcctgaacttttaaaatatgtaaatg
ctgccatgttccaaacccatcgtcagtgtgtgtgtttagagctgtgcaccctagaaacaacatattgtcccatga
gcaggtgcctgagacacagacccctttgcattcacagagaggtcattggttatagagacttgaattaataagtga
cattatgccagtttctgttctctcacaggtgataaacaatgcttttgtgcactacatactcttcagtgtagagc
tcttgttttatgggaaaaggctcaaatgccaaattgtgtttgatggattaatatgccctttttgccgatgcatact
attactgatgtgactcggttttgtcgcagctttgctttgtttaatgaaacacacttgtaaacctcttttgcactt
tgaaaaagaatccagcgggatgctcgagcacctgtaaacaatttctcaacctatttgatgttcaaataaagaat
taaact

SEQ ID No 2

ESR2 Estrogen receptor 2

NM_001040276+1

Hs.525392; HS660607 gtgtgagggcgcccggcttccaggcagtaatgggcgggtccctgcgcgggagcgtggcgggcgctggactctaca
gcagatgtggaactggagagcttggcgcgccttccgactttgtcacacacctgcgccgccagactggggtcgggc
ccctccgcgttctgctctggagtgcctgggtctgggcccagcaccgcgcttttagaatctcctcagctgaatctg
acgctcagcagtgggtgaagcgcagcccccctgtttcaggccctgccgagctggaaggagtgtcagagctggagcg
cgcgtggcccccctctgtgttggggtcaccccggggttgccagggctcagggagggtcgtagtctggattttgtca
cccgcacgtccccaccccccagcaggtctggggttggagaatccacgcgggcttcataagctagatgccagttaa
ctgtcgagaggggacgctccctcctcgtaggcgtccacactggagaaggaataagatgggcgattgcctgggaag
cctgacagggcggcggcagctgggatgctggagaggactggccccttgagttactgagtccgatgaatgtgcttg
ctctgctggaggaaccgcgctcaggttacagtcatcccaatatggttctgaagccattatacttgcccacgaatc
tttgagaacattataatgacctttgtgcctcttcttgcaaggtgttttctcagctgttatctcaagacatggata
taaaaaactcaccatctagccttaattctccttcctcctacaactgcagtcaatccatcttaccccctggagcacg
gctccatatacataccttcctcctatgtagacagccaccatgaatatccagccatgacattctatagccctgctg
tgatgaattacagcattcccagcaatgtcactaacttggaaggtgggcctggtcggcagaccacaagcccaaatg
tgttgtggccaacacctgggcacctttctcctttagtggtccatcgccagttatcacatctgtatgcggaacctc
aaaagagtccctggtgtgaagcaagatcgctagaacacaccttacctgtaaacagagagacactgaaaaggaagg
ttagtgggaaccgttgcgccagccctgttactggtccaggttcaaagagggatgctcacttctgcgctgtctgca
gcgattacgcatcgggatatcactatggagtctggtcgtgtgaaggatgtaaggcctttttaaaagaagcattc
aaggacataatgattatatttgtccagctacaaatcagtgtacaatcgataaaaaccggcgcaagagctgccagg
cctgccgacttcggaagtgttacgaagtgggaatggtgaagtgtggctcccggagagagagatgtgggtaccgcc
ttgtgcggagacagagaagtgccgacgagcagctgcactgtgccggcaaggccaagagaagtggcggccacgcgc
cccgagtgcgggagctgctgctggacgccctgagccccgagcagctagtgctcaccctcctggaggctgagccgc
cccatgtgctgatcagccgccccagtgcgcccttcaccgaggcctccatgatgatgtccctgaccaagttggccg
acaaggagttggtacacatgatcagctgggccaagaagattcccggctttgtggagctcagcctgttcgaccaag
tgcggctcttggagagctgttggatggaggtgttaatgatggggctgatgtggcgctcaattgaccaccccggca
agctcatctttgctccagatcttgttctggacagggatgaggggaaatgcgtagaaggaattctggaaatctttg
acatgctcctggcaactacttcaaggtttcgagagttaaaactccaacacaaagaatatctctgtgtcaaggcca
tgatcctgctcaattccagtatgtaccctctggtcacagcgacccaggatgctgacagcagccggaagctggctc
acttgctgaacgccgtgaccgatgctttggtttgggtgattgccaagagcggcatctcctcccagcagcaatcca
tgcgcctggctaacctcctgatgctcctgtcccacgtcaggcatgcgagggcagaaaaggcctctcaaacactca
cctcatttggaatgaagatggagactcttttgcctgaagcaacgatggagcagtgaccctctaatcaactcggtg
gcctaaagaaaaatcttgggtaacattttcacttcagtttccctctgggatcattgtaatccatgaaaaaaataa
ttttaaagaaagagttaaaatactttgaagttagttatgtggttaaaaccaccttcctttctattatcaatcca
acaatttgataactgtaaacgctaaagtgaagacggattctcttcagatggtctccttaactgcccagggcttgc
agatgtctcacccatgaggggcaccaatgtagaaagctgaggcttcatctactgatgagcttcactggtttcccc
tgaggtttgtgctttggcagagaaggggaggaggggactgggattgtgtggtcagctgtgcctgccaacagatgc
aggttaggaactgtgttcagtatcttccaataagaaaggggaaatgccgatgcctatcctctttgtttaggtaga
aagtaaaatgctactggacttaaatggcaaaaaaaaaaaaaaaa

FIGURE 10

SEQ ID No 3

PGR

Progesterone receptor

NM_000926.4

Hs.368072 agtccacagctgtcactaatcggggtaagccttgttgtatttgtgcgtgtgggtggcattctcaatga
gaactagcttcacttgtcatttgagtgaaatctacaacccgaggcggctagtgctcccgcactactgg
gatctgagatcttcggagatgactgtcgcccgcagtacggagccagcagaagtccgacccttcctggg
aatgggctgtaccgagaggtccgactagccccagggttttagtgaggggcagtggaactcagcgagg
gactgagagcttcacagcatgcacgagtttgatgccagagaaaaagtcgggagataaaggagccgcgt
gtcactaaattgccgtcgcagccgcagccactcaagtgccggacttgtgagtactctgcgtctccagt
cctcggacagaagttggagaactctcttggagaactccccgagttaggagacgagatctcctaacaat
tactactttttcttgcgctccccacttgccgctcgctgggacaaacgacagccacagttcccctgacg
acaggatggaggccaagggcaggagctgaccagcgccgccctcccccgcccccgacccaggaggtgga
gatccctccggtccagccacattcaacacccactttctcctccctctgcccctatattcccgaaaccc
cctcctccttccctttccctcctcctggagacgggggaggagaaaggggagtccagtcgtcatgac
tgagctgaaggcaaagggtccccgggctccccacgtggcgggcggcccgccctcccccgaggtcggat
ccccactgctgtgtcgcccagccgcaggtccgttcccggggagccagacctcggacaccttgcctgaa
gtttcggccatacctatctccctggacgggctactcttccctcggccctgccagggacaggacccctc
cgacgaaaagacgcaggaccagcagtcgctgtcggacgtggagggcgcatattccagagctgaagcta
caaggggtgctggaggcagcagttctagtcccccagaaaaggacagcggactgctggacagtgtcttg
gacactctgttggcgccctcaggtcccgggcagagccaacccagccctcccgcctgcgaggtcaccag
ctcttggtgcctgtttggccccgaacttcccgaagatccaccggctgcccccgccacccagcgggtgt
tgtccccgctcatgagccggtccgggtgcaaggttggagacagctccgggacggcagctgcccataaa
gtgctgccccggggcctgtcaccagcccggcagctgctgctcccggcctctgagagccctcactggtc
cggggccccagtgaagccgtctccgcaggccgctgcggtggaggttgaggaggaggatggctctgagt
ccgaggagtctgcgggtccgcttctgaagggcaaacctcgggctctgggtggcgcggcggctggagga
ggagccgcggctgtcccgccggggggcggcagcaggaggcgtcgccctggtccccaaggaagattcccg
cttctcagcgcccagggtcgccctggtggagcaggacgcgccgatggcgcccgggcgctccccgctgg
ccaccacggtgatggatttcatccacgtgcctatcctgcctctcaatcacgccttattggcagcccgc
actcggcagctgctggaagacgaaagttacgacggcggggccggggctgccagcgcctttgccccgcc
gcggagttcaccctgtgcctcgtccaccccggtcgctgtaggcgacttccccgactgcgcgtacccgc
ccgacgccgagcccaaggacgacgcgtaccctctctatagcgacttccagccgcccgctctaaagata
aaggaggaggaggaaggcgcggaggcctccgcgcgctccccgcgttcctaccttgtggccggtgccaa
ccccgcagccttcccggatttcccgttggggccaccgcccccgctgccgccgcgagcgaccccatcca
gacccggggaagcggcggtgacggccgcacccgccagtgcctcagtctcgtctgcgtcctcctcgggg
tcgaccctggagtgcatcctgtacaaagcggagggcgcgccgccccagcagggcccgttcgcgccgcc
gccctgcaaggcgccgggcgcgagcggctgcctgctcccgcgggacggcctgccctccacctccgcct
ctgccgccgccgccggggcggcccccgcgctctaccctgcactcggcctcaacgggctcccgcagctc ggctaccaggccgccgtgctcaaggagggcctgccgcaggtctacccgccctatctcaactacctgag
gccggattcagaagccagccagagcccacaatacagcttcgagtcattacctcagaagatttgtttaa
tctgtggggatgaagcatcaggctgtcattatggtgtccttacctgtgggagctgtaaggtcttcttt
aagagggcaatggaagggcagcacaactacttatgtgctggaagaaatgactgcatcgttgataaaat
ccgcagaaaaaactgcccagcatgtcgccttagaaagtgctgtcaggctggcatggtccttggaggtc
gaaaatttaaaaagttcaataaagtcagagttgtgagagcactggatgctgttgctctcccacagcca
gtgggcgttccaaatgaaagccaagccctaagccagagattcactttttcaccaggtcaagacataca
gttgattccaccactgatcaacctgttaatgagcattgaaccagatgtgatctatgcaggacatgaca
acacaaaacctgacacctccagttctttgctgacaagtcttaatcaactaggcgagaggcaacttctt
tcagtagtcaagtggtctaaatcattgccaggttttcgaaacttacatattgatgaccagataactct
cattcagtattcttggatgagcttaatggtgtttggtctaggatggagatcctacaaacacgtcagtg
ggcagatgctgtattttgcacctgatctaatactaaatgaacagcggatgaaagaatcatcattctat
tcattatgccttaccatgtggcagatcccacaggagtttgtcaagcttcaagttagccaagaagagtt
cctctgtatgaaagtattgttacttcttaatacaattcctttggaagggctacgaagtcaaacccagt
ttgaggagatgaggtcaagctacattagagagctcatcaaggcaattggtttgaggcaaaaaggagtt
gtgtcgagctcacagcgtttctatcaacttacaaaacttcttgataacttgcatgatcttgtcaaaca
acttcatctgtactgcttgaatacatttatccagtcccgggcactgagtgttgaatttccagaaatga
tgtctgaagttattgctgcacaattacccaagatattggcagggatggtgaaacccttctctttcat
aaaaagtgaatgtcatctttttcttttaaagaattaaattttgtggtatgtctttttgttttggtcag
gattatgaggtcttgagtttttataatgttcttctgaaagccttacatttataacatcatagtgtgta
aatttaaaagaaaaattgtgaggttctaattattttcttttataaagtataattagaatgtttaactg
ttttgtttacccatatttttcttgaagaatttacaagattgaaaaagtactaaaattgttaaagtaaac
tatcttatccatattatttcataccatgtaggtgaggatttttaacttttgcatctaacaaatcatcg
acttaagagaaaaaatcttacatgtaataacacaaagctattatatgttatttctaggtaactccctt
tgtgtcaattatatttccaaaaatgaacctttaaaatggtatgcaaaattttgtctatatatatttgt
gtgaggaggaaattcataactttcctcagattttcaaaagtatttttaatgcaaaaaatgtagaaaga
gtttaaaaccactaaaatagattgatgttcttcaaactaggcaaaacaactcatatgttaagaccatt
ttccagattggaaacacaaatctcttaggaagttaataagtagattcatatcattatgcaaatagtat
tgtgggttttgtaggtttttaaaataaccttttttggggagagaattgtcctctaatgaggtattgcg
agtggacataagaaatcagaagattatggcctaactgtactccttaccaactgtggcatgctgaaagt
tagtcactcttactgattctcaattctctcacctttgaaagtagtaaaatatctttcctgccaattgc
tcctttgggtcagagcttattaacatcttttcaaatcaaaggaaagaagaaagggagaggaggaggag
ggaggtatcaattcacatacctttctcctctttatcctccactatcatgaattcatattatgtttcag
ccatgcaaatctttttaccatgaaatttcttccagaattttcccccttttgacacaaattccatgcatg
tttcaaccttcgagactcagccaaatgtcatttctgtaaaatcttccctgagtcttccaagcagtaat
ttgccttctcctagagtttacctgccattttgtgcacatttgagttacagtagcatgttattttacaa
ttgtgactctcctgggagtctgggagccatataaagtggtcaatagtgtttgctgactgagagttgaa
tgacattttctctctgtcttggtattactgtagatttcgatcattctttggttacatttctgcatatt
tctgtacccatgactttatcactttcttctcccatgctttatctccatcaattatcttcattactttt
aaattttccacctttgcttcctactttgtgagatctctccctttactgactataacatagaagaatag
aagtgtattttatgtgtcttaaggacaatactttagattccttgttctaagtttttaaactgaatgaa
tggaatattatttctctccctaagcaaaattccacaaaacaattatttcttatgtttatgtagcctta
aattgttttgtactgtaaacctcagcataaaaactttcttcatttctaatttcattcaacaaatattg
attgaatacctggtattagcacaagaaaaatgtgctaataagccttatgagaatttggagctgaagaa
agacatataactcaggaaagttacagtccagtagtaggtataaattacagtgcctgataaataggcat

FIGURE 10 (CONTINUED)

tttaatatttgtacactcaacgtatactaggtaggtgcaaaacatttacatataattttactgatacc
catgcagcacaaaggtactaactttaaatattaaataacacctttatgtgtcagtaattcatttgcat
taaatcttattgaaaaggctttcaatatattttccccacaaatgtcatcccaagaaaaaagtattttt
aacatctcccaaatataatagttacaggaaatctacctctgtgagagtgacacctctcagaatgaact
gtgtgacacaagaaaatgaatgtaggtctatccaaaaaaaaccccaagaaacaaaaacaatattatta
gccctttatgcttaagtgatggactcagggaacagttgatgttgtgatcattttattatctgattctt
gttactttgaattaaaccaatattttgatgatataaatcatttccaccagcatatatttaatttccat
aataactttaaaattttctaatttcactcaactatgagggaatagaatgtggtggccacaggtttggc
ttttgttaaaatgtttgatatcttcgatgttgatctctgtctgcaatgtagatgtctaaacactagga
tttaatatttaaggctaagctttaaaaataaagtaccttttttaaaaagaatatggcttcaccaaatgg
aaaatacctaatttctaaatctttttctctacaaagtcctatctactaatgtctccattactatttag
tcatcataaccattatcttcattttacatgtcgtgttctttctggtagctctaaaatgacactaaatc
ataagaagacaggttacatatcaggaaatacttgaaggttactgaaatagattcttgagttaatgaaa
atattttctgtaaaaaggtttgaaaagccatttgagtctaaagcattatacctccattatcagtagtt
atgtgacaattgtgtgtgtgtttaatgtttaaagatgtggcactttttaataaggcaatgctatgcta
tttttttcccatttaacattaagataatttattgctatacagatgatatggaaatatgatgaacaatat
tttttttgccaaaactatgccttgtaagtagccatggaatgtcaacctgtaacttaaattatccacag
atagtcatgtgtttgatgatgggcactgtggagataactgacataggactgtgcccccccttctctgcc
acttactagctggatgagattaagcaagtcatttaactgctctgattaaacctgcctttcccaagtgc
tttgtaatgaatagaaatggaaaccaaaaaaaaacgtatacaggccttcagaaatagtaattgctacta
ttttgttttcattaagccatagttctggctataattttatcaaactcaccagctatattctacagtga
aagcaggattctagaaagtctcactgttttatttatgtcaccatgtgctatgatatatttggttgaat
tcatttgaaattagggctggaagtattcaagtaatttcttctgctgaaaaaatacagtgttttgagtt
tagggcctgttttatcaaagttctaaagagcctatcactcttccattgtagacattttaaaataatga
cactgattttaacatttttaagtgtctttttagaacagagagcctgactagaacacagcccctccaaa
aacccatgctcaaattatttttactatggcagcaattccacaaagggaacaatgggtttagaaatta
caatgaagtcatcaacccaaaaaacatccctatccctaagaaggttatgatataaaatgcccacaaga
aatctatgtctgctttaatctgtcttttattgctttggaaggatggctattacatttttagtttttgc
tgtgaatacctgagcagtttctctcatccatacttatccttcacacatcagaagtcaggatagaatat
gaatcattttaaaaacttttacaactccagagccatgtgcataagaagcattcaaaacttgccaaaac
atacatttttttttcaaatttaaagatactctatttttgtattcaatagctcaacaactgtggtcccca
ctgataaagtgaagtggacaaggagacaagtaatggcataagtttgtttttcccaaagtatgcctgtt
caatagccattggatgtgggaaatttctacatctcttaaaattttacagaaaatacatagccagatag
tctagcaaaagttcaccaagtcctaaattgcttatccttacttcactaagtcatgaaatcattttaat
gaaaagaacatcacctaggttttgtggtttcttttttttcttattcatggctgagtgaaaacaacaatc
tctgtttctccctagcatctgtggactatttaatgtaccattattccacactctatggtccttactaa
atacaaaattgaacaaaaagcagtaaaacaactgactcttcacccatattataaaatataatccaagc
cagattagtcaacatccataagatgaatccaagctgaactgggcctagattattgagttcaggttgga
tcacatccctatttattaataaacttaggaaagaaggccttacagaccatcagttagctggagctaat
agaacctacacttctaaagttcggcctagaatcaatgtggccttaaaagctgaaaagaagcaggaaag
aacagttttcttcaataatttgtccaccctgtcactggagaaaatttaagaatttggggtgttggta
gtaagttaaacacagcagctgttcatggcagaaattattcaatacataccttctctgaatatcctata
accaaagcaaagaaaaacaccaaggggtttgttctcctccttggagttgacctcattccaaggcagag
ctcaggtcacaggcacaggggctgcgcccaagcttgtccgcagccttatgcagctgtggagtctggaa
gactgttgcaggactgctggcctagtcccagaatgtcagcctcattttcgatttactggctcttgttg

FIGURE 10 (CONTINUED)

ctgtatgtcatgctgaccttattgttaaacacaggtttgtttgctttttttccactcatggagacatg
ggagaggcattatttttaagctggttgaaagctttaaccgataaagcatttttagagaaatgtgaatc
aggcagctaagaaagcatactctgtccattacggtaaagaaaatgcacagattattaactctgcagtg
tggcattagtgtcctggtcaatattcggatagatatgaataaaatatttaaatggtattgtaaatagt
tttcaggacatatgctatagcttatttttattatcttttgaaattgctcttaatacatcaaatcctga
tgtattcaatttatcagatataaattattctaaatgaagcccagttaaatgtttttgtcttgtcagtt
atatgttaagtttctgatctctttgtctatgacgtttactaatctgcatttttactgttatgaattat
tttagacagcagtggtttcaagctttttgccactaaaaatacctttttatttttctcctcccccagaaaa
gtctataccttgaagtatctatccaccaaactgtacttctattaagaaatagttattgtgttttctta
atgttttgttattcaaagacatatcaatgaaagctgctgagcagcatgaataacaattatatccacac
agatttgatatattttgtgcagccttaacttgatagtataaaatgtcattgctttttaaataatagtt
agtcaatggacttctatcatagctttcctaaactaggttaagatccagagctttggggtcataatata
ttacatacaattaagttatctttttctaagggctttaaaattcatgagaataaccaaaaaaggtatgt
ggagagttaatacaaacataccatattcttgttgaaacagagatgtggctctgcttgttctccataag
gtagaaatactttccagaatttgcctaaactagtaagccctgaatttgctatgattagggataggaag
agattttcacatggcagactttagaattcttcactttagccagtaaagtatctcctttttgatcttagt
attctgtgtattttaacttttctgagttgtgcatgtttataagaaaaatcagcacaaagggtttaagt
taaagcctttttactgaaatttgaaagaaacagaagaaaatatcaaagttctttgtattttgagagga
ttaaatatgatttacaaaagttacatggagggctctctaaaacattaaattaattatttttttgttgaa
aagtcttactttaggcatcattttattcctcagcaactagctgtgaagcctttactgtgctgtatgcc
agtcactctgctagattgtggagattaccagtgttcccgtcttctccgagcttagagttggatgggga
ataaagacaggtaaacagatagctacaatattgtactgtgaatgcttatgctggaggaagtacaggga
actattggagcacctaagaggagcacctaccttgaatttaggggttagcagaggcatcctgaaaaaag
tcaaagctaagccacaatctataagcagtttaggaattagcagaacgtgcgtggtgaggagatgccaa
aggcaagaagagaagagtattccaaacaggagggattccaaagagagaagagtatcccaaacaacatt
tgcacaaacctgatggggagagagaatgtggggtggggatggatgatgagactgaagaagaaagccag
gtctagataatcagtggccttgtacaccatgttaaagagtgtagacttgattctgttgtaaacaggaa
agcagcacaattcatatgaatattttagaagactcccactggaatatggagaataaagttggagatga
ctaatcctggaagcagggagaacatttttgaggaagttgcactattttggtgaaaatgatgatcataa
acatgaagaattgtaggtgatcatgacctcctctctaattttccagaagggttttggaagatataaca
taggaacattgacaggactgacgaaaggagatgaaatacaccatataaattgtcaaacacaaggccag
atgtctaattatttttgcttatgtgttgaaattacaaatttttcatcaggaaaccaaaaactacaaaac
ttagttttcccaagtcccagaattctatctgtccaaacaatctgtaccactccacctatatccctacc
tttgcatgtctgtccaacctcaaagtccaggtctatacacacgggtaagactagagcagttcaagttt
cagaaaatgagaaagaggaactgagttgtgctgaacccatacaaaataaacacattctttgtatagat
tcttggaacctcgagaggaattcacctaactcataggtatttgatggtatgaatccatggctgggctc
ggcttttaaaaagccttatctgggattccttctatggaaccaagttccatcaaagcccatttaaaagc
ctacattaaaaacaaaattcttgctgcattgtatacaaataatgatgtcatgatcaaataatcagatg
ccattatcaagtggaattacaaaatggtatacccactccaaaaaaaaaaaaaaagctaaattctcagt
agaacattgtgacttcatgagccctccacagccttggagctgaggagggagcactggtgagcagtagg
ttgaagagaaaacttggcgcttaataatctatccatgtttttttcatctaaaagagccttctttttgga
ttaccttattcaatttccatcaaggaaattgttagttccactaaccagacagcagctgggaaggcaga
agcttactgtatgtacatggtagctgtgggaaggaggtttctttctccaggtcctcactggccataca
ccagtcccttgttagttatgcctggtcatagacccccgttgctatcatctcatatttaagtctttggc
ttgtgaatttatctattctttcagcttcagcactgcagagtgctgggactttgctaacttccatttct

FIGURE 10 (CONTINUED)

tgctggcttagcacattcctcataggcccagctcttttctcatctggccctgctgtggagtcaccttg
ccccttcaggagagccatggcttaccactgcctgctaagcctccactcagctgccaccacactaaatc
caagcttctctaagatgttgcagactttacaggcaagcataaaaggcttgatcttcctggacttccct
ttacttgtctgaatctcacctccttcaactttcagtctcagaatgtaggcatttgtcctctttgccct
acatcttccttcttctgaatcatgaaagcctctcacttcctcttgctatgtgctggaggcttctgtca
ggttttagaatgagttctcatctagtcctagtagcttttgatgcttaagtccaccttttaaggatacc
tttgagatttagaccatgtttttcgcttgagaaagccctaatctccagacttgcctttctgtggattt
caaagaccaactgaggaagtcaaaagctgaatgttgactttctttgaacatttccgctataacaattc
caattctcctcagagcaatatgcctgcctccaactgaccaggagaaaggtccagtgccaaagagaaaa
acacaaagattaattatttcagttgagcacatactttcaaagtggtttgggtattcatatgaggtttt
ctgtcaagagggtgagactcttcatctatccatgtgtgcctgacagttctcctggcactggctggtaa
cagatgcaaaactgtaaaaattaagtgatcatgtattttaacgatatcatcacatacttattttctat
gtaatgttttaaatttcccctaacatactttgactgttttgcacatggtagatattcacatttttttg
tgttgaagttgatgcaatcttcaaagttatctaccccgttgcttattagtaaaactagtgttaatact
tggcaagagatgcagggaatctttctcatgactcacgccctatttagttattaatgctactaccctat
tttgagtaagtagtaggtccctaagtacattgtccagagttatacttttaaagatatttagccccata
tacttcttgaatctaaagtcatacaccttgctcctcatttctgagtgggaaagacatttgagagtatg
ttgacaattgttctgaaggtttttgccaagaaggtgaaactgtcctttcatctgtgtatgcctggggc
tgggtccctggcagtgatggggtgacaatgcaaagctgtaaaaactaggtgctagtgggcacctaata
tcatcatcatatacttattttcaagctaatatgcaaaatcccatctctgtttttaaactaagtgtaga
tttcagagaaaatattttgtggttcacataagaaaacagtctactcagcttgacaagtgttttatgtt
aaattggctggtggtttgaaatgaatcatcttcacataatgttttctttaaaaatattgtgaatttaa
ctctaattcttgttattctgtgtgataataaagaataaactaatttcta

SEQ ID No 4

AR

Androgen receptor

NM_000044+2

Hs.496240 cgagatcccggggagccagcttgctgggagagcgggacggtccggagcaagcccagaggcagaggagg
cgacagagggaaaaagggccgagctagccgctccagtgctgtacaggagccgaagggacgcaccacgc
cagccccagcccggctccagcgacagccaacgcctcttgcagcgcggcggcttcgaagccgccgcccg
gagctgccctttcctcttcggtgaagtttttaaaagctgctaaagactcggaggaagcaaggaaagtg
cctggtaggactgacggctgcctttgtcctcctcctctccaccccgcctcccccccaccctgccttccc
cccctcccccgtcttctctcccgcagctgcctcagtcggctactctcagccaaccccccctcaccaccc
ttctccccacccgcccccccgcccccgtcggcccagcgctgccagcccgagtttgcagagaggtaact
ccctttggctgcgagcgggcgagctagctgcacattgcaaagaaggctcttaggagccaggcgactgg
ggagcggcttcagcactgcagccacgacccgcctggttaggctgcacgcggagagaaccctctgtttt
cccccactctctctccacctcctcctgccttccccaccccgagtgcggagccagagatcaaaagatga
aaaggcagtcaggtcttcagtagccaaaaaacaaaacaaacaaaaacaaaaaagccgaaataaaagaa
aaagataataactcagttcttatttgcacctacttcagtggacactgaatttggaaggtggaggattt
tgtttttttcttttaagatctgggcatcttttgaatctacccttcaagtattaagagacagactgtga
gcctagcagggcagatcttgtccaccgtgtgtcttcttctgcacgagactttgaggctgtcagagcgc
tttttgcgtggttgctcccgcaagtttccttctctggagcttcccgcaggtgggcagctagctgcagc
gactaccgcatcatcacagcctgttgaactcttctgagcaagagaaggggaggcggggtaaggaagt
aggtggaagattcagccaagctcaaggatggaagtgcagttagggctgggaagggtctaccctcggcc
gccgtccaagacctaccgaggagctttccagaatctgttccagagcgtgcgcgaagtgatccagaacc
cgggccccaggcacccagaggccgcgagcgcagcacctcccggcgccagtttgctgctgctgcagcag
cagcagcagcagcagcagcagcagcagcagcagcagcagcagcagcagcagcagcagcagcaagagac
tagccccaggcagcagcagcagcagcagggtgaggatggttctccccaagcccatcgtagaggcccca
caggctacctggtcctggatgaggaacagcaaccttcacagccgcagtcggccctggagtgccacccc
gagagaggttgcgtcccagagcctggagccgccgtggccgccagcaaggggctgccgcagcagctgcc
agcacctccggacgaggatgactcagctgccccatccacgttgtccctgctgggccccactttccccg
gcttaagcagctgctccgctgaccttaaagacatcctgagcgaggccagcaccatgcaactccttcag
caacagcagcaggaagcagtatccgaaggcagcagcagcgggagagcgagggaggcctcgggggctcc
cacttcctccaaggacaattacttagggggcacttcgaccatttctgacaacgccaaggagttgtgta
aggcagtgtcggtgtccatgggcctgggtgtggaggcgttggagcatctgagtccaggggaacagctt
cggggggattgcatgtacgccccactttttgggagttccacccgctgtgcgtcccactccttgtgcccc
attggccgaatgcaaaggttctctgctagacgacagcgcaggcaagagcactgaagatactgctgagt
attcccctttcaagggaggttacaccaaagggctagaaggcgagagcctaggctgctctggcagcgct
gcagcagggagctccgggacacttgaactgccgtctaccctgtctctctacaagtccggagcactgga cgaggcagctgcgtaccagagtcgcgactactacaactttccactggctctggccggaccgccgcccc
ctccgccgcctccccatccccacgctcgcatcaagctggagaacccgctggactacggcagcgcctgg
gcggctgcggcggcgcagtgccgctatggggacctggcgagcctgcatggcgcgggtgcagcgggacc
cggttctgggtcaccctcagccgccgcttcctcatcctggcacactctcttcacagccgaagaaggcc
agttgtatggaccgtgtggtggtggtgggggtggtggcggcggcggcggcggcggcggcggcggcggc
ggcggcggcggcggcggcgaggcgggagctgtagccccctacggctacactcggccccctcaggggct
ggcgggccaggaaagcgacttcaccgcacctgatgtgtggtaccctggcggcatggtgagcagagtgc
cctatcccagtcccacttgtgtcaaaagcgaaatgggcccctggatggatagctactccggaccttac
ggggacatgcgtttggagactgccagggaccatgttttgcccattgactattactttccaccccagaa
gacctgcctgatctgtggagatgaagcttctgggtgtcactatggagctctcacatgtggaagctgca
aggtcttcttcaaaagagccgctgaagggaaacagaagtacctgtgcgccagcagaaatgattgcact
attgataaattccgaaggaaaaattgtccatcttgtcgtcttcggaaatgttatgaagcagggatgac
tctgggagcccggaagctgaagaaacttggtaatctgaaactacaggaggaaggagaggcttccagca
ccaccagccccactgaggagacaacccagaagctgacagtgtcacacattgaaggctatgaatgtcag
cccatctttctgaatgtcctggaagccattgagccaggtgtagtgtgtgctggacacgacaacaacca
gcccgactcctttgcagccttgctctctagcctcaatgaactgggagagagacagcttgtacacgtgg
tcaagtgggccaaggccttgcctggcttccgcaacttacacgtggacgaccagatggctgtcattcag
tactcctggatggggctcatggtgtttgccatgggctggcgatccttcaccaatgtcaactccaggat
gctctacttcgcccctgatctggttttcaatgagtaccgcatgcacaagtcccggatgtacagccagt
gtgtccgaatgaggcacctctctcaagagtttggatggctccaaatcacccccaggaattcctgtgc
atgaaagcactgctactcttcagcattattccagtggatgggctgaaaaatcaaaaattctttgatga
acttcgaatgaactacatcaaggaactcgatcgtatcattgcatgcaaaagaaaaaatcccacatcct
gctcaagacgcttctaccagctcaccaagctcctggactccgtgcagcctattgcgagagagctgcat
cagttcacttttgacctgctaatcaagtcacacatggtgagcgtggactttccggaaatgatggcaga
gatcatctctgtgcaagtgcccaagatcctttctgggaaagtcaagcccatctatttccacacccagt
gaagcattggaaaccctatttccccaccccagctcatgcccccttcagatgtcttctgcctgttata
actctgcactactcctctgcagtgccttggggaatttcctctattgatgtacagtctgtcatgaacat
gttcctgaattctatttgctgggctttttttttctctttctctcctttctttttcttcttccctccct
atctaaccctcccatggcaccttcagactttgcttcccattgtggctcctatctgtgttttgaatggt
gttgtatgcctttaaatctgtgatgatcctcatatggcccagtgtcaagttgtgcttgtttacagcac
tactctgtgccagccacacaaacgtttacttatcttatgccacgggaagtttagagagctaagattat
ctggggaaatcaaaacaaaaacaagcaaac

SEQ ID No 5

AR

Androgen receptor

NM_001011645+1

Hs.496240 gctgcgagcagagagggattcctcggaggtcatctgttccatcttcttgcctatgcaaatgcctgcct
gaagctgctggaggctggctttgtaccggactttgtacagggaaccagggaaacgaatgcagagtgct
cctgacattgcctgtcactttttcccatgatactctggcttcacagtttggagactgccagggaccat
gttttgcccattgactattactttccaccccagaagacctgcctgatctgtggagatgaagcttctgg
gtgtcactatggagctctcacatgtggaagctgcaaggtcttcttcaaaagagccgctgaagggaaac
agaagtacctgtgcgccagcagaaatgattgcactattgataaattccgaaggaaaaattgtccatct
tgtcgtcttcggaaatgttatgaagcagggatgactctgggagcccggaagctgaagaaacttggtaa
tctgaaactacaggaggaaggagaggcttccagcaccaccagccccactgaggagacaacccagaagc
tgacagtgtcacacattgaaggctatgaatgtcagcccatctttctgaatgtcctggaagccattgag
ccaggtgtagtgtgtgctggacacgacaacaaccagcccgactcctttgcagccttgctctctagcct
caatgaactgggagagagacagcttgtacacgtggtcaagtgggccaaggccttgcctggcttccgca
acttacacgtggacgaccagatggctgtcattcagtactcctggatggggctcatggtgtttgccatg
ggctggcgatccttcaccaatgtcaactccaggatgctctacttcgcccctgatctggttttcaatga
gtaccgcatgcacaagtcccggatgtacagccagtgtgtccgaatgaggcacctctctcaagagtttg
gatggctccaaatcacccccaggaattcctgtgcatgaaagcactgctactcttcagcattattcca
gtggatgggctgaaaaatcaaaaattctttgatgaacttcgaatgaactacatcaaggaactcgatcg
tatcattgcatgcaaaagaaaaaatcccacatcctgctcaagacgcttctaccagctcaccaagctcc
tggactccgtgcagcctattgcgagagagctgcatcagttcacttttgacctgctaatcaagtcacac
atggtgagcgtggactttccggaaatgatggcagagatcatctctgtgcaagtgcccaagatcctttc
tgggaaagtcaagcccatctatttccacacccagtgaagcattggaaaccctatttccccaccccagc
tcatgcccccctttcagatgtcttctgcctgttataactctgcactactcctctgcagtgccttgggga
atttcctctattgatgtacagtctgtcatgaacatgttcctgaattctatttgctgggcttttttttt
ctctttctctcctttctttttcttcttccctccctatctaaccctcccatggcaccttcagactttgc
ttcccattgtggctcctatctgtgttttgaatggtgttgtatgcctttaaatctgtgatgatcctcat
atggcccagtgtcaagttgtgcttgtttacagcactactctgtgccagccacacaaacgtttacttat
cttatgccacgggaagtttagagagctaagattatctggggaaatcaaaacaaaaacaagcaaac

FIGURE 13

SEQ ID No 6

CYP19

Aromatase

NM_000103.3 gggagtttctggagggctgaacacgtggaggcaaacaggaaggtgaagaagaacttatcctatcagga
cggaaggtcctgtgctcgggatcttccagacgtcgcgactctaaattgccccctctgaggtcaaggaa
cacaagatggttttggaaatgctgaacccgatacattataacatcaccagcatcgtgcctgaagccat
gcctgctgccaccatgccagtcctgctcctcactggcctttttctcttggtgtggaattatgagggca
catcctcaataccaggtcctggctactgcatgggaattggacccctcatctcccacggcagattcctg
tggatggggatcggcagtgcctgcaactactacaaccgggtatatggagaattcatgcgagtctggat
ctctggagaggaaacactcattatcagcaagtcctcaagtatgttccacataatgaagcacaatcatt
acagctctcgattcggcagcaaacttgggctgcagtgcatcggtatgcatgagaaaggcatcatattt
aacaacaatccagagctctggaaaacaactcgacccttctttatgaaagctctgtcaggccccggcct
tgttcgtatggtcacagtctgtgctgaatccctcaaaacacatctggacaggttggaggaggtgacca
atgaatcgggctatgtggacgtgttgacccttctgcgtcgtgtcatgctggacacctctaacacgctc
ttcttgaggatccctttggacgaaagtgctatcgtggttaaaatccaaggttattttgatgcatggca
agctctcctcatcaaaccagacatcttctttaagatttcttggctatacaaaaagtatgagaagtctg
tcaaggatttgaaagatgccatagaagttctgatagcagaaaaaagacgcaggatttccacagaagag
aaactggaagaatgtatggactttgccactgagttgattttagcagagaaacgtggtgacctgacaag
agagaatgtgaaccagtgcatattggaaatgctgatcgcagctcctgacaccatgtctgtctctttgt
tcttcatgctatttctcattgcaaagcaccctaatgttgaagaggcaataataaaggaaatccagact
gttattggtgagagagacataaagattgatgatatacaaaaattaaaagtgatggaaaacttcattta
tgagagcatgcggtaccagcctgtcgtggacttggtcatgcgcaaagccttagaagatgatgtaatcg
atggctacccagtgaaaaaggggacaaacattatcctgaatattggaaggatgcacagactcgagttt
ttccccaaacccaatgaatttactcttgaaaattttgcaaagaatgttccttataggtactttcagcc
atttggctttgggccccgtggctgtgcaggaaagtacatcgccatggtgatgatgaaagccatcctcg
ttacacttctgagacgattccacgtgaagacattgcaaggacagtgtgttgagagcatacagaagata
cacgacttgtccttgcacccagatgagactaaaaacatgctggaaatgatctttaccccaagaaactc
agacaggtgtctggaacactagagaaggctggtcagtacccactctggagcatttctcatcagtagtt
cacatacaaatcatccatccttgccaatagtgtcatcctcacagtgaacactcagtggcccatggcat
tttataggcatacctcctatgggttgtcaccaagctaggtgctatttgtcatctgctcctgttcacac
cagagaaccaggctacaagagaaaaagcagaggccaagagtttgagggagaaatagtcggtgaagaaa
ccgtatccataaagacccgattccaccaaatgtgctttgagaaggataggccttcattaacaaaatgt
atgtctggttccccagtagagctctactgcctcaacccaaggggatttttatgtctgggcagaaaca
ctcaagttgattagaaagaccaggccaatgtcagggtacctggggccaaacccacctgctagtgtgaa
ttaaagtactttaattttgttttctgtggaggtggaaaagcaacattcatagtctttggagaaatgct
tagaaattcagcatttgacccttgctgtgaattaagcccaattaattcctgtttgtctacatatgatc
tgtctgtggcaaaagtttaatcagaggaaattctttcccagtctgtcgatttatgcctcagccacttg
cctgtgctacaattcattgtgttacctgtagattcaggtaatacaaactatatataatcatcaagtaa
tacaaactaatttagtaatagcctgggttaagtattattagggccctgtgtctgctgtagaaaaaaa attcacatgatgcacttcaaattcaaataaaaatccttttggcatgttcccatttttgcttagctcaa
ttagtgtggctaaccaagagataactgtaaatgtgacattgatttgctcttactacagcttcagtgat
tggggaggaaaagtcccaacccaatgggctcaaacttctaaggggtactcctctcatccccttatcc
ttctccctcgacattttctccctctttcttcccatgaccccaaagccaagggcaacagatcagtaaag
aacgtggtcagagtagaacccctgaagtatttttaatcctacctcaaatttaacagttacctgaga
gatttaacattatctagttcattgaatcattgtatgtggtcatggataaattgcacaccttggaattc
gctttctaaaggaaatcaaatgaatggaggaactttccaaacaccactttacttgtgttatatagcca
atataactatctctactgaatgtcattgaaaaactaaaaaattaaacttatttacaaataggtaaata
tttgtcattgaatccattgccatcccatttgactgttcttttcatcctactgtctagtaataagctga
gtataagatgacagtgtaatctccctgaaagcaggagctactttctttcttttgtaatctatttccat
ccccatttccctgtcctgtctccctgtattcactcccaagctcagttctgaatagacattcctgctca
gagatactcccaactgatgcagaaaccaaataaagaggtaggtattccaagaattcaagaatggacat
tagtaaagaataaaacatttatttgagcttggaattatttggatcatctatatggcctaaaaatatat
ggactatgcctgtgtacctgaatacgtatgtagtcaggtcaagacaatcatccaaataacttagaccc
ctaaaagcaaggccaggatttgcaatttaatgtgtcccaattaattcacttgaaaattagtaacactc
tgtttacgttgcctctggctggagctgcatggtggaagaagcccaactttggatccatgtacttcacc
catccaatactcttgggacatttatgtgtattttatctgtatatatgaagccaatgtctatgtctaca
cagtcaaagtgaaatgcatgtttgatatagctgtacatagatatctattttgcaggtacaaaaatatc
ctgggggaaaactgggagtggaagggtgggggtgggagtgagggacatgggggagggacaggaagag
gagaagtgttggtttgaacgatccaagcaaactctcccagaatcaaattacctgggtagttgttcaac
ttttcactctgcttagcctgtatagacaaaccccatatatttgtagaggcttggccttggaattctgg
aataccattggcttttcagtaggctgatgaacacattttgaaaattctattatcttcagaattttgcc
ccattgttaagtgcttaaccgtcactcttgaatgtgcaatgtgctgtggattccattttcatcagttc
tgaaagaactgcaatgtgtaaattatcagtgaaatgcatgcatataagggctctatcattatcaaatt
gtaaggacaattgtacccttctatatctttgggcatgctagacacccccatgccttcattgagatccc
atttttcccccctctcaagtggaaaataatcacatccagcaagctctctcattattgagaaataccattt
ggaaattgccactttttattcctaagcagcacctttcactgttcatgatgctaatgttccacaaaagc
atgtgccattggcccactgaaggatagagggacccttttcaatctatatcagctgggctctgggactg
aatctctcacctattcttgcagaaagacatactaattaaaccttgtcaaagtaaaaaaaaaaaaaaa
aa

Seq ID No 7

SNAI1 Snail homolog 1

NM 005985.2

Hs.48029 ggcacggcctagcgagtggttcttctgcgctactgctgcgcgaatcggcgaccccagtgcctcgacca
ctatgccgcgctctttcctcgtcaggaagccctccgaccccaatcggaagcctaactacagcgagctg
caggactctaatccagagtttaccttccagcagccctacgaccaggcccacctgctggcagccatccc
acctccggagatcctcaaccccaccgcctcgctgccaatgctcatctgggactctgtcctggcgcccc
aagcccagccaattgcctgggcctcccttcggctccaggagagtcccagggtggcagagctgacctcc
ctgtcagatgaggacagtgggaaaggctcccagcccccagcccaccctcaccggctccttcgtcctt
ctcctctacttcagtctcttccttggaggccgaggcctatgctgccttcccaggcttgggccaagtgc
ccaagcagctggcccagctctctgaggccaaggatctccaggctcgaaaggccttcaactgcaaatac
tgcaacaaggaatacctcagcctgggtgccctcaagatgcacatccgaagccacacgctgccctgcgt
ctgcggaacctgcgggaaggccttctctaggccctggctgctacaaggccatgtccggacccacactg
gcgagaagcccttctcctgtccccactgcagccgtgccttcgctgaccgctccaacctgcgggcccac
ctccagacccactcagatgtcaagaagtaccagtgccaggcgtgtgctcggaccttctcccgaatgtc
cctgctccacaagcaccaagagtccggctgctcaggatgtccccgctgaccctcgaggctccctcttc
ctctccatacctgcccctgcctgacagccttccccagctccagcaggaaggaccccacatccttctca
ctgccatggaattccctcctgagtgccccacttctggccacatcagccccacaggactttgatgaaga
ccattttctggttctgtgtcctctgcctgggctctggaagaggccttcccatggccatttctgtggag
ggagggcagctggcccccagccctggggattcctgagctggcctgtctgcgtgggtttttgtatcca
gagctgtttggatacagctgctttgagctacaggacaaaggctgacagactcactgggaagctcccac
cccactcaggggaccccactcccctcacacacaccccccccacaaggaaccctcaggccaccctccacg
aggtgtgactaactatgcaataatccacccccaggtgcagccccagggcctgcggaggcggtggcaga
ctagagtctgagatgccccgagcccaggcagctatttcagcctcctgtttggtggggtggcacctgtt
tcccgggcaatttaacaatgtctgaaaggactgtgagtaatggctgtcacttgtcgggggcccaag
tggggtgctctggtctgaccgatgtgtctcccagaactattctgggggcccgacaggtgggcctggga
ggaagatgtttacatttttaaaggtacactggtatttatatttcaaacattttgtatcaaggaaacgt
tttgtatagttatatgtacagtttattgatattcaataaagcagttaatttatatattaaaaaaaaaa
aaaaaaaa

FIGURE 15

Seq ID No 8

SNAI2 SLUG Snail homolog 2

NM 003068.3

Hs.360174

```
agttcgtaaaggagccgggtgacttcagaggcgccggcccgtccgtctgccgcacctgagcacggccc
ctgcccgagcctggcccgccgcgatgctgtagggaccgccgtgtcctcccgccggaccgttatccgcg
ccgggcgcccgccagacccgctggcaagatgccgcgctccttcctggtcaagaagcatttcaacgcct
ccaaaaagccaaactacagcgaactggacacacatacagtgattatttccccgtatctctatgagagt
tactccatgcctgtcataccacaaccagagatcctcagctcaggagcatacagccccatcactgtgtg
gactaccgctgctccattccacgcccagctacccaatggcctctctcctctttccggatactcctcat
ctttggggcgagtgagtcccccctcctccatctgacacctcctccaaggaccacagtggctcagaaagc
cccattagtgatgaagaggaaagactacagtccaagctttcagaccccccatgccattgaagctgaaaa
gtttcagtgcaatttatgcaataagacctattcaactttttctgggctggccaaacataagcagctgc
actgcgatgcccagtctagaaaatctttcagctgtaaatactgtgacaaggaatatgtgagcctgggc
gccctgaagatgcatattcggacccacacattaccttgtgtttgcaagatctgcggcaaggcgtttc
cagaccctggttgcttcaaggacacattagaactcacacgggggagaagcctttttcttgccctcact
gcaacagagcatttgcagacaggtcaaatctgagggctcatctgcagacccattctgatgtaaagaaa
taccagtgcaaaaactgctccaaaaccttctccagaatgtctctcctgcacaaacatgaggaatctgg
ctgctgtgtagcacactgagtgacgcaatcaatgtttactcgaacagaatgcatttcttcactccgaa
gccaaatgacaaataaagtccaaaggcattttctcctgtgctgaccaaccaaataatatgtatagaca
cacacacatatgcacacacacacacacacacccacagagagagagctgcaagagcatggaattcatgt
gtttaaagataatcctttccatgtgaagtttaaaattactatatttgctgatggctagattgagag
aataaaagacagtaacctttctcttcaaagataaaatgaaaagcacattgcatcttttcttcctaaaa
aaatgcaaagatttacattgctgccaaatcatttcaactgaaaagaacagtattgctttgtaatagag
tctgtaataggatttcccataggaagagatctgccagacgcgaactcaggtgccttaaaagtattcc
aagtttactccattacatgtcggttgtctggttgccattgttgaactaaagccttttttgattacct
gtagtgctttaaagtatatttttaaaagggaggaaaaaaataacaagaacaaaacacaggagaatgta
ttaaaagtatttttgttttgttttgtttttgccaattaacagtatgtgccttggggggaggagggaaag
attagctttgaacattcctggcgcatgctccattgtcttactattttaaaacattttaataattttg
aaaattaattaaagatgggaataagtgcaaaagaggattcttacaaattcattaatgtacttaaacta
tttcaaatgcataccacaaatgcaataatacaataccccttccaagtgcctttttaaattgtatagtt
gatgagtcaatgtaaatttgtgtttatttttatatgattgaatgagttctgtatgaaactgagatgtt
gtctatagctatgtctataaacaacctgaagacttgtgaaatcaatgtttctttttaaaaaacaatt
ttcaagtttttttacaataaacagttttgatttaaaatctcgtttgtatactattttcagagacttt
acttgcttcatgattagtaccaaaccactgtacaaagaattgtttgttaacaagaaaaaaa
```

FIGURE 16

Seq ID No 9

SNAI3 SMUC; Snail homolog 3

NM 178310.3

Hs.673548 cagcagtccggacccaggcgcgcccctcccgccccagcccaccccggcctgccgcccgggaggggaac
atgccgcgctccttcctggtgaaaacgcactccagccacagggtccccaactaccggcggctggagac
gcagagagaaatcaatggtgcctgctctgcctgtgggggctggtggtgcccctcctcccccgagaca
aggaggccccttctgtgcccggtgaccttccccagccctgggaccgctcctcggccgtcgcctgcatc
tccctgcccctcctgccacggatcgaggaagctctggggcctctgggctggacgccttggaagtcag
cgaggtcgaccctcgggccagccgggccgccattgtacccctcaaagacagcctgaaccacctcaacc
tgcccccactgctggtgctgcccacacggtggtccccgaccttgggcccagaccggcacggggctccg
gaaaaactgcttggggctgagcggatgccccgagccccgggcggctttgagtgcttccactgccacaa
accctaccacacgctggccgggctggccaggcaccggcagctgcactgccacctgcaggtggggcgtg
tcttcacctgcaagtactgcgacaaggagtacaccagcctgggtgccctcaagatgcacatccgcact
cacacgctgccctgcacctgcaagatctgtggcaaggccttctccaggccctggttactgcagggcca
tgtccgcacccacacaggggagaagccctatgcctgctcgcactgcagcagggcctttgccgaccgct
ccaaccttcgggcccatctgcaaacgcactcagacgccaagaagtaccggtgccggcgctgcaccaag
accttctcccgcatgtccctcctggcgcggcatgaggagtctggctgctgcccgggcccctgagaggc
acgtggtcggcgcaggtaggagggatggtcctcaccgggagagctggcgtccctcctgcccccagagg
agccaggagtctgggagggcggggcctggcctcacacttggtgcgtcctccacatctgcgtccaatca
gaaccaaagaagtccagcgggggccactgggccggaggacactcccccaggcatcccaccgcgcggag
cccactcagaggagactcctctcccggggaaggctttcatcagaacaagagccatggttccatttcga
cacggccaggtctccggggctacccttccaagagtcagagcctcggggaggtggccgccagcatgggc
cggcactgccgccggatggctggcaaggctgcctagttccattgcagcagaaatgaacagttctgact
tatagtgagcaccgccctgtggcccttcctcagtaggcacaactacctctcagccagcccccgccagc
ctttggtttggggtctgggacgagctgccccatgtcacacgtctatgtgcatgtgcacacacactcaa
acatgtacacacacgtgccctccccacctcactagactctccgggagatggggcaggactgggagagc
ccacgattggtgatttgggtgtgttgggatgaggcggagtgcctgtgggatttgtcccggtcagagcc
tcaggggctggggtctcagggcactcagcttcccaggcaataacagccgtggggtaataaatggtct
ctgcacacctgca

METHOD TO ASSESS PROGNOSIS AND TO PREDICT THERAPEUTIC SUCCESS IN CANCER BY DETERMINING HORMONE RECEPTOR EXPRESSION LEVELS

CROSS-REFERENCE TO RELATED APPLICATION

This application claims priority to International Application No. PCT/EP2010/055745 filed on 28 Apr. 2010, which, in turn, claims priority from Patent Application No. EP 09159005.9, filed on 29 Apr. 2009, each of which is incorporated by reference in its entirety.

FIELD OF THE INVENTION

The present invention relates to a method to assess the prognosis of cancer and to predict therapeutic outcome in cancer treatment. The invention has been tested to be useful for different cancer diseases such as but not limited to lung, ovarian, breast and prostate cancer.

BACKGROUND OF THE INVENTION

Cancer is a class of diseases in which a group of cells display uncontrolled growth (division beyond the normal limits), invasion (intrusion on and destruction of adjacent tissues), and sometimes metastasis (spread to other locations in the body via lymph or blood).

Lung cancer is a cancerous disease of uncontrolled cell growth in tissues of the lung. This growth may lead to metastasis, which is the infiltration and invasion of adjacent tissue and infiltration beyond the lungs. The vast majority of primary lung cancers are carcinomas of the lung, derived from epithelial cells.

Response to chemotherapy in lung cancer is comparatively low with about 10%-30% of patients having benefit from treatment, while having serious side effects and being costly for the national health systems. Despite responsiveness towards chemotherapy, the survival of lung cancer patients is still very poor. Lung cancer is the most lethal cancer in the world with estimated 215,000 new cases and 162,000 deaths per year in the US (Jemal, et al. 2008; 5 year overall survival: Stage I 50%, Stage IV 3%) in part due to the fact that most cases are detected in the later stages.

It is a well-established fact, that systemic treatment after surgery reduces the risk of disease relapse and death in patients with primary operable cancer. However, there still are a great number of patients who do not benefit from systemic therapy.

Prognostic factors in lung cancer include presence or absence of pulmonary symptoms, tumor size, cell type (histology), degree of spread (stage) and metastases to multiple lymph nodes, and vascular invasion.

There are only few data addressing the molecular prediction of response to therapy in lung cancer. Endocrine therapies have not been considered for early treatment of lung cancer so far mostly for several reasons: lung cancer is not a gynecologic tumor site, estrogens do not play a major role in lung development, significant (initial) response to chemotherapy and lack of stratification marker for endocrine therapies. This is in part due to the fact that the determination of hormone receptors and particularly ESR1 by immunohistochemistry failed to have prognostic value for lung cancer, while ESR2 determined on protein level may have some relevance in the comparatively small group of EGFR mutated tumors (Nose N, Sugio K, Oyama T, Nozoe T, Uramoto H, Iwata T, Onitsuka T, Yasumoto K.: Association between estrogen receptor-beta expression and epidermal growth factor receptor mutation in the postoperative prognosis of adenocarcinoma of the lung. J Clin Oncol. 2009 Jan. 20; 27 (3): 411-7. Epub 2008 Dec. 8.).

This all is in sharp contrast to breast cancer, where the role of ESR1 mRNA and ER protein expression is well established as a stratification marker for endocrine treatment options.

In sharp contrast to, e.g., Nose, et al. (2009), who have not found any prognostic role of ER protein expression in 447 resected primary lung adenocarcinoma, we have surprisingly found significant results obtained by using the RNA extraction and target gene determination approach described below.

Markers predicting tumor response can function as sensitive short-term surrogates of long term outcome. Response to primary chemotherapy is an excellent experimental model to study the efficacy of anticancer therapy in a relatively short period of time. Moreover, the molecular analysis of pre- and post-chemotherapy tumor specimen enables the identification of chemotherapy resistant tumor cell subpopulation and thereby leads to adapted treatment options. However the identification of relevant resistance mechanisms in such settings and development of tests that could be used to detect these underlying resistance mechanisms for patient selection before therapy in clinical routine tissue have not succeeded so far. The use of such markers can make therapeutic strategies more effective for the individual patient and will allow changing regimen early in the case of non-responding tumors. Moreover, the identification of such markers has the potential to identify new drug targets and develop new and more effective treatments.

Lung cancer is commonly treated by chemotherapy, radiotherapy, or surgery with adjuvant chemotherapy. While hormonal therapies are commonly used in the treatment of endocrine organ-associated malignancies such as breast and prostate cancer, at present they are not indicated for lung cancer cases.

Ovarian cancer is the most lethal gynecologic cancer with 20,000 new cases per year and 15,000 deaths per year in the US (5 year overall survival: Stage I 80%, Stage IV 20%) in part due to the fact that most cases are detected in the late stages III and IV). Chemotherapy is standard of care for early and advanced ovarian cancer, while endocrine therapy is given only after failure of chemotherapy regimens. Response to chemotherapy is comparatively low with about 10%-30% of patients having benefit from treatment, while having serious side effects and being costly for the national health systems. Despite prominent responses towards chemotherapy, the survival of particularly ovarian cancer patients is still very poor. To date there are no reliable response markers to predict response to chemotherapy or endocrine therapy in ovarian cancer based on immunohistochemistry, FISH or expression profiling analysis. However, there are only few data addressing the molecular prediction of response to therapy in ovarian cancer.

Prostate cancer is the most frequent male cancer with approximately 190,000 new cases per year in the United States. However, in contrast to the situation in lung and ovarian cancer, most tumors are identified in an early and yet good prognostic stage. Compared to the high incidence rate the annual death rate is therefore comparably low with approximately 30,000 deaths. For most prostate cancer patients "watchful waiting", i.e., sparing patients surgery, radiation and systemic treatment would be the most appropriate way to treat prostate cancer patients, as the individual risk of distant metastasis and death is very low (="progression risk"). This is of particular importance given the higher age and comorbidities of prostate cancer patients. Moreover, therapeutic approaches to treat prostate cancer all bear a high risk of developing significant and persistent side effects, such as incontinence and impotence in about 80% of the cases. However, there are no reliable markers that might be useful to reliably identify patients of low progression risk and be useful for tailored treatment approaches. A particular problem is the high heterogeneity and dispersed growth of prostate cancer. Biopsying and subsequent tissue analysis is therefore only of limited efficacy and prognostic value.

Despite state of the art chemo- and endocrine therapy, more than 15% of all breast cancer patients metastasize early and die within the first three to five years after initial surgery. Multiple studies have demonstrated that adjuvant therapy for early-stage breast cancer produces a 23% or greater improvement in disease-free survival and a 15% or greater increase in overall survival rates. However, 30% of breast cancer patients suffer from recurring disease even after harsh chemotherapeutic and endocrine treatment and 15% of the patients die within four years after primary surgery.

In general, all patients of a given cohort do receive the same treatment, even though many will fail in treatment success. Markers predicting tumor response can function as sensitive short-term surrogates of long-term outcome. The use of such markers can make chemotherapy more effective for the individual patient and will allow changing regimen early in the case of non-responding tumors.

Although much effort has been devoted in developing an optimal clinical treatment course for individual patients with cancer, very little progress has been made in predicting the individual's response to a certain treatment. Currently, the probability of response of patients to a certain cancer treatment is usually determined by measuring the status of a marker on protein-level by immunohistochemistry (IHC). Assays based on protein-level measurements exhibit only limited quantitative performance and comparatively high inter- and intra-assay variabilities. Especially immunohistochemistry often yields different results in different laboratories. IHC assays have the added drawback that they often need to be evaluated by trained pathologists or other personnel, thus adding a subjective component to the determination of assay results.

Other approaches, as FISH (Fluorescence In Situ Hybridization) or expression profiling analysis, suffer of drawbacks as low sensitivity, restriction of sample preparation and restricted multiplexing capabilities.

Chemotherapy is standard of care for early and advanced lung cancer, while endocrine therapies have not been tested in this cancer indication. To date there are no reliable response markers to predict response to chemotherapy or endocrine therapy in lung cancer based on immunohistochem-istry, FISH or expression profiling analysis. So, it is yet difficult to determine those patients suffering of lung cancer who will respond to a certain therapy.

Similarly, in ovarian cancer endocrine therapies have not been tested in early treatment stages. Lack of reliable response markers and failure of immunohistochemical methods to determine the prognostic value of hormone receptors has corrupted these developments. In contrast in breast and prostate cancer the endocrine treatment options are standard of care as being one of the most effective treatment options. Here, the reasons for failure of endocrine treatment, is still not well understood.

The present invention surprisingly opens a new approach to diagnostic assessment of cancer and also suggests the possibility of endocrine therapy for cancer patients. Moreover it enables a new kind of cancer tumor classification into the principle underlying biological activities and therefore a general risk categorization resembling to some extent the current situation in breast cancer.

BASIS OF THE INVENTION

In several cancer diseases, the determination of hormone receptors by immunohistochemistry so far has failed to have prognostic value. Surprisingly, even in cancers that have been recalcitrant to hormone-based therapies thus far, the inventor of the present invention has found methods by which the determination of hormone receptor status can have prognostic significance.

The significance of hormone receptor status in cancers of the female breast or reproductive organs, including uterus, ovaries, cervix, fallopian tubes, vulva, vagina, prostate and testes, is well known. In some of these cancers, e.g., breast cancer, the determination of hormone receptor status is standard medical practice. Lung tissues, however, unlike tissues of the reproductive organs, are not generally known to be growth regulated by steroid hormones. It is particularly surprising and unexpected that hormone receptor status should have a prognostic value in such types of cancer.

Moreover, it is new that hormone receptor status of female cancer patients determined according to said methods should be taken into account, when intending to administrate hormone replacement therapy (HRT) to peri- or postmenopausal women. Here, elevated hormone receptor levels, such as, e.g., estrogen receptor ESR1, and/or low levels of snail factors, such as, e.g., SNAI2, indicate not to administer hormones, as this could force aggressiveness and progression of an otherwise comparably less harmful or low risk tumor.

Determining the expression levels of hormone receptors and counteracting transcription factors involved in epithelial-mesenchymal-transition ("EMT"), that directly and negatively affect the hormone receptor expression level, improves said method with regard to higher robustness and lower technical complexity. By generating a two gene ratio between hormone receptors (e.g., ESR1) and EMT-transcription factors (e.g., SNAIL2), the hormone receptor status becomes more precise and robust. Surprisingly this two gene ratio not only performed in lung cancer, but also in ovarian, prostate and breast cancer, indicating that the balance between hormone receptors and EMT markers is generally critical with regard to survival and response to treatment in cancer.

BRIEF DESCRIPTION OF THE DRAWINGS

FIGS. 8-16: SEQ ID NOs 1-9, respectively.

DEFINITIONS

Figure 1:
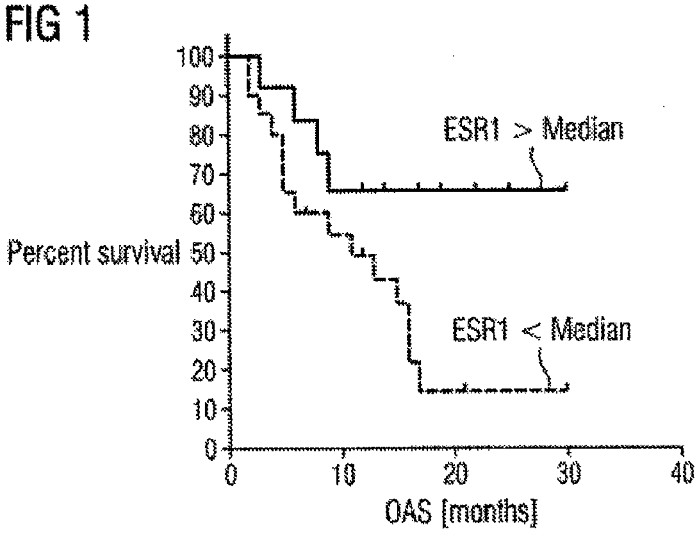
FIG. 1: Kaplan-Meier-Analysis of overall survival (OAS) of patients suffering from lung cancer based on i ESR1 (ER) determination. The overall survival (OAS) is depicted in months. Patients are stratified according to ESR1 expression above or below the median ESR1 expression.

Unless defined otherwise, technical and scientific terms used herein have the same meaning as commonly understood by one of ordinary skill in the art to which this invention belongs.

The term "prediction" as used herein relates to the likelihood that a patient will respond either favorably or unfavorably to a given therapy. Especially, the term "prediction", as used herein, relates to an individual assessment of the malignancy of a tumor, or to the expected survival rate (DFS, disease free survival) of a patient, if the tumor is treated with a given therapy. In contrast thereto, the term "prognosis" relates to an individual assessment of the malignancy of a tumor, or to the expected survival rate (DFS, disease free survival) of a patient, if the tumor remains untreated.

The term "predicting an outcome" of a disease, as used herein, is meant to include both a prediction of an outcome of a patient undergoing a given therapy and a prognosis of a patient who is not treated. The term "predicting an outcome" may, in particular, relate to the risk of a patient suffering an event, such as metastasis or death, preferably within a given time frame.

The term "classification of a sample" of a patient, as used herein, relates to the association of said sample with at least one of at least two categories. These categories may be for example "high risk" and "low risk", high, intermediate and low risk, wherein risk is the probability of a certain event occurring in a certain time period, e.g., occurrence of metastasis, disease free survival, and the like. It can further mean a category of favorable or unfavorable clinical outcome of disease, responsiveness or non-responsiveness to a given treatment or the like. Classification may be performed by use of an algorithm, in particular a discriminant function. A simple example of an algorithm is classification according to a first quantitative parameter, e.g., expression level of a gene of interest, being above or below a certain threshold value. Classification of a sample of a patient may be used to predict an outcome of disease. Instead of using the expression level of a single gene of interest, a combined score of several genes of interest may be used. Further, additional data may be used in combination with the first quantitative parameter. Such additional data may be clinical data from the patient, such as sex, age, weight of the patient, tumor grading or stage, and the like.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. For example, a patient may be classified as "high risk" or "low risk", "high probability of metastasis" or "low probability of metastasis", "in need of treatment" or "not in need of treatment" according to data obtained from said patient, sample or event. Classification is not limited to "high vs. low", but may be performed into a plurality of categories, grading or the like. Examples for discriminant functions which allow a classification include, but are not limited to discriminant functions defined by support vector machines (SVM), k-nearest neighbors (kNN), (naive) Bayes models, or piece-wise defined functions such as, for example, in subgroup discovery, in decision trees, in logical analysis of data (LAD) and the like.

The term "response marker" relates to a marker which can be used to predict the clinical response of a patient towards a given treatment. Response includes direct observation of tumor shrinkage upon neoadjuvant or palliative treatment as evident by, e.g., CT-Scans and/or serum biomarkers as well as effects on Disease Free Survival (DFS), Overall Survival (OAS), Metastasis Specific Survival (MSS), Disease Specific Survival and related assessments.

The term "clinical response" of a patient, as used herein, relates to the effectiveness of a certain therapy in a patient, meaning an improvement in any measure of patient status, including those measures ordinarily used in the art, such as overall survival, progression free survival, recurrence-free survival, and distant recurrence-free survival. Recurrence-free survival (RFS) refers to the time (in years) from surgery to the first local, regional, or distant recurrence. Distant recurrence-free survival (DFRS) refers to the time (in years) from surgery and/or initial diagnosis to the first anatomically distant recurrence. The calculation of these measures in practice may vary from study to study depending on the definition of events to be either censored or not considered. The term "response marker" relates to a marker which can be used to predict the clinical response of a patient towards a given treatment.

The term "neoplastic disease" refers to a cancerous tissue this includes carcinomas, e.g., carcinoma in situ, invasive carcinoma, metastatic carcinoma, and pre-malignant conditions, neomorphic changes independent of their histological origin. The term "adenocarcinoma" refers to a malignant tumor originating in glandular tissue. The terms "cancer" and "cancerous" refer to or describe the physiological condition in mammals that is typically characterized by unregulated cell growth. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer, primary carcinomas, and all other types of cancers, malignancies and transformations specially associated with gynecologic cancer are included. The terms "neoplastic disease" or "cancer" are not limited to any tissue or cell type they also include primary, secondary or metastatic lesions of cancer patients, and also comprise lymph nodes affected by cancer cells or minimal residual disease cells either locally deposited or freely floating throughout the patient's body.

As used herein, the term "lung cancers" refers to cancer or malignancies which are diagnosed in the lung and is meant to include all cancers, neoplastic growths and cancerous transformations of lung tissue. Examples of lung cancers include, but are not limited to: small cell lung carcinoma (SCLC), and non-small cell lung carcinoma (NSCLC), in particular squamous cell lung carcinoma, adenocarcinoma, bronchioloalveolar carcinoma, large cell lung carcinoma, and others, such as pleuropulmonary blastoma and carcinoid tumors.

The term "tumor" as used herein, refers to all neoplastic cell growth and proliferation, whether malignant or benign, and all pre-cancerous and cancerous cells and tissues.

The term "neoplastic cells" refer to abnormal cells that grow by increased cellular proliferation, altered cell division symmetry or decreased cell death mechanisms more rapidly than normal. As such, neoplastic cells of the invention may be cells of a benign neoplasm or may be cells of a malignant neoplasm.

Furthermore, the term "characterizing the state" of a neoplastic disease or cancer is related to, but not limited to, measurements and assessment of one or more of the following conditions: Type of tumor, histomorphological appearance, dependence on external signal (e.g., hormones, growth factors), invasiveness, motility, state by TNM Classification of Malignant Tumors (TNM), a cancer staging system developed and maintained by the International Union Against Cancer, or similar, aggressivity, malignancy, metastatic potential, and responsiveness to a given therapy.

The terms "therapy modality", "therapy mode", "regimen", "chemo regimen", and "therapy regimen" each refer to a timely sequential or simultaneous administration of anti-tumor, and/or anti-vascular, and/or immune stimulating, and/or blood cell proliferative agents, and/or radiation therapy, and/or hyperthermia, and/or hypothermia—any and all approaches for cancer therapy. The administration of these approaches can be performed in an adjuvant and/or neoadjuvant mode. The composition of any such "protocol" may vary in the dose of the single agent, timeframe of application and frequency of administration within a defined therapy window. Currently various combinations of various drugs and/or physical methods, and various schedules are under investigation.

The term "endocrine treatment" refers to various treatment modalities known as hormonal therapy or anti-hormonal therapy that produce the desired therapeutic effect by means of change of hormone/hormones level. The treatment may include administration of hormones or hormone analogs, synthetic hormones or other drugs to the patient, or decreasing the level of hormones in the body by using hormone antagonists, hormone receptor antagonists or hormone ablation therapy either by surgical resection of ovaries or by chemical suppression of hormone synthesis. Endocrine therapy shall be taken to include hormonal therapies such as selective estrogen reuptake inhibitors, selective estrogen receptor downregulators, aromatase inhibitors and ovarian ablation. Said endocrine treatment may include administration of hormones or hormone analogs, synthetic hormones or other drugs to the patient, e.g., tamoxifen, raloxifen and/or gosereline (tradename Zoladex®). In one embodiment, the said endocrine treatment comprises the administration of tamoxifen or of tamoxifen and gosereline. Further, said endocrine treatment may comprise the administration of an antiestrogen drug selected from the group comprising anastrozole, letrozole, exemestane, fulvestrant, toremifene and megasterol acetate. Said endocrine treatment may also comprise the administration of estrogen, progestin and/or gestagen.

The term "determining the expression level of a gene on a nonprotein basis" relates to methods which are not focused on the secondary gene translation products, i.e., proteins, but on other levels of the gene expression, based on RNA and DNA analysis. In one embodiment of this invention the analysis uses mRNA including its precursor forms. An exemplary determinable property is the amount of the estrogen receptor or progesterone receptor mRNA, i.e., of the ESR1, ESR2 and/or PGR gene. It may also include the detection of DNA amplification of the respective gene.

The term "expression level" refers, e.g., to a determined level of gene expression. The term "pattern of expression levels" refers to a determined level of gene expression compared either to a reference gene, e.g., housekeeper, or inversely regulated genes, or to a computed average expression value, e.g., in DNA-chip analyses. A pattern is not limited to the comparison of two genes but is more related to multiple comparisons of genes to reference genes or samples. A certain "pattern of expression levels" may also result and be determined by comparison and measurement of several genes disclosed hereafter and display the relative abundance of these transcripts to each other. Expression levels may also be assessed relative to expression in different tissues, e.g., expression of a gene in cancerous tissue vs. noncancerous tissue.

Alternatively, a differentially expressed gene disclosed herein may be used in methods for identifying reagents and compounds and uses of these reagents and compounds for the treatment of cancer as well as methods of treatment. The differential regulation of the gene is not limited to a specific cancer cell type or clone, but rather displays the interplay of cancer cells, muscle cells, stromal cells, connective tissue cells, other epithelial cells, fat cells, endothelial cells of blood vessels as well as cells of the immune system, e.g., lymphocytes, macrophages, killer cells.

The term "RNA expression level" refers to a determined level of the converted DNA gene sequence information into transcribed RNA, the initial unspliced RNA transcript or the mature mRNA. RNA expression can be monitored by measuring the levels of either the entire RNA of the gene or subsequences.

The term "pattern of RNA expression" refers to a determined level of RNA expression compared either to a reference RNA or to a computed average expression value. A pattern is not limited to the comparison of two RNAs but is more related to multiple comparisons of RNAs to reference RNAs or samples. A certain "pattern of expression levels" may also result and be determined by comparison and measurement of several RNAs and display the relative abundance of these transcripts to each other. A "reference pattern of expression levels", within the meaning of the invention shall be understood as being any pattern of expression levels that can be used for the comparison to another pattern of expression levels. In an embodiment of the invention, a reference pattern of expression levels is, e.g., an average pattern of expression levels observed in a group of healthy or diseased individuals, serving as a reference group.

The term "comparing the one or more expression levels(s)" expression levels" refers to the comparison of the expression levels, e.g., by arithmetical means, such as but not limited to the ratio of the expression levels of two or more genes.

The terms "sample", "biological sample", or "clinical sample", as used herein, refer to a sample obtained from a patient. The sample may be of any biological tissue or fluid. Such samples include, but are not limited to, sputum, blood, serum, plasma, blood cells (e.g., white cells), tissue, core or fine needle biopsy samples, cell-containing body fluids, free floating nucleic acids, urine, peritoneal fluid, and pleural fluid, liquor cerebrospinalis, tear fluid, or cells there from.

Biological samples may also include sections of tissues such as frozen or fixed sections taken for histological purposes or microdissected cells or extracellular parts thereof. A biological sample to be analyzed is tissue material from a neoplastic lesion taken by aspiration or punctuation, excision or by any other surgical method leading to biopsy or resected cellular material. Such a biological sample may comprise cells obtained from a patient. The cells may be found in a cell "smear" in solid tumor material, in a lavage fluid, or in a body fluid. The sample may be a processed sample, e.g., a sample, which has been frozen, fixed, embedded or the like. A sample that is usefully employed in the context of the present invention is a formaline fixed paraffin embedded (FFPE) sample. Preparation of FFPE samples are standard medical practice and these samples can be conserved for long periods of time.

By "array" is meant an arrangement of addressable locations or "addresses" on a device. The locations can be arranged in two dimensional arrays, three dimensional arrays, or other matrix formats. The number of locations can range from several to at least hundreds of thousands. Most importantly, each location represents an independent reaction site. Arrays include but are not limited to nucleic acid arrays, protein arrays and antibody arrays. A "nucleic acid array" refers to an array containing nucleic acid probes, such as oligonucleotides, polynucleotides or larger portions of genes. The nucleic acid on the array can be rendered single stranded. Arrays wherein the probes are oligonucleotides are referred to as "oligonucleotide arrays" or "oligonucleotide chips." A "microarray," herein also refers to a "biochip" or "biological chip", an array of regions having a density of discrete regions of at least about 100/cm, and can be usefully employed as well having at least about 1000/cm, as well-understood by those skilled in the art. The regions in a microarray have typical dimensions, e.g., diameters, in the range of between about 10-250 μm, and are separated from other regions in the array by about the same distance.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides can be single-stranded DNA probe oligonucleotides. Moreover, in context of applicable detection methodologies, the term "oligonucleotide" also refers to nucleotide analogues such as PNAs and morpholinos.

The terms "modulated" or "modulation" or "regulated" or "regulation" and "differentially regulated" as used herein refer to both upregulation, i.e., activation or stimulation, e.g., by agonizing or potentiating, and down regulation, i.e., inhibition or suppression, e.g., by antagonizing, decreasing or inhibiting.

The terms "primer", "amplification primer", "probes" and "labeled probes", within the meaning of the invention, shall have the ordinary meaning of each term as is well known to the person skilled in the art of molecular biology. In the context of many embodiments of the present invention, these terms shall be understood as being polynucleotide molecules having a sequence identical, complementary, homologous, or homologous to the complement of regions of a target polynucleotide which is to be detected or quantified. In yet another embodiment, nucleotide analogues are also comprised for usage as primers and/or probes. Probe technologies used for kinetic or real time PCR applications include, e.g., PCR systems generally, such as TaqMan® systems obtainable at Roche Molecular Diagnostics, extension probes such as Scorpion® Primers, Dual Hybridisation Probes, Amplifluor® obtainable at Chemicon International, Inc, or Minor Groove Binders. Probes can be surface bound, either on a chip or on beads, and then be used as a microarray.

The phrase "response", "therapeutic success", or "response to therapy" refers in the neoadjuvant, adjuvant and palliative chemotherapeutic setting to the observation of a defined tumor free or recurrence free or progression free survival time (e.g., two years, four years, five years, ten years). This time period of disease-free, recurrence-free or progression-free survival may vary among the different tumor entities but is sufficiently longer than the average time period in which most of the recurrences appear. In a neoadjuvant and palliative therapy modality, response may additionally be monitored by measurement of tumor shrinkage and regression due to apoptosis and necrosis of the tumor mass or reduced blood supply due to altered angiogenic events.

The term "recurrence" or "recurrent disease" includes distant metastasis that can appear even many years after the initial diagnosis and therapy of a tumor, or local events such as infiltration of tumor cells into regional lymph nodes, or occurrence of tumor cells at the same site and organ of origin within an appropriate time.

"Prediction of recurrence" or "prediction of therapeutic success" does refer to the methods described in this invention, wherein a tumor specimen is analyzed for, e.g., its gene expression, genomic status and/or histopathological parameters (such as TNM and Grade) and/or imaging data and furthermore classified based on correlation of the expression pattern to known ones from reference samples. This classification may either result in the statement that such given tumor will develop recurrence and therefore is considered as a "non-responding" tumor to the given therapy, or may result in a classification as a tumor with a prolonged disease free post therapy time.

The term "marker" or "biomarker" refers to a biological molecule, e.g., a nucleic acid, peptide, protein, hormone, etc., whose presence or concentration can be detected and correlated with a known condition, such as a disease state or a combination of these, e.g., by a mathematical algorithm.

The term "marker gene" as used herein, refers to a differentially expressed gene whose expression pattern may be utilized as part of a predictive, prognostic or diagnostic process in malignant neoplasia or cancer evaluation, or which, alternatively, may be used in methods for identifying compounds useful for the treatment or prevention of malignant neoplasia and gynecological cancer in particular. A marker gene may also have the characteristics of a target gene.

"Target gene", as used herein, refers to a differentially expressed gene involved in cancer, e.g., lung cancer, in a manner in which modulation of the level of the target gene expression or of the target gene product activity may act to ameliorate symptoms of malignant neoplasia. A target gene may also have the characteristics of a marker gene.

The term "receptor", as used herein, relates to a protein on the cell membrane or within the cytoplasm or cell nucleus that binds to a specific molecule (a ligand), such as a neurotransmitter, hormone, or other substance, especially a hormone as estrogen, and initiates the cellular response. Ligand-induced changes in the behavior of receptor proteins result in physiological changes that constitute the biological actions of the ligands.

The term "signaling pathway" is related to any intra- or intercellular process by which cells converts one kind of signal or stimulus into another, most often involving ordered sequences of biochemical reactions out- and inside the cell, that are carried out by enzymes and linked through hormones and growth factors (intercellular), as well as second messengers (intracellular), the latter resulting in what is thought of as a "second messenger pathway". In many signaling pathways, the number of proteins and other molecules participating in these events increases as the process emanates from the initial stimulus, resulting in a "signal cascade" and often results in a relatively small stimulus eliciting a large response. In particular, the term "signaling pathways" relates to processes located upstream or downstream of a hormone receptor, e.g., a ligand binding said receptor, or an intracellular signaling cascade activated by said receptor.

The term "small molecule", as used herein, is meant to refer to a compound which has a molecular weight of less than about 5 kD; not uncommonly, the small molecule employed in the context of the present invention is less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids.

The term "hybridization based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods". Yet another hybridization based method is PCR, which is described below. When it comes to the determination of expression levels, hybridization based methods may for example be used to determine the amount of mRNA for a given gene.

The term "a PCR based method" as used herein refers to methods comprising a polymerase chain reaction (PCR). This is an approach for exponentially amplifying nucleic acids, like DNA or RNA, via enzymatic replication, without using a living organism. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). The term "PCR based method" comprises both end-point PCR applications as well as kinetic/real time PCR techniques applying special fluorophors or intercalating dyes which emit fluorescent signals as a function of amplified target and allow monitoring and quantification of the target. Quantification methods could be either absolute by external standard curves or relative to a comparative internal standard.

The term "method based on the electrochemical detection of molecules" relates to methods which make use of an electrode system to which molecules, particularly biomolecules like proteins, nucleic acids, antigens, antibodies and the like, bind under creation of a detectable signal. Such methods are for example disclosed in WO0242759, WO0241992 and WO02097413 filed by the applicant of the present invention, the content of which is incorporated by reference herein. These detectors comprise a substrate with a planar surface which is formed, for example, by the crystallo-graphic surface of a silicon chip, and electrical detectors which may adopt, for example, the shape of inter digital electrodes or a two dimensional electrode array. These electrodes carry probe molecules, e.g., nucleic acid probes, capable of binding specifically to target molecules, e.g., target nucleic acid molecules. The probe molecules are for example immobilized by a Thiol-Gold-binding. For this purpose, the probe is modified at its 5'- or 3'-end with a thiol group which binds to the electrode comprising a gold surface. These target nucleic acid molecules may carry, for example, an enzyme label, like horseradish peroxidase (HRP) or alkaline phosphatase. After the target molecules have bound to the probes, a substrate is then added (e.g., α-naphthyl phosphate or 3.3'5.5'-tetramethylbenzidine which is converted by said enzyme, particularly in a redox-reaction. The product of said reaction, or a current generated in said reaction due to an exchange of electrons, can then be detected with help of the electrical detector in a site specific manner.

The term "nucleic acid molecule" is intended to indicate any single- or double stranded nucleic acid and/or analogous molecules comprising DNA, cDNA and/or genomic DNA, RNA, such as, for example, mRNA, peptide nucleic acid (PNA), locked nucleic acid (LNA) and/or Morpholino.

The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for longer probes. Stringent conditions may also be achieved with the addition of destabilizing agents, such as formamide and the like.

The term "fragment of the nucleic acid molecule" is intended to indicate a nucleic acid comprising a subset of a nucleic acid molecule according to one of the claimed sequences. The same is applicable to the term "fraction of the nucleic acid molecule".

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "derivative" as used herein, refers to a nucleic acid molecule that has similar binding characteristics to a target nucleic acid sequence as a nucleic acid molecule according to one of the claimed sequences The term "hybridizing counterparts" as used herein, refers to a nucleic acid molecule that is capable of hybridizing to a nucleic acid molecules under stringent conditions.

The term "anamnesis" relates to patient data gained by a physician or other healthcare professional by asking specific questions, either of the patient or of other people who know the person and can give suitable information (in this case, it is sometimes called heteroanamnesis), with the aim of obtaining information useful in formulating a diagnosis and providing medical care to the patient.

This kind of information is called the symptoms, in contrast with clinical signs, which are ascertained by direct examination.

The term "etiopathology" relates to the course of a disease, that is its duration, its clinical symptoms, and its outcome.

As used herein, the term "repair mechanisms related therewith" refers to cellular repair enzymes the expression of which correlates with the expression of at least one of said hormone receptors selected from the group comprising estrogen receptor, progesterone receptor and/or androgen receptor. A low ratio of hormone receptor versus EMT marker is generally correlated to an unfavorable outcome. Further, an decreased or downregulated expression of said hormone receptor indicates that the patient has lower PARP1 expression levels and higher angiogenic activities and therefore benefit from a specific mode of therapy, in particular treatments comprising targeting repair mechanisms and angiogenic activities selected from the group comprising PARP1, VEGFRs, PDGFRs, and/or their ligands and/or their respective signaling pathways.

OBJECT OF THE INVENTION

It is one object of the present invention to provide biological markers allowing one skilled in the medical arts to predict outcome of cancer patients by providing prognostic and/or predictive information concerning the therapeutic outcome of a given treatment including surgery, systemic and/or local application of chemotherapeutic and/or endocrine agents as well as antibody based, nucleic acid based and/or small molecule based strategies.

It is another object of the present invention to provide a method for predicting a clinical response of cancer to a given treatment based on tissue analysis before, during or after therapy.

These objects are met with the methods and means according to the independent claims of the present invention.

SUMMARY OF THE INVENTION

Before the invention is described in detail, it is to be understood that this invention is not limited to the particular component parts of the process steps of the methods described as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

In its most general term, the invention relates to a method of classifying a sample of a patient who suffers from or is at risk of developing cancer, said method comprising the steps of determining in said sample from said patient, on a non-protein basis, the expression level of at least one gene in said sample encoding for a hormone receptor selected from the group consisting of an estrogen receptor, a progesterone receptor, and an androgen receptor, comparing the one or more expression level(s) determined with one or more expression level(s) of one or more reference genes and thereby forming a pattern of expression level(s); and classifying the sample of said patient from the outcome of the comparison into one of at least two classifications.

The method thus allows predicting a clinical response towards a given mode of treatment. An increased or upregulated expression of said hormone receptor is generally correlated to a favorable outcome. Further, an increased or upregulated expression of said hormone receptor indicates that the patient can benefit from a specific mode of therapy, in particular a treatment targeting at least one hormone receptor selected from the group comprising estrogen receptor, progesterone receptor and/or androgen receptor, or targeting their respective signaling pathways, and/or a treatment targeting repair mechanisms related therewith.

As used herein, the term "signaling pathways" relates to processes located upstream or downstream of the said receptor, e.g., a ligand binding said receptor, or an intracellular signaling cascade activated by said receptor.

In a more specific term, the invention relates to a method of predicting an outcome of disease in a patient suffering from cancer wherein the expression level of at least one gene encoding for a hormone receptor selected from the group consisting of an estrogen receptor, a progesterone receptor, and an androgen receptor is determined on a nonprotein basis and one gene selected from the group of Epithelial-Mesenchymal-Transition factors comprising SNAI1, SNAI2 and/or SNAI3. The expression levels are set into a ratio thereby abrogating the need of housekeeping or reference genes. This enables single well detection of all relevant genes by multiplexing and eliminates problems arising from variations (pipetting, enzyme reaction, fluorescence scanning, etc.). Moreover, it lowers costs and increases throughput of the diagnostic workflow with finite resources (sample amount, reagent costs, capacity utilization). A high ratio of hormone receptor versus EMT marker is generally correlated to a favorable outcome. Further, an increased or upregulated expression of said hormone receptor indicates that the patient can benefit from a specific mode of therapy, in particular treatment comprising targeting hormone receptors selected from the group comprising estrogen receptor, progesterone receptor and/or androgen receptor or targeting the respective hormones and/or their respective signaling pathways.

As used herein, the term "repair mechanisms related therewith" refers to cellular repair enzymes the expression of which correlates with the expression of at least one of said hormone receptors selected from the group comprising estrogen receptor, progesterone receptor and/or androgen receptor. A low ratio of hormone receptor versus EMT marker is generally correlated to an unfavorable outcome. Further, an decreased or downregulated expression of said hormone receptor indicates that the patient has lower PARP1 expression levels and higher angiogenic activities and therefore benefit from a specific mode of therapy, in particular treatments comprising targeting repair mechanisms and angiogenic activities selected from the group comprising PARP1, VEGFRs, PDGFRs, and/or their ligands and/or their respective signaling pathways.

By way of illustration and not by way of limitation said signaling activities comprise receptor tyrosine kinase signaling, e.g., via epidermal growth factor receptor (EGFR) family members, vascular endothelial growth factor receptor (VEGFR) signaling, Fibroblast Growth Factor Receptor (FGFR) family members, Platelet Derived Growth Factor Receptor (PDGFR) family members, c-KIT, a proto-oncogene encoding a receptor tyrosine kinase, or Mesenchymal epithelial transition factor (c-Met); WNT signaling; Notch signaling; Hedgehog signaling; Transforming growth factor-beta (TGF-beta)/SMAD signaling and nuclear factor-kappa B (NFkB) signaling.

In particular, the invention relates to the method and kit specified in the claims. As specific embodiments of the invention, herein disclosed are the invention according to the following embodiments:

A first aspect of the invention is directed to a method of classifying a sample of a patient suffering from or at risk of developing a lung cancer, said method comprising the steps of:

a. determining in said sample from said patient, on a non protein basis, the expression level of at least one gene encoding for a hormone receptor selected from the group comprising estrogen receptor, progesterone receptor and/or androgen receptor in said sample;
b. comparing the pattern of expression level(s) determined in step (a) with one or several reference pattern(s) of expression levels; and
c. classifying the sample of said patient from the outcome of the comparison in step (b) into one of at least two classifications.

A second aspect of the invention is directed to a method for predicting a clinical response of a patient suffering from or at risk of developing a lung cancer towards a given mode of treatment, said method comprising the steps of:

a. determining in a sample from said patient, on a non protein basis, the expression level of at least one gene encoding for a hormone receptor selected from the group comprising estrogen receptor, progesterone receptor and/or androgen receptor in said sample;
b. comparing the pattern of expression level(s) determined in step (a) with one or several reference pattern(s) of expression levels; and
c. predicting therapeutic success for said given mode of treatment in said patient from the outcome of the comparison in step (b).

A third aspect the invention is directed to a method of predicting a clinical response towards a given mode of cancer treatment or classifying a sample of a patient who suffers from or being at risk of developing cancer, said method comprising the steps of:

a. determining in said sample from said patient, on a non protein basis, the expression level of at least one gene encoding for a hormone receptor selected from the group comprising estrogen receptor, progesterone receptor and/or androgen receptor in said sample;
b. comparing the one or more expression level(s) determined in step (a) with one or more expression level(s) of one or more reference genes and thereby forming a pattern of expression level(s); and
c. classifying the sample of said patient from the outcome of the comparison in step (b) into one of at least two classifications.

In one embodiment, the mode of treatment based on the classification in step (c) comprises an endocrine treatment by targeting hormone receptors selected from the group comprising estrogen receptor, progesterone receptor and/or androgen receptor or their respective signaling pathways and/or a treatment targeting repair mechanisms related therewith.

In another embodiment, said endocrine treatment is a hormonal treatment and/or antihormonal treatment. In yet another embodiment, said endocrine treatment comprises the administration of tamoxifen. In another embodiment, said endocrine treatment is intended to be given as hormone replacement therapy (HRT) in peri- or postmenopausal women. In yet another embodiment, the gene encoding for the estrogen receptor is ESR1.

In another embodiment, the upregulated expression of said at least one gene encoding for a hormone receptor selected from the group comprising estrogen receptor, progesterone receptor and/or androgen receptor determined in step (a) is indicative of a promising prediction as regards therapeutic success for said given mode of treatment.

In yet another embodiment, it is an intermediate upregulated expression of said at least one gene encoding for a hormone receptor selected from the group comprising estrogen receptor, progesterone receptor and/or androgen receptor determined in step (b) which is indicative of a promising prediction as regards therapeutic success for a therapeutic regimen targeting hormone receptors selected from the group comprising estrogen receptor, progesterone receptor and/or androgen receptor. In an embodiment, said one or more reference gene(s) is at least one housekeeping gene and/or at least one EMT marker gene.

In another embodiment, the at least one housekeeping gene is selected from the group comprising RPL37A, GAPDH, RPL13 and/or HPRT1; and the at least one EMT marker gene is selected from the group comprising SNAI1, SNAI2 and/or SNAI3.

In another embodiment, the comparison in step (b) of the method is a two gene ratio between the expression level of a hormone receptor and an EMT marker gene, such as, for example, a ratio of ESR1 to SNAI2.

In another embodiment, said given mode of treatment acts on recruitment of lymphatic vessels, angiogenesis, cell proliferation, cell survival and/or cell motility, and/or comprises administration of a chemotherapeutic agent.

In a further embodiment said given mode of treatment is selected from the group comprising chemotherapy, administration of small molecule inhibitors, antibody based regimen, anti-proliferation regimen, pro-apoptotic regimen, pro-differentiation regimen, radiation and/or surgical therapy.

The invention is also directed to a method of selecting a therapy modality for a patient afflicted with a lung cancer, said method comprising the steps of:

a. predicting from a biological sample from said patient, by the method according to any one of the aforementioned numbered paragraphs, therapeutic success for a plurality of individual modes of treatment; and
b. selecting a mode of treatment which is predicted to be successful in step (a).

And the invention is further directed to a method for adapting therapeutic regimen based on individualized risk assessment for a patient suffering from or at risk of developing a lung cancer, comprising the steps of:

a. determining in a biological sample from said patient, on a non protein basis, the expression level of at least one gene encoding for a hormone receptor selected from the group comprising estrogen receptor, progesterone receptor and/or androgen receptor in said sample;

b. comparing the pattern of expression level(s) determined in step (a) with one or several reference pattern(s) of expression levels; and c. implementing therapeutic regimen targeting hormone receptors selected from the group comprising estrogen receptor, progesterone receptor and/or androgen receptor or signaling pathways in said patient from the outcome of the comparison in step (b).

In a number of the recited embodiments, said expression level(s) is determined by a. a hybridization based method;

b. a PCR based method;

c. a method based on the electrochemical detection of particular molecules, and/or d. an array based method.

In another embodiment said expression level is determined by reverse transcriptase polymerase chain reaction of RNA transcripts.

In yet another embodiment said expression level is determined in formalin and/or paraffin fixed tissue samples of the RNA transcripts.

In a further embodiment, the sample is treated with silica-coated magnetic particles and a chaotropic salt, for purification of the nucleic acids contained in said sample prior to the determination in step (a).

In another embodiment, the upregulated expression level of said at least one gene encoding for a hormone receptor selected from the group comprising estrogen receptor, progesterone receptor and/or androgen receptor is related to a favorable outcome, in particular to prolonged survival.

In yet another embodiment, said cancer displays characteristics of or is an adenocarcinoma.

It yet another embodiment, it could also be a non-carcinogen neoplastic disease. In another embodiment, the cancer is selected from the group consisting of a lung cancer, a non-small cell lung cancer (NSCLC), an ovarian cancer, a breast cancer, and a prostate cancer.

In another embodiment, the pattern of expression level(s) determined in step (a) is correlated with said patient's data, said data being selected from the group consisting of etiopathology data, clinical symptoms, anamnesis data and/or data concerning the therapeutic regimen.

The invention is further directed to a kit useful for carrying out a method of any one of the aforementioned numbered paragraphs, comprising at least a pair of gene specific primers and/or probes each having a sequence sufficiently complementary to at least one gene or gene fragments or genomic nucleic acid sequence encoding for a at least one gene coding for a hormone receptor selected from the group comprising estrogen receptor, progesterone receptor and/or androgen receptor for quantifying the expression of said at least one gene or gene fragment or genomic nucleic acid sequence, and/or their fractions, variants, homologues, derivatives, fragments, complements, hybridizing counterparts, or molecules sharing a sequence identity of at least about 70%, of at least about 75%, of at least about 80%, of at least about 85%, of at least about 90%, of at least about 95%, of at least about 97%.

It is again pointed out that all details of the methods and kits described are not limited to their application in lung cancer but also to other types of cancer. Thus, lung cancer is only the example of choice. Up to now the prognostic and predictive role of hormone receptors in lung cancer selected from the group comprising estrogen receptor (ESR), progesterone receptor (PGR) and/or androgen receptor (AR) in lung cancer has not been shown. Accordingly no endocrine treatment options are offered to lung cancer patients in the neoadjuvant or adjuvant setting.

The hormone receptor RNA expression of ESR1, ESR2, PGR, AR in fresh and fixed tissue biopsy samples and tumor resectates of stage III and IV small cell and non-small cell lung cancer patients from a non-stratified, population based cohort treated with chemotherapy were analyzed.

Surprisingly, it was found that the expression level of a gene encoding for a hormone receptor selected from the group comprising estrogen receptor, progesterone receptor and/or androgen receptor has prognostic and/or predictive value in lung cancer.

In this regard it is to be understood, that the analysis of estrogen receptor and progesterone receptor status on protein basis has turned out to be inferior to the detection of genes coding for estrogen receptor on RNA basis, as the determination of estrogen receptor by immune histochemistry fails to have prognostic value for lung cancer. This has been experimentally confirmed by the inventors in a very same cohort of patients, where the diagnostic value of estrogen and/or progesterone receptor expression determination by kinetic PCR (kPCR) methods has been proven.

The validity of these findings have been shown by independent measurements of fresh tissue biopsies and resectates by array analysis and also by PCR based analysis of clinical routine material, i.e., formalin fixed and paraffin embedded (=FFPE) tissues.

Moreover, it was established, for the first time, to use the expression level of a gene encoding for hormone receptors selected from the group comprising estrogen receptor, progesterone receptor and/or androgen receptor for the decision whether a given therapy is the most promising therapy for the respective patient having lung cancer or if treatment modalities should be altered. In particular, the method disclosed herein is highly prognostic in the identical samples of a patient cohort where the state of the art technology, i.e., immunohistochemistry (=IHC), clearly fails to have any prognostic information.

The prediction of therapeutic success or the investigation of the response to a treatment can be performed at time of first biopsy or after surgery, at a stage in which other methods cannot provide the required information on the patient's response to chemotherapy. Hence the current invention also provides means to decide even shortly after tumor surgery whether or not a certain mode of chemo-therapy is likely to be beneficial to the patient's health and/or whether to maintain or change the applied mode of chemotherapy treatment. This is of particular importance as the decision which systemic therapy to apply first is of outmost importance for survival, development of resistance and therefore also for subsequent treatment strategies. Also the overall status of patients is usually best at initial diagnosis and therefore allows to apply more complex and/or aggressive treatment options at intended. This not only holds true for chemotherapeutic strategies but is also of importance for generally less toxic strategies, such as anti-angiogenic treatments as exemplified by application of Bevacizumab (tradename Avastin®), Sunitinib (tradename Sutent®) or Sorafenib (tradename Nexavar®). The reason for this is in part the extensive surgery being necessary for lung cancer, which inter alias increases the risk of bleeding and intraoperative or postoperative death.

According to the superiority of non-protein based determination of hormone receptor status selected from the group comprising estrogen receptor, progesterone receptor and/or androgen receptor status, the method should substitute currently available measurements, or used in addition to currently available tests or histopathological parameter to make diagnosis more accurate.

Furthermore, the method according to the invention may be applied in neoadjuvant, adjuvant and metastatic settings. Importantly, the inventors have found that hormone receptors such as estrogen, progesterone and/or androgen receptor are useful for prediction based on untreated tumor samples but also prognostic for treated tumor samples.

The inventor suggests, for the first time, to use the expression level of at least one gene encoding for estrogen receptor for the decision whether a therapeutic regimen targeting a hormone receptor, e.g., estrogen receptor, in other words, an endocrine therapy, could be beneficial in a lung cancer patient. This particularly not only comprises different kinds of hormone antagonists or enzyme inhibitors blocking steps of the estrogen biosynthesis but also the usage of hormone agonists, e.g., estrogen, as this could accelerate hormonal control of deregulated cancer cell activities and/or sensitize towards other therapeutic options such as chemotherapy.

It is yet another embodiment of the invention to combine the information of the mRNA expression level of at least one gene encoding for hormone receptors such as estrogen, progesterone and/or androgen receptor with the level of microRNAs regulating the stability and/or translation of respective mRNAs. By way of illustration and not by way of limitation this may mean that tumors expressing intermediate levels of ESR1 mRNA do worse, when higher levels of microRNAs downregulate ESR1 protein expression, compared to tumors expressing intermediate levels of ESR1 mRNA that do not display microRNA expression of respective microRNAs.

It is yet another embodiment of the invention to combine the information of the mRNA expression level of at least one gene encoding for hormone receptors such as estrogen, progesterone and/or androgen receptor with the expression level of CYP19A1, which is responsible for the conversion of androgens to estrogens is expressed not only in gonads and adrenals but also in many other tissues, including normal lungs and lung cancers and therefore produces hormone receptor ligands in proximity to the neoplastic tissue. This contributes to the finding being part of this invention, that the determination of hormone receptors is not only useful in women but also in men and therefore of diagnostic and therapeutic importance in both genders.

It is yet another embodiment of the present invention to provide a method for predicting the development of resistance to therapeutic intervention of a patient suffering from lung cancer to a given treatment.

In this context it is of note that it is part of this invention to use the described method to stratify patients, which may benefit from hormonal treatments.

It is yet another embodiment that it is part of this invention to use the described method to stratify patients, which may benefit from PARP Inhibition.

Another embodiment of the present invention provides a method to stratify patients for systemic treatments other than chemotherapy in a neoadjuvant, adjuvant or palliative setting. In one embodiment, these alternative treatment options comprise antibody based or small molecule based treatment. Notably, treatment in the context of the present invention includes endocrine treatment options.

Moreover, the method according to the invention may help to detect those tumors which are probably more susceptible to endocrine treatment than to a chemotherapeutic regimen. These tumors have so far remained undetected with methods from the state of the art. Particularly the determination of ESR1 status by IHC is not part of the current standard of care as it does not provide any prognostic information. Thereby the endocrine options have been neglected for treatment of lung cancer and ovarian cancer.

The present inventive method includes the step of assessing the expression level of at least one gene encoding for an estrogen receptor that is selected from the group consisting of ESR1, ESR2, progesterone receptor, PGR, and androgen receptor. This assessment is usefully employed in the context of the present invention for deciding whether a therapeutic regimen targeting signaling pathways, as specified above or otherwise, could be beneficial in that patient.

The inventor suggests moreover to use the expression level of at least one gene encoding for an estrogen receptor, such as, for example, one that is selected from the group consisting of ESR1, ESR2, a progesterone receptor, PGR, and an androgen receptor for the decision whether a therapeutic regimen targeting matrix metalloproteinases could be beneficial in that patient. These regimens comprise therapeutics blocking the protease activity of MMP1, MMP2, MMP7, MMP9 and/or MMP1O.

The inventor suggests moreover to use the expression level of at least one gene encoding for an estrogen receptor, such as one selected from the group consisting of ESR1, ESR2, a progesterone receptor, PGR, and an androgen receptor for the decision whether a therapeutic regimen targeting repair mechanism could be beneficial in that patient. These regimen comprise therapeutics blocking the PARP1 gene product.

The inventor suggests moreover to use the expression level of at least one gene encoding for an estrogen receptor, such as, for example, and without limitation intended, one selected from the group consisting of ESR1, ESR2, a progesterone receptor, PGR, and an androgen receptor for the decision whether a therapeutic regimen affecting bone metabolism, such as bisphosphonates, and/or antibody regimen having similar properties by attacking the RANKL system, such a denosumab, could be beneficial in that patient.

The inventor has found that the balance between hormone receptors and stem cell activities or SNAI factors is indicative of tumor outcome in lung cancer. However the inventors suggests that this balance is not limited to lung cancer but rather a general tumor principle. The present invention moreover sets forth a method to use the expression level of at least one gene encoding for an estrogen receptor, such as, for example, and without limitation intended, one selected from the group consisting of ESR1, ESR2, a progesterone receptor, PGR, and an androgen receptor for the decision whether targeted therapy such as an anti-tyrosine kinase regimen may be effective. This relates to the finding, that the absence or low activity of hormone receptors relates to more aggressive tumors characterized by, e.g., elevated EGFR family and VEGFR family activities. The inventor suggests moreover to use the expression level of at least one gene encoding for an estrogen receptor, such as one selected from the group consisting of ESR1, ESR2, a progesterone receptor, PGR, and an androgen receptor for the decision whether a tyrosine kinase inhibitor could be beneficial in a patient suffering an adenocarcinoma bearing mutated tyrosine kinase expression. The mutated tyrosine kinase in the patient that may be benefited by the present invention is EGFR of c-Met.

In one embodiment of the invention, said given mode of chemotherapy is targeted therapy such as small molecule inhibitors like Sunitinib (tradename Sutent®), Sorafenib (tradename Nexavar®), Lapatinib (tradename Tykerb®) and/ or therapeutic antibodies, e.g., Bevacizumab (tradename Avastin®) or cetuximab (tradename Erbitux®).

However, other treatments related to signaling pathways which fall under the scope of the present invention comprise the administration of BAY 43-9005, target receptors are VEGFR-2, VEGFR-3, c-KIT, PDGFR-B, RET and Raf-Kinase), BAY 57-9352 (target receptor is VEGFR-2), Sunitinib (tradename Sutent®, target receptors are VEGFR-I, VEGFR-2 and PDGFR), AG13925 (target receptors are VEGFR-I and VEGFR-2), AGO 13736 (target receptors are VEGFR-I and VEGFR-2), AZD2171 (target receptors are VEGFR-I and VEGFR-2), ZD6474 (target receptors are VEGFR-I, VEGFR-2 and VEGFR-3), PTK-787/ZK-222584 (target receptors are VEGFR-I and VEGFR-2), CEP-7055 (target receptors are VEGFR-I, VEGFR-2 and VEGFR-3), CP-547 (target receptors are VEGFR-I and VEGFR-2), CP-632 (target receptors are VEGFR-I and VEGFR-2), GW786024 (target receptors are VEGFR-I, VEGFR-2 and VEGFR-3), AMG706 (target receptors are VEGFR-I, VEGFR-2 and VEGFR-3), Imatinib mesylate (tradename Glivec®/Gleevec®, target receptors are bcr-abl and c-KIT), BMS-214662 (target enzyme is Ras farnesyl transferase), CCI-779 (target enzyme is mTOR), RADOOO1 (tradename Everolismus®, target enzyme is mTOR), CI-1040 (target enzyme is MEK), SU6668 (target receptors are VEGFR-2, PDGFR-B and FGFR-I), AZD6126, CP547632 (target receptors are VEGFRs), CP868596 GW786034 (target receptors are PDGFRs), ABT-869 (target receptors are VEGFRs and PDGFRs), AEE788 (target receptors are VEGFRs and PDGFRs), AZD0530 (target enzymes are src and abl), and CEP7055.

In another embodiment, the genes encoding for estrogen receptor are selected from the group consisting of ESR1 and ESR2. In one embodiment, the gene encoding for the estrogen receptor is ESR1.

Surprisingly, the inventors have found that the expression level of ESR1 has good prognostic and/or diagnostic value in lung cancer when tested before treatment, which resembles the de novo hormone activity of the tumor tissue. More surprisingly, the inventors have found that the benefit from chemotherapy was particularly striking in high grade and/or higher size tumors expressing estrogen and progesterone receptors, while the response of estrogen or progesterone receptor negative tumors remained to be poor. The prognostic value of hormone receptor activity was particularly prominent in NSCLC and in women suffering lung cancer, thereby contributing to the known better prognosis of the tumors in these lung cancer subgroups.

Therefore, the inventor suggests for the first time, to use the expression level of ESR1 and/or ESR2 for the decision whether a given therapy is the most promising therapy for lung cancer, or if treatment modalities should be altered. As the inventor does show by comparing with the current standard techniques, these decisions cannot be drawn with, e.g., IHC, as these techniques fail to determine the prognostic value of hormone receptors.

In another embodiment, the gene encoding for the progesterone receptor is PGR. In yet another embodiment, PGR is used for to decide on treatment modalities.

Moreover surprisingly, the inventor has found that the expression level of PGR has good prognostic and/or diagnostic value in lung cancer.

The inventor suggests for the first time, to use the expression level of PGR for the decision whether a given therapy is the most promising therapy for lung cancer or if treatment modalities should be altered.

In another embodiment, the gene encoding for the androgene receptor is AR. In yet another embodiment, AR is used for to decide on treatment modalities.

Moreover surprisingly, the inventor has found that the expression level of AR has prognostic and/or diagnostic value in lung cancer.

The inventors suggest for the first time, to use the expression level of AR for the decision whether a given therapy is the most promising therapy for lung cancer or if treatment modalities should be altered.

In another embodiment the gene encoding for the aromatase is CYP19. In yet another embodiment CYP19 is used for to decide on treatment modalities.

Moreover surprisingly, the inventors have found that the expression level of CYP19 has prognostic and/or diagnostic value in lung cancer, particularly when combined with the expression level of hormone receptors and, as one example, ESR1. The inventors suggest for the first time, to use the expression level of CYP19 and/or ESR1 for the decision whether a given therapy is the most promising therapy for lung cancer or if treatment modalities should be altered.

In another embodiment, the microRNA affecting the ESR1 expression is 206, 221 and/or 222. In yet another embodiment, microRNA is used for to decide on treatment modalities.

Moreover surprisingly, the inventor has found that the microRNA has prognostic and/or diagnostic value in lung cancer, particularly when combined with the expression level of hormone receptors and, as one useful example, ESR1.

The inventors suggest for the first time, to use the expression level of microRNA and/or ESR1 for the decision whether a given therapy is the most promising therapy for lung cancer or if treatment modalities should be altered.

Importantly, the decision when to use altered treatment modalities such as endocrine options can be influenced. These treatment modalities may be applied before, during or after chemotherapy and/or surgery.

In another embodiment of the present invention, the methods of the present invention comprise comparing the level of mRNA expression of ESR1 and/or ESR2 and/or PGR and/or AR in a patient sample, and the average level of expression of ESR1 and/or ESR2 and/or PGR and/or AR in a sample from a control subject, e.g., a human subject without cancer. Comparison of the pattern of expression levels of ESR1 and/or ESR2 and/or PGR and/or AR can also be performed on any other reference.

In another embodiment of the present invention, the methods of the present invention also comprise comparing the pattern of expression levels of mRNA of ESR1 and/or ESR2 and/or PGR and/or AR in an unclassified patient sample, and the pattern of expression levels of ESR1 and/or ESR2 and/or PGR and/or AR in a sample cohort comprising patients responding in different intensity to an administered neoadjuvant, adjuvant and/or palliative cancer therapy.

In another embodiment of this invention, the expression of ESR1 and/or ESR2 and/or PGR and/or AR can be utilized for discrimination of responders and non-responders to a given treatment, especially a chemotherapeutic and/or endocrine intervention.

In another embodiment of the present invention, it is provided that upregulated expression of said at least one gene encoding for a hormone receptor selected from the group comprising estrogen receptor, progesterone receptor and/or androgen receptor, especially of the RNA transcripts of ESR1, determined in step (b) is indicative of a promising prediction as regards therapeutic success for a given mode of treatment.

Moreover, the combined analysis of estrogen, progesterone and androgen receptors improved the diagnostic value of the single marker evaluation, i.e., just based on estrogen, progesterone or androgen receptor.

By correlation analysis, the inventors have found that overexpression of ESR1 in untreated tumor samples that are, for example, assessed by PCR analysis, is an indicator for a good prognosis of lung cancer patients treated by standard chemotherapy as indicated by prolonged disease free and overall survival. Especially a high expression of ESR1 was found to provide a good overall survival prognosis upon standard adjuvant chemotherapy. Also in the palliative chemotherapeutic setting the elevated expression level of estrogen receptors and progesterone receptors was associated with increased response to endocrine treatments. This indicates the direct link between treatment and directly related response, i.e., tumor shrinkage, whose assumption is difficult to draw in the adjuvant setting. In other embodiments, intermediate expression of ESR1, for example assessed by PCR analysis, indicates poor prognosis of lung cancer patients treated by standard chemotherapy.

In another embodiment of the present invention, it is provided that highly or intermediately upregulated expression of said at least one gene encoding for a hormone receptor selected from the group comprising estrogen receptor, progesterone receptor and/or androgen receptor determined in step (b) is indicative of a promising prediction as regards therapeutic success for a therapeutic regimen targeting hormone receptors selected from the group comprising estrogen receptor, progesterone receptor and/or androgen receptor especially endocrine treatment.

In another embodiment of the present invention, it is provided that highly or intermediately upregulated expression of said at least one gene encoding for the estrogen receptor especially ESR1 determined in step (b) is indicative of a promising prediction as regards therapeutic success for a therapeutic regimen targeting the estrogen receptor, especially endocrine treatment.

In yet another embodiment of the present invention, it is provided that highly or intermediately upregulated expression of said at least one gene encoding for the estrogen receptor especially ESR1 determined in step (b) is indicative of increased risk of bone metastasis a promising prediction as regards therapeutic success for a therapeutic regimen targeting the bone metabolism (such as bisphosphonates, denosumab).

In another embodiment of the present invention, it is provided that highly or intermediately upregulated expression of said at least one gene encoding for the estrogen receptor especially ESR1 and downregulated expression of said at least one gene encoding EMT markers especially SNAIL2 simultaneous determined in step (b) is indicative of a promising prediction as regards therapeutic success for a therapeutic regimen targeting the estrogen receptor, especially endocrine treatment.

In another embodiment of the present invention, it is provided that downregulated expression of said at least one gene encoding EMT markers especially SNAIL2 determined in step (b) is indicative of a promising prediction as regards therapeutic success for a therapeutic regimen targeting the estrogen receptor, especially endocrine treatment.

For example, in the case of highly upregulated expression of said at least one gene encoding for the estrogen receptor especially ESR1 determined in step (b) the nodal status may provide additional information with regard to outcome. In particular, if node negative the outcome of patients with high expression of, e.g., ESR1 may be very good (i.e., above 95% survival), whereas if node positive, the outcome may be inferior (i.e., at about 80% survival), while still being clearly superior to bad prognosis at low expression of, e.g., ESR1 (i.e., at 22% survival). This means that patients with tumors exhibiting high expression of, e.g., ESR1 still may have a benefit from additional endocrine treatment.

In yet another embodiment of the present invention, it is provided that low expression of said at least one gene encoding for a hormone receptor selected from the group comprising estrogen receptor, progesterone receptor and/or androgen receptor especially ESR1 indicates poor prognosis of lung cancer patients treated by standard chemotherapy.

Moreover this finding also enables to decide which patients should receive other treatment options targeting signaling pathways, e.g., small molecules.

In another embodiment of the present invention, it is provided that the pattern of expression level(s) determined in step (b) refers to a level of gene expression compared to a reference selected from the group comprising RPL37A, GAPDH, CALM2, OAZ1 RPL13, and/or HPRT1. In another embodiment these reference genes are RPL37A, GAPDH and HPRT1. In yet another embodiment, the reference genes are RPL37A and HPRT1. In another embodiment of the present invention, it is provided that said reference or housekeeping gene is RPL37A.

Normalization to a housekeeping gene selected from the group comprising RPL37A, GAPDH, RPL13, and/or HPRT1 can provide the advantage of a highly reliable comparison. In another embodiment of the present invention, it is provided that the pattern of expression level(s) determined in step (b) refers to a level of gene expression compared to an anticorrelated gene reference selected from the group comprising SNAIL1, SNAIL2, CDH11, MMP2. In an embodiment, these reference genes are SNAIL1.

In yet another embodiment of the present invention, it is provided that said given mode of treatment acts on recruitment of lymphatic vessels, angiogenesis, cell proliferation, cell survival and/or cell motility, and/or comprises administration of a chemotherapeutic agent.

Furthermore, it is provided in an another embodiment of the present invention that said given mode of treatment is selected from the group comprising chemotherapy, administration of small molecule inhibitors, antibody based regimen, anti-proliferation regimen, pro-apoptotic regimen, pro-differentiation regimen, radiation and/or surgical therapy. In yet other embodiments said given mode of treatment may include administration of cis-Platin (tradename Cisplatin®).

Said chemotherapy may comprise the administration of at least one agent selected from the group comprising Cyclophosphamid (Endoxan®, Cyclostin®). Adriamycin (Doxorubicin) (Adriblastin®), BCNU (Carmustin) (Carmubris®), Busulfan (Myleran®), Bleomycin (Bleomycin®), Carboplatin (Carboplat®), Chlorambucil (Leukeran®), Cis-Platin (Cisplatin®), Platinex (Platib-lastin®), Dacarbazin (DTIC®; Detimedac®), Docetaxel (Taxotere®), Epirubicin (Farmorubicin®), Etoposid (Vepesid®), 5-Fluorouracil (Fluroblastin®, Fluorouracil®), Gemcitabin (Gemzar®), Ifosfamid (Holoxan®), Interferon alpha (Roferon®), Irinotecan (CPT 11, Campto®), Melphalan (Alkeran®), Methotrexat (Methotrexat®, Farmitrexat®), Mitomycin C (Mitomycin®), Mitoxantron (Novantron®), Oxaliplatin (Eloxatine®), Paclitaxel (Taxol®), Prednimustin (Sterecyt®), Procarbazin (Natulan®), Pemetrexed (Alimta®), Ralitrexed (Tomudex®), Topotecan (Hycantin®), Trofosfamid (Ixoten®), Vinblastin (Velbe®), Vincristin (Vincristin®), Vindesin (Eldisine®) and/or Vinorelbin (Navelbine®).

In other embodiments said given mode of treatment may be endocrine treatment.

In a further aspect, the present invention provides a method of selecting a therapy modality for a patient afflicted with lung cancer, said method comprising the steps of:

a. obtaining a biological sample from said patient;
b. predicting from said sample, by the described before, therapeutic success for a plurality of individual modes of treatment; and
c. selecting a mode of treatment which is predicted to be successful in step (b).

It is of note, that the inventors have proven the validity of the disclosed method in fresh tissue as well as fixed tissues. Also the inventors have shown the validity of the disclosed method in biopsies as well as tumor resectates.

On the basis of the findings of the present invention a therapy can be selected, which is most promising for the individual patient.

In a further aspect, the present invention provides a method of selecting a modality for a patient afflicted with lung cancer, said method comprising the steps of:

a. obtaining a biological sample from said patient;
b. predicting from said sample, by the method described before, diagnostic success for a plurality of individual modes of imaging; and
c. selecting a mode of imaging which is predicted to be successful in step (b).

On the basis of the findings of the present invention an imaging modality can be selected, which is most promising for the individual patient.

Here the inventor has shown for the first time that high or intermediate expression of ESR1 is predictive for increased risk of bone metastasis in lung cancer patients.

Based on the ESR1, PGR, AR and or snail mRNA determination in the primary tumor the subsequent imaging modality can be chosen for more precise staging and tailored treatment choice. Higher ESR1 expression indicates a bone scan or application of labeled estrogen receptor ligands (e.g., fluoridinated estradiol "[18F]FES"). Higher PGR expression indicates a bone scan or application of labeled progesteron receptor ligands (e.g., fluoridinated progrestin. Higher AR expression indicates a bone scan or application of labeled androgen receptor ligands (e.g., fluoridinated testosterone). Higher snail expression indicates application of labeled Matrix-Metallo-Proteinase (=MMP) ligands (e.g., labeled MMP inhibitors, particularly for MMP2).

Higher risk of bone involvement in disease progression may indicate altered treatment, e.g., by including bisphosphonates or antibodies against RANKL (such as denosumab "Prolia®") to treat metastatic spread and recruitment of bone marrow derived precursor cells early on. This is thought to prevent disease progression and potentially prolong life.

In addition the inventor suggests, for the first time, to use the expression level of a gene encoding for the estrogen receptor and/or progesterone receptor, especially ESR1, for the decision whether or not chemotherapeutic treatment should be kept as treatment or if endocrine treatment or treatment options targeting signaling pathways should be included as a treatment options. In yet another addition the inventor suggests, for the first time, to use the expression level of a gene encoding for the estrogen receptor and/or progesterone receptor, especially ESR1, for the decision whether or not bone preserving treatments should be included as a therapeutic option in lung cancer.

In this regard, the accurate detection of the expression level of ESR1 enables to identify a subpopulation of tumors that overexpress ESR1 in an intermediate or slightly higher fashion, yet having a comparatively low overexpression of ESR1 that cannot be resolved by immunohistochemical techniques. This subpopulation may be particularly sensitive to endocrine treatment.

The methods of the invention maybe used to evaluate a patient before, during and after therapy, for example to evaluate the reduction in tumor burden.

In the method of the present invention the determination of gene expression or the determination of the pattern of expression level is not limited to any specific method, or to the detection of mRNA.

In the method according to the invention, said expression level determined in step (b) can be determined by a. a hybridization based method;
b. a PCR based method;
c. a method based on the electrochemical detection of particular molecules, and/or
d. an array based method.

The above mentioned methods have in common that they are focused on the detection of nucleic acids, particularly on the detection of mRNA, DNA, peptide nucleic acid (PNA), locked nucleic acid (LNA) and/or Morpholino.

Moreover, these methods provide the option that high quality determinations can be done as multiplex assays in one reaction based on the high specificity of the reagent design and performance.

Another advantage is that the method requires only small amounts of biological sample.

In yet another embodiment of the present invention, it is provided that said expression level of the RNA transcripts is determined by reverse transcriptase polymerase chain reaction (RT-PCR).

The method according to the invention has the advantage that it works on paraffin embedded tissues. In yet another embodiment of the present invention, it is provided that said expression level of the RNA transcripts is determined in formalin and/or paraffin fixed tissue samples.

For this purpose, at least one fixative may be used in an embodiment which is selected from the group consisting of Neutral Buffered Formaline, Unbuffered Formaline, Glutaraldehyde, Ethanol, Acetone, Methanol, Methacarn, Carnoy's fixative, AFA-Fixative (Formaldehyde, Ethanol and acetic acid), Pen-Fix (alcoholic formalin fixative), Glyo-Fixx (glyoxal-based fixative), Hope (Hepes-glutamic acid buffer mediated organic solvent fixative), and/or Zinc Formal-Fixx (Formaldehyde fixative which contains zinc).

In yet another embodiment of the present invention, it is provided, that the information of the method disclosed herein is combines with standard histopathological data, such as TNM status, Grade, Location, Cell Type, Inflammatory status, to improve the validity of the result and/or adopt to the clinical situation.

In yet another embodiment of the present invention, it is provided, that the results are adjusted to tumor cell content or sublocalization of the tissue material within the malignant tissue, e.g., invasive front, central oarts, angiogenic subregion, inflammatory region, etc.

Routinely, in tumor diagnosis tissue samples are taken as biopsies from a patient and undergo diagnostic procedures. For this purpose, the samples are fixed in formaline, embedded in paraffine and are then examined with immunohistochemistry methods. The formaline treatment leads to the inactivation of enzymes, as for example the ubiquitous RNA-digesting enzymes (RNAses). For this reason, the mRNA status of the tissue (the so called transcriptome), remains unaffected.

However, the formaline treatment leads to partial depolymerization of the individual mRNA molecules. Same applies for other fixatives, as for example mentioned in the above enumeration.

For this reason, it is provided in an embodiment of the present invention that after lysis, the sample is treated with silica-coated magnetic particles and a chaotropic salt, for purification of the nucleic acids contained in said sample for further determination.

However, the isolation method may alternatively also be silica column based with or without chaotropic agents.

Collaborators of the inventor of the present invention have developed an approach which however allows successful purification of mRNA out of tissue samples fixed in such manner, and which is disclosed, among others, in WO03058649, WO2006136314A1 and DE10201084A1, the content of which is incorporated herein by reference. Said method comprises the use of magnetic particles coated with silica ($SiO_2$). The silica layer is closed and tight and is characterized by having an extremely small thickness on the scale of a few nanometers. These particles are produced by an improved method that leads to a product having a closed silica layer and thus entail a highly improved purity. The said method prevents an uncontrolled formation of aggregates and clusters of silicates on the magnetite surface whereby positively influencing the additional cited properties and biological applications. The said magnetic particles exhibit an optimized magnetization and suspension behavior as well as a very advantageous run-off behavior from plastic surfaces. These highly pure magnetic particles coated with silicon dioxide are used for isolating nucleic acids, including DNA and RNA, from cell and tissue samples, the separating out from a sample matrix ensuing by means of magnetic fields. These particles are particularly well-suited for the automatic purification of nucleic acids, mostly from biological body samples for the purpose of detecting them with different amplification methods.

The selective binding of these nucleic acids to the surface of said particles is due to the affinity of negatively charged nucleic acids to silica containing media in the presence of chaotropic salts like guanidinisothiocyanate. Said binding properties are known as the so called "boom principle". They are described in the European Patent EP819696, the content of which is incorporated herein by reference.

The said approach is particularly useful for the purification of mRNA out of formaline and/or paraffine fixed tissue samples. In contrast to most other approaches, which leave very small fragments behind that are not suitable for later determination by PCR and/or hybridization technologies, the said approach creates mRNA fragments which are large enough to allow specific primer hybridization and/or specific probe hybridization. A minimal size of at least about 50 base pairs, or at least about 100 base pairs, or at least about 200 base pairs is needed for specific and robust detection of target gene expression. Moreover it is also necessary to not have too many inter-sample variations with regard to the size of the RNA fragments to guarantee comparability of gene expression results. Other issues of perturbance of expression data by sample preparation problems relate to the contamination level with DNA, which is lower compared to other bead or column based technologies.

The said approach thus allows a highly specific determination of the status of hormone receptors selected from the group comprising estrogen receptor, progesterone receptor and/or androgen receptor with one of the above introduced methods, particularly with hybridization based methods, PCR based methods and/or array based methods, even in fixed routine tissue samples, and is thus extremely beneficial in the context of the present invention, as it allows the use of tissue samples fixed with formaline and/or paraffine, which are available in tissue banks and connected to clinical databases of sufficient follow-up to allow retrospective analysis. Another important aspect is that the said approach allows the simultaneous determination of more than one analyte (multiplexing), and is thus ideally suited for the determination of hormone receptors selected from the group comprising estrogen receptor, progesterone receptor and/or androgen receptor especially ESR1, ESR2, PGR and/or of one or more housekeeping genes in said sample. Alternatively to housekeeping genes, which are per definition being expressed in virtually all cells to similar amounts, tumor specific, endothelial cell specific and or stroma specific genes may be included to further increase the diagnostic precision of said method. By this approach one can derive a calibration factor in order to normalize the expression values of the target genes in samples which have different shares of tumor tissue and nontumor tissue.

In yet another embodiment of the present invention, it is provided that said endocrine treatment is a hormonal treatment and/or antihormonal treatment.

Said endocrine treatment may comprises the administration of antagonists of estrogen binding to the estrogen receptor, estrogen reuptake inhibitors, selective estrogen receptor downregulators, or as inhibitors of estrogen biosynthesis, such as aromatase inhibitors. Said endocrine treatment may also comprise similar approaches to target progesterone and/or androgen receptors.

In yet another embodiment of the invention a method for correlating the clinical outcome of a patient suffering from or at risk of developing a lung cancer with the presence or non-presence of a defect in expression levels of the RNA transcripts of at least one gene encoding for a hormone receptor selected from the group comprising estrogen receptor, progesterone receptor and/or androgen receptor is provided, said method comprising the steps of:

a. obtaining a fixed biological sample from said patient;
b. determining the expression levels of the RNA transcripts of at least one gene encoding for a hormone receptor selected from the group comprising estrogen receptor, progesterone receptor and/or androgen receptor, and
c. correlating the pattern of expression level(s) determined in (b) with said patient's data, said data being selected from the group consisting of etiopathology data, clinical symptoms, anamnesis data and/or data concerning the therapeutic regimen.

The said method is particularly beneficial for epidemiological studies. These studies profit from the fact that large tissue databases exist comprising paraffin and/or formalin fixed tissue samples together with an extensive documentation of the patient's history, including etiopathology data, clinical symptoms, anamnesis data and/or data concerning the therapeutic regimen. The said methods advantageously allows for large scale studies.

In another embodiment of the present invention, a kit useful for carrying out a method of the invention, comprising at least a pair of gene specific primers and/or probes each having a sequence sufficiently complementary to at least one gene or gene fragments or genomic nucleic acid sequence encoding for a at least one gene coding for a hormone receptor selected from the group comprising estrogen receptor, progesterone receptor and/or androgen receptor for quantifying the expression of said at least one gene or gene fragment or genomic nucleic acid sequence, and/or their fractions, variants, homologues, derivatives, fragments, complements, hybridizing counterparts, or molecules sharing a sequence identity of at least about 70%, at least about 75%, at least about 80%, at least about 85%, at least about 90%, at least about 95%, or at least about 97%.

These nucleic acids can be used either as primers for a polymerase chain reaction protocol, or as detectable probes for monitoring the said process.

Furthermore, it is provided that the said nucleic acid or nucleic acid homologue is selected from the group consisting of DNA, RNA, PNA, LNA and/or morpholino. The nucleic acid may, in a given embodiment, be labeled with at least one detectable marker. This feature is applicable particularly for those nucleic acids which serve as detectable probes for monitoring the polymerase chain reaction process.

Such detectable markers may for example comprise at least one label selected from the group consisting of fluorescent molecules, luminescent molecules, radioactive molecules, enzymatic molecules and/or quenching molecules.

In another embodiment, the said detectable probes are labeled with a fluorescent marker at one end and a quencher of fluorescence at the opposite end of the probe. The close proximity of the reporter to the quencher prevents detection of its fluorescence; breakdown of the probe by the 5' to 3' exonuclease activity of the taq polymerase breaks the reporter-quencher proximity and thus allows unquenched emission of fluorescence, which can be detected. An increase in the product targeted by the reporter probe at each PCR cycle therefore causes a proportional increase in fluorescence due to the breakdown of the probe and release of the reporter.

The oligonucleotide in one embodiment of the invention comprises a nucleotide sequence which is a fragment, a fraction, a variant, a homologue, a derivative of, or a complementary to, any of the nucleic acid molecules set forth as SEQ ID NOs 1-9, or which is capable of hybridizing to a fragment, a fraction, a variant, a homologue, or a derivative of any of the nucleic acid molecules set forth as SEQ ID NOs 1-9.

Disclaimer

To provide a comprehensive disclosure without unduly lengthening the specification, the applicant hereby incorporates by reference each of the patents and patent applications referenced above.

The particular combinations of elements and features in the above-detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

TABLE 1

Genes of interest

| Gene_Symbol [A] | Ref. Sequences Description [A] | Ref. Sequences [A] | Unigene_ID [A] |
|---|---|---|---|
| ESR1 | Estrogen receptor | NM 000125.2 | Hs.208124 |
| ESR2 | Estrogen receptor | NM 001040276 + 1 | Hs.525392; HS660607 |
| PGR | Progesterone receptor | NM 000926.4 | Hs.368072 |
| AR | Androgen receptor | NM 000044 + 2 | Hs.496240 |

TABLE 1-continued

Genes of interest

| Gene_Symbol [A] | Ref. Sequences Description [A] | Ref. Sequences [A] | Unigene_ID [A] |
|---|---|---|---|
| AR | Androgen receptor | NM 001011645 + 1 | Hs.496240 |
| CYP19 | Aromatase | NM 000103.3 | |
| miRNA 205 | | | |
| miRNA 221 | | | |
| miRNA 222 | | | |
| SNAI1 | Snail homolog 1 | NM 005985.2 | Hs.48029 |
| SNAI2 | SLUG; Snail homolog 2 | NM 003068.3 | Hs.360174 |
| SNAI3 | SMUC; Snail homolog 3 | NM 17810.3 | Hs.673548 |

The terms "Ref. Sequences" and "Unigene 1D" relate to databases in which the respective proteins are listed under the given access number. These databases can be accessed over the NCBI server.

Additional details, features, characteristics and advantages of the invention are disclosed in the following examples that, in an exemplary fashion, show embodiments of the present invention. However, these examples should by no means be understood as to limit the scope of the invention.

EXAMPLE 1

Measurement of ESR1 by RT PCR

Molecular Methods

RNA was isolated from formalin-fixed paraffin-embedded ("FFPE") tumor tissue samples employing an experimental method based on proprietary magnetic beads from Siemens Medical Solutions Diagnostics. In short, the FFPE slide were lysed and treated with Proteinase K for 2 hours 55° C. with shaking After adding a binding buffer and the magnetic particles (Siemens Medical Solutions Diagnostic GmbH, Leverkusen, Germany) nucleic acids were bound to the particles within 15 minutes at room temperature. On a magnetic stand the supernatant was taken away and beads were washed several times with washing buffer. After adding elution buffer and incubating for 10 min at 70° C. the supernatant was taken away on a magnetic stand without touching the beads. After normal DNAse I treatment for 30 minutes at 37° C. and inactivation of DNAse I the solution was used for reverse transcription-polymerase chain reaction (RT-PCR).

RT-PCR was run as standard kinetic one-step Reverse Transcriptase TaqMan™ polymerase chain reaction (RT-PCR) analysis on a ABI7900 (Applied Biosystems) PCR system for assessment of mRNA expression. Raw data of the RT-PCR were normalized to one or combinations of the housekeeping genes RPL37A, GAPDH, RPL13, and HPRT1 by using the comparative ΔΔCT method, known to those skilled in the art. In brief, a total of 40 cycles of RNA amplification were applied and the cycle threshold (CT) of the target genes was set as being 0.5. CT scores were normalized by subtracting the CT score of the housekeeping gene RPL37A or the mean of the combinations from the CT score of the target gene (Delta CT). RNA results were then reported as 40-Delta CT or $2^{((40-(CT\ Target\ Gene-CT\ Housekeeping\ Gene)*(-1)))}$ ($2^{\wedge}$ (40−(CT Target Gene−CT Housekeeping Gene)*(−1))) scores, which would correlate proportionally to the mRNA expression level of the target gene. For each gene specific Primer/Probe were designed by Primer Express® software v2.0 (Applied Biosystems) according to manufactures instructions.

Statistics

The statistical analysis was performed with Graph Pad Prism Version 4 (Graph Pad Prism Software, Inc).

The clinical and biological variables were categorized into normal and pathological values according to standard norms. The Chi-square test was used to compare different groups for categorical variables. To examine correlations between different molecular factors, the Spearman rank correlation coefficient test was used.

For univariate analysis, logistic regression models with one covariate were used when looking at categorical outcomes. Survival curves were estimated by the method of Kaplan and Meier, and the curves were compared according to one factor by the log rank test. For the estimation of multivariate models, all parameters which were significant at the univariate analysis ($p<0.05$) were fitted to a Cox regression model using a backward forward stepwise method for the selection of covariates. Confidence intervals (CI) at 95% for hazard rates (HR) were calculated. All the probabilities that were calculated were two-tailed.

Experiments have repeatedly shown that determination of hormone receptor status by RT PCR consistently yielded better results than analysis by immunohistochemistry (IHC), i.e., while no stratification of patients could be achieved by analysis of IHC data, analysis of gene expression data obtained by PCR based methods consistently yielded significant results allowing a reliable stratification of patients in to high risk and low risk groups.

EXAMPLE 2

Determination of ESR1 Expression Using RT-PCR in a Lung Cancer Patient Cohort Hormone receptor RNA expression of ESR1, ESR2, PGR, AR was analyzed by Affymetrix array technologies and kPCR technologies by employing a standardized RNA-extraction method based on proprietary magnetic beads from Siemens Healthcare Diagnostics and using standard Taqman® PCR Methodology on the ABI7900 PCR system. Fresh tissue biopsy samples and tumor resectates of stage III and IV small cell and non small cell lung cancer patients kPCR from a non-stratified, population based cohort treated with chemotherapy (n=83) were analyzed.

By correlation analysis, it was surprisingly found that overexpression of ESR1 as assessed by Affymetrix and kPCR analysis indicates good prognosis of lung cancer patients treated by standard chemotherapy as indicated by prolonged disease free and overall survival. ESR1 expression displayed a broad range of relative copy number (2.5 logs) as determined by standard kPCR technologies after normalization to various housekeeping genes (RPL37A, GAPDH, RPL13, HPRT1, CALM2) in the populations based cohort (n=83) of patients with both SCLC and NSCLC. By taking technical cut-offs like the median and tertiles, it was shown that high expression is related to prolonged survival. Importantly, the ESR1 and AR expressing tumor group may benefit most from endocrine treatment options. The test could be used for stratification of lung cancer patients towards endocrine treatments in the late and also earlier setting. As the median expression of ESR1 and AR was lower than in breast cancer and there is need for quantitative assessment of ESR1 and AR expression to reliably select patients, it is reasonable to expect a technical superiority of the present approach over standard technologies (i.e., immunohistochemistry) will also persist also in lung cancer.

EXAMPLE 3

Determination of ESR Expression Using RT-PCR in NSCLC Patient Cohort

Figure 2:
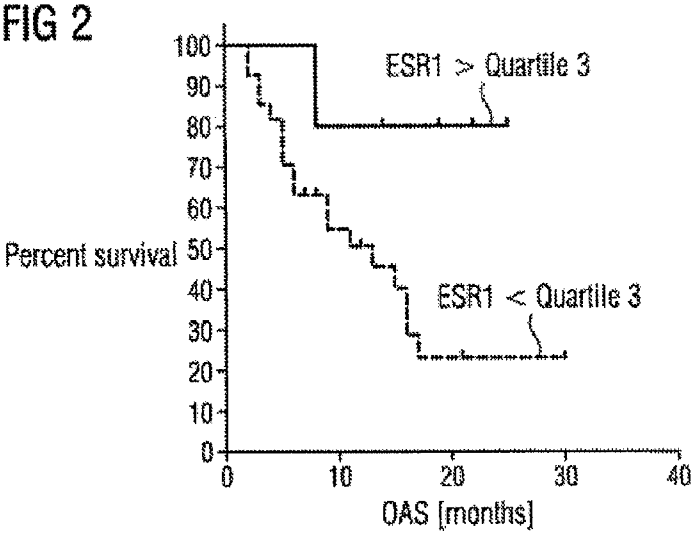
FIG. 2: Kaplan-Meier-Analysis of overall survival (OAS) of patients suffering from lung cancer based on i ESR1 (ER) determination. The overall survival (OAS) is depicted in months. Patients are stratified according to ESR1 expression above or below the third quartile of ESR1 expression.

By correlation analysis, it was surprisingly found that overexpression of ESR1 as kPCR analysis indicates good prognosis of non small cell lung cancer (NSCLC) patients (male and female Caucasian patients) treated by standard chemotherapy as indicated by prolonged disease free and overall survival. ESR1 expression displayed a broad range of relative copy number (2.5 logs) as determined by standard kPCR technologies after normalization to various housekeeping genes (RPL37A, GAPDH, RPL13, HPRT1, CALM2) in the populations based cohort (n=35) of patients with NSCLC. By taking technical cut-offs like the median and tertiles, it was shown that high expression is related to prolonged survival. Results for ESR1 expression greater or lower than median are shown in FIG. 1. Patients stratified according to ESR1 expression above or below the third quartile of ESR1 expression are shown in FIG. 2. The majority of patients were treated with a platinum-based regimen. Samples were FFPE tissue analyzed with RT-kPCR. The median follow up 9 month; 82% Stage IV; patient number was n=35.

EXAMPLE 4

Figure 3:
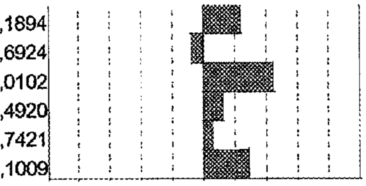
FIG. 3: Spearman correlation analysis between affected metastatic sites and ESR1 mRNA expression level in NSCLC patients. Patients are depicted according to ESR1 expression above and below the median (i.e., "1" vs "0" respectively). Metastatic site being affected is depicted as "1" or "0" depending on whether metastatic lesions were found before first line treatment.

Correlation of ESR1 Expression Determined by Using RT-PCR with Site of Initial Metastasis in NSCLC Patient Cohort By correlation analysis, it was surprisingly found that high ESR1 expression positively correlates with development of bone metastasis also in NSCLC patients as depicted in FIG. 3. In addition, metastasis to the adrenal gland trends to be significantly associated with adrenal metastasis, which is in females the major source of androgens. Tropism of hormone receptor positive NSCLC cells towards the endocrine gland has not been described before but is in line with the surprising finding that a subtype of NSCLC cells derives growth advantage from hormones such as androgens or its derivatives (estrogen).

EXAMPLE 5

Figure 4:
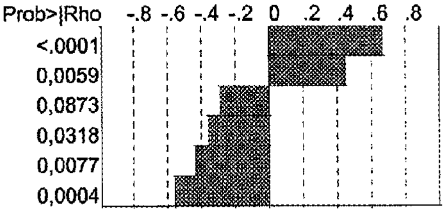
FIG. 4: Spearman correlation analysis between candidate genes (ESR1, SNAI2, CDH1, CDH11). Spearman correlation coefficients and p-values are depicted.

Spearman Correlation of ESR1, SNAI2, CDH1, CDHI1 Expression Determined by Using RT-PCR with Site of Initial Metastasis in NSCLC Patient Cohort In view of the extreme effect of hormone receptors on patient survival in NSCLC, the inventor has analyzed the promoter sites regulating the expression of hormone receptor RNA expression, i.e., ESR1, ESR2, PGR, AR to identify candidate genes that oppose the effect of ESR1 and contribute to more aggressive and hormone insensitive tumor subtypes. Thereby he had the idea to first analyze the isoform specific expression of ESR1 in cancer and then analyze the respective isoform specific promoter sites in molecular detail. Surprisingly, he has identified tumor specific ESR1 isoforms, whose promoter region in turn exhibited several snail transcription factor binding sites (i.e., bindings sites for SNAI1, SNAI2 and SNAI3). The interaction of hormone receptors and snail factors was then analyzed in diverse Affymetrix data sets. As one example, fresh tissue biopsy samples (laparoscopy; pre-treatment) and tumor resectates (surgery; post-treatment) of stage III and IV ovarian cancer patients (n=40) neoadjuvantly treated with chemotherapy (6×AUC) were analyzed by Affymetrix expression profiling. By Spearman correlation analysis and as depicted in FIG. 4, it could be proven that the transcription factor SNAI2 indeed strongly and negatively correlated with ESR1 (r=−0.56; p=0.0004) followed by E-Cadherin ("CDH1"; r=−0.36; p=0.03), both of which are associated with epithelial and good prognosis phenotype. Conversely, SNAI2 positively correlated with MMP2 (r=0.86; p<0.0001), Spon2 (r=0.80; p<0.0001), ADAM12 (r=0.72; p<0.0001) and OB-Cadherin ("CDH11"; r=0.66; p=0.03). Surprisingly the dramatic switch of cell-cell-adhesion from E-Cadherin to OB-Cadherin further illustrated the Epithelial-Mesenchymal transition, which might be associated with highly invasive behavior of tumor cells. However, the presence of OB-Cadherin might also indicate successful recruitment of osteoblast-like bone marrow cells into the primary tumor site further indicating the more aggressive phenotype of ESR1 low expressing and simultaneously SNAI2 overexpressing tumors.

EXAMPLE 6

Figure 5:
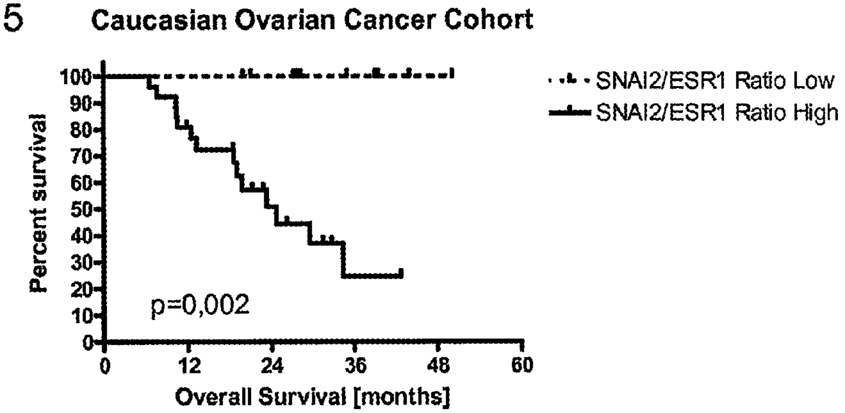
FIG. 5: Kaplan-Meier-Analysis of Recurrence Free Survival (RFS) of patients suffering from ovarian cancer based on combined SNAI2 and ESR1 determination. The Recurrence Free Survival (RFS) is depicted in months. Patients are stratified according to SNAI2/ESR1 two gene ratios.

Determination of ESR1 in Combination with SNAI2 Expression Using Array Profiling in Ovarian Cancer Patient Cohort A two gene-ratio was generated by dividing SNAI2 by ESR1. As depicted in FIG. 5, Kaplan-Meier-Anaylsis revealed that ovarian cancer patients having high two-gene-ratio values (Cut-Off 0.21), indicating high SNAI2 expression and simultaneously low ESR1 expression, which accounts for approximately one third of the ovarian cancer patients, have a worse overall survival than patients having high ESR1 expression and low SNAI2 expression. The latter exhibited 100% overall survival at three years within this stage IV neoadjuvantly treated ovarian cancer cohort (Hazard ratio 0.00; p=0.0021; Median Recurrence free Survival not reached versus 24.8 months; 100% Overall Survival versus 20% Overall Survival at three years of follow-up). By generating a two gene ratio of SNAI2 and ESR1 the test can be performed without using any housekeeping gene, which further limits the number of required genes and reduces complexity and costs for performing the assay. The test could be used for stratification of cancer patients towards targeted treatments in the late and also earlier setting. Particularly SNAI2 negatively correlates with PARP1 (r=−0.54; p=0.0004) meaning that high expression of SNAI2 is associated with low expression of PARP 1. PARP1 is the target of PARP Inhibitors. Lower expression of PARP1 (and/or BRCA1) indicates responsiveness towards this regimen. However, the expression of PARP1 is very difficult to determine on protein and mRNA level, due to comparably low general expression and low dynamic range. However patients responding to PARP Inhibitors could be more easily detected by determining the balance between hormone receptors and SNAI factors.

EXAMPLE 7

Determination of ESR1 in Combination with SNAI2 Expression Using Array Profiling in Non-Small Cell Lung Cancer Patient Cohort To further validate, that the two gene-ratio generated by dividing SNAI2 by ESR1 is also prognostic in other cancer indications and particularly in lung cancer, the public available whole genome Affymetrix gene expression data from Jinkook Kim (GSE8894; Lee E S et al. (2008): Prediction of Recurrence-free survival in postoperative non-small cell lung cancer patients by using an integrated model of clinical and gene expression. Clin Cancer Res. 14 (22): 7397-404) was retrieved from the GEO database. In brief, a total of 253 fresh frozen non-small lung cancer tumor samples from patients who underwent curative resection of NSCLC at Samsung Medical Center in Seoul (South Korea) between January 1995 and December 2005 were selected and acceptable RNA quality for microarray analysis was achieved from 138 tumors.

Figure 6:
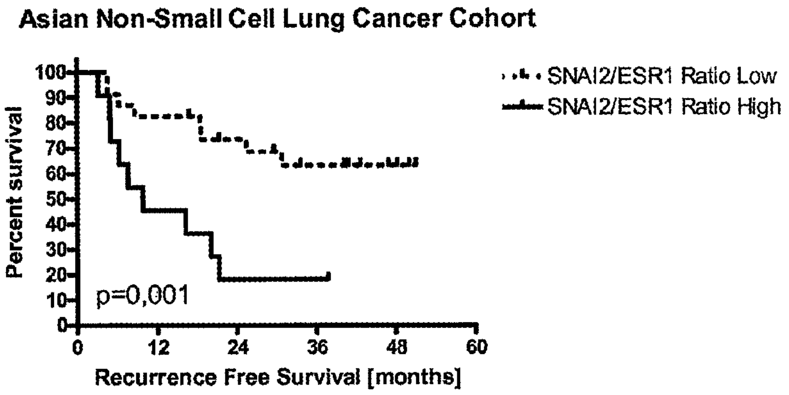
FIG. 6: Kaplan-Meier-Analysis of Recurrence Free Survival (RFS) of patients suffering from lung cancer based on combined SNAI2 and ESR1 determination. The Recurrence Free Survival (RFS) is depicted in months. Patients are stratified according to SNAI2/ESR1 two gene ratios.

The first validation focused on female NSCLC patients (n=34; Adenocarcinoma and Squamous Cell Carcinoma). The two-gene ratio was constructed by dividing SNAI2 by ESR1 expression values. According to this invention low gene-ratio values reflect lower expression of ESR1 and simultaneously higher expression of ESR1 and are associated with lower risk of recurrence. By using a two gene-ratio cut-off at 2.32 a low risk was predicted for approximately 30% of the women (i.e., 11/34 patients). As depicted in FIG. 6, the Kaplan-Meier analysis validated that the low-risk prediction by using the SNAI2 and ESR1 expression ratio have a lower risk of recurrence (Hazard ratio 0.25; p=0.0012; Median Recurrence free Survival not reached versus 9.8 months; 70% Recurrence Free Survival versus 20% Recurrence Free Survival at two years of follow-up). This validates the prognostic significance of SNAI2 and ESR1 in independent patients. Importantly, this indicates that the invention not only works for metastatic, Caucasian NSCLC patients treated within a first-line chemotherapy protocol as depicted in Example 3, but also works in non-metastatic, Asian NSCLC patients after curative resection of the tumor mass. This means, that the invention is suitable for NSCLC patients at different disease and treatment stages. Importantly, as estrogen receptor is capable of triggering tumor growth, the determination of hormone receptors (particularly ESR1) and/or Snail factors (particularly SNAI2) is important for peri- or post-menopausal women, to evaluate possible risks associated with hormone replacement therapy, as treatment with hormones could force tumor growth and aggressiveness particularly in ESR1 high expressors and/or SNAI2 low expressors.

EXAMPLE 8

Figure 7:
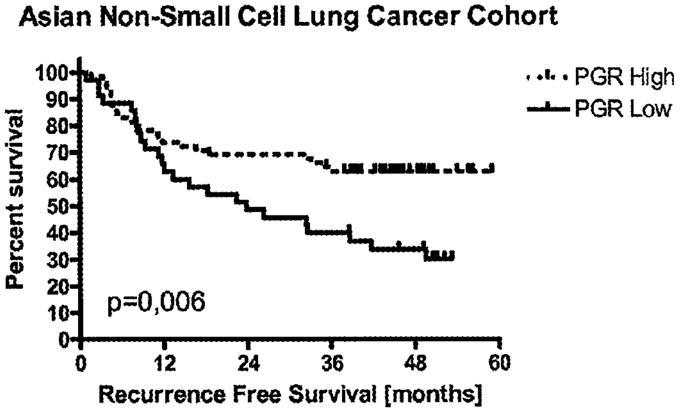
FIG. 7: Kaplan-Meier-Analysis of Recurrence Free Survival (RFS) of patients suffering from lung cancer based PGR expression determination. The Recurrence Free Survival (RFS) is depicted in months. Patients are stratified according to PGR expression levels above or below the cut-off vale of 2.28 dividing the cohort in ~65% Low Risk patients and ~35% High Risk patients.

Determination of PGR Using Array Profiling in Non-Small Cell Lung Cancer Patient Cohort The second validation focused on male NSCLC patients (n=100; Adenocarcinoma and Squamous Cell Carcinoma). As depicted in FIG. 7 the Kaplan-Meier analysis validated that high PGR expression indicates lower risk of recurrence (Hazard ratio 0.46; p=0.0056; Median Recurrence free Survival not reached versus 23 months; 65% Recurrence Free Survival versus 40% Recurrence Free Survival at three years of follow-up). This validates that hormone receptor expression is significant also for male NSCLC in Asian patients having undergone curative resection of the primary tumor (see above).

What is claimed is:

1. A method of classifying a sample of a patient who suffers from or is at risk of developing lung cancer, said method comprising the steps of:

a. providing at least one synthetic cDNA molecule labelled with one or more fluorescent molecules, luminescent molecules, radioactive molecules, enzymatic molecules and/or quenching molecules;

b. detecting in said sample from said patient the RNA expression level by using PCR by creating artificial RNA:cDNA or RNA:probe molecules of at least one gene encoding for a hormone receptor is an estrogen receptor 1 (ESR1) in said sample;

c. comparing the one or more expression level(s) determined in step (b) with one or more expression level(s) of one or more reference gene(s) by detecting the RNA expression by using PCR, by creating artificial RNA:cDNA or RNA:probe molecules on or more reference gene(s); and d. classifying the sample of said patient from the outcome of the comparison in step (c) into one of at least two classifications to predict the therapeutic success of a chemotherapy or endocrine therapy treatment for lung cancer, wherein the endocrine treatment comprises the administration of an estrogen analogue selected from the group consisting essentially of tamoxifen, raloxifen, and an antiestrogen drug selected from the group consisting essentially of anastrozole, letrozole, exemestane, fulvestrant, toremifene, gosereline, and megasterol acetate.

2. A method of treatment of a patient who suffers from or is at risk of developing lung cancer following the method of classifying a sample of the patient according to claim 1, comprising administering a drug to the patient based on the classification step (c), wherein the drug has a mode of action directed at (i) at least one hormone receptor that is an estrogen receptor 1 (ESR1), or (ii) the respective signalling pathways of the at least one hormone receptor, or (iii) repair mechanisms related to the at least one hormone receptor or the respective signaling pathways thereof.

3. The method according to claim 2, wherein the classifying the sample of said patient from the outcome of the comparison in step (c) into one of at least two classifications to predict the therapeutic success of a chemotherapy or endocrine therapy treatment for lung cancer is based on the prediction of therapeutic success recommendation of administration of suitable estrogene analogue.

4. The method according to claim 2, wherein the patient is a peri- or postmenopausal woman being treated with a hormone replacement therapy (HRT) and the drug is administered as hormone replacement therapy (HRT).

5. The method according to claim 1, wherein the hybridization step uses an oligonucleotide comprising at least one nucleotide sequence which is capable of hybridizing to a nucleic acid molecule set forth as SEQ ID NO 1 (human ESR1).

6. A method according to claim 1, wherein said one or more reference gene(s) is at least one housekeeping gene and at least one Epithelial Mesenchymal Transition (EMT) marker gene.

7. The method according to claim 6, wherein the at least one housekeeping gene is selected from the group consisting of RPL37A, GAPDH, RPL 13, and HPRT1; and the at least one EMT marker gene is selected from the group consisting of SNAIL SNAI2, and SNAI3.

8. The method according to claim 7, wherein the comparing step (b) includes calculating a ratio between the expression levels of at least one hormone receptor and at least one EMT marker gene.

9. The method according to claim 8, wherein the comparing step (b) includes calculating a ratio between the expression levels of ESR1 and SNAI2.

10. The method according to claim 1, wherein said expression levels of the at least one gene encoding for a hormone receptor and the one or more reference gene(s) are detected by a ΔΔCT method.

11. The method according to claim 10, wherein said ΔΔCT method comprises setting the cycle threshold (CT) of the target genes to 0.5 and normalizing the CT scores by subtracting the CT score of the one or more reference genes or the mean of the combinations from the CT score of the at least one gene encoding for a hormone receptor (Delta CT).

12. The method according to claim 11, wherein said expression levels are determined in a formalin- or paraffin-fixed tissue sample.

13. The method according to claim 12, wherein the formalin- or paraffin-fixed tissue sample placed in contact with (i) a lysis agent, (ii) silica-coated magnetic particles, and (iii) a chaotropic salt prior to the detection step (a).

14. The method according to claim 13, wherein said cancer is an adenocarcinoma.

15. The method according to claim 14, wherein the expression level(s) detected in step (a) is/are correlated with said patient's data, said data being selected from the group consisting of etiopathology data, clinical symptoms, anamnesis data and/or data concerning the therapeutic regimen.

16. The method according to claim 1, further comprising d. detecting in said sample from said patient the RNA expression level by using a hybridization based method, a PCR based method, or an array based method, by creating artificial RNA:cDNA or RNA:probe molecules of a progesterone receptor in said sample;

e. comparing the one or more expression level(s) determined in step (d) with one or more expression level(s) of one or more reference gene(s) by detecting the RNA expression by using a hybridization based method, a PCR based method, or an array based method, by creating artificial RNA:cDNA or RNA:probe molecules on or more reference gene(s);

f. classifying the sample of said patient from the outcome of the comparison in step (e) into one of at least two classifications to predict the therapeutic success of a chemotherapy or endocrine therapy treatment for lung cancer; and g. treating said patient with a chemotherapy or endocrine therapy treatment for lung cancer if the patient is within the positive classification of step (c) and (f).

17. A method of classifying a sample of a patient who suffers from or is at risk of developing lung cancer, said method comprising the steps of:

a. providing at least one synthetic cDNA molecule labelled with one or more fluorescent molecules, luminescent molecules, radioactive molecules, enzymatic molecules and/or quenching molecules;

b. detecting in said sample from said patient the RNA expression level by using PCR by creating artificial RNA:cDNA or RNA:probe molecules of at least one gene encoding for a hormone receptor is selected from the group consisting of an estrogen receptor 1 (ESR1) and/or a progesterone receptor in said sample;

c. comparing the one or more expression level(s) determined in step (b) with one or more expression level(s) of one or more reference gene(s) by detecting the RNA expression by using PCR by creating artificial RNA: cDNA or RNA:probe molecules on or more reference gene(s);

d. classifying the sample of said patient from the outcome of the comparison in step (c) into one of at least two classifications to predict the therapeutic success of a chemotherapy or endocrine therapy treatment for lung cancer; and e. treating said patient with a chemotherapy or endocrine therapy treatment for lung cancer if the patient is within the positive classification of step (d), wherein the endocrine treatment comprises the administration of an estrogen analogue selected from the group consisting essentially of tamoxifen, raloxifen, and an antiestrogen drug selected from the group consisting essentially of anastrozole, letrozole, exemestane, fulvestrant, toremifene, gosereline and megasterol acetate.

* * * * *

SEQUENCE LISTING

<160> NUMBER OF SEQ ID NOS: 9

<210> SEQ ID NO 1
<211> LENGTH: 6456
<212> TYPE: DNA
<213> ORGANISM: Homo sapiens
<223> OTHER INFORMATION: ESR1-Estrogen receptor

<400> SEQUENCE: 1

```
gagttgtgcc tggagtgatg tttaagccaa tgtcagggca aggcaacagt ccctggccgt     60
cctccagcac ctttgtaatg catatgagct cgggagacca gtacttaaag ttggaggccc    120
gggagcccag gagctggcgg agggcgttcg tcctgggact gcacttgctc ccgtcgggtc    180
gcccggcttc accggacccg caggctcccg gggcagggcc ggggccagag ctcgcgtgtc    240
ggcgggacat gcgctgcgtc gcctctaacc tcgggctgtg ctctttttcc aggtggcccg    300
ccggtttctg agccttctgc cctgcgggga cacggtctgc accctgcccg cggccacgga    360
ccatgaccat gaccctccac accaaagcat ccgggatggc cctactgcat cagatccaag    420
ggaacgagct ggagcccctg aaccgtccgc agctcaagat ccccctggag cggcccctgg    480
gcgaggtgta cctggacagc agcaagcccg ccgtgtacaa ctaccccgag ggcgccgcct    540
acgagttcaa cgccgcggcc gccgccaacg cgcaggtcta cggtcagacc ggcctcccct    600
acggccccgg gtctgaggct gcggcgttcg gctccaacgg cctggggggt ttccccccac    660
tcaacagcgt gtctccgagc ccgctgatgc tactgcaccc gccgccgcag ctgtcgcctt    720
tcctgcagcc ccacggccag caggtgccct actacctgga gaacgagccc agcggctaca    780
cggtgcgcga ggccggcccg ccggcattct acaggccaaa ttcagataat cgacgccagg    840
gtggcagaga aagattggcc agtaccaatg acaagggaag tatggctatg gaatctgcca    900
aggagactcg ctactgtgca gtgtgcaatg actatgcttc aggctaccat tatggagtct    960
ggtcctgtga gggctgcaag gccttcttca agagaagtat tcaaggacat aacgactata   1020
tgtgtccagc caccaaccag tgcaccattg ataaaaacag gaggaagagc tgccaggcct   1080
gccggctccg caaatgctac gaagtgggaa tgatgaaagg tgggatacga aaagaccgaa   1140
gaggagggag aatgttgaaa cacaagcgcc agagagatga tggggagggc aggggtgaag   1200
tggggtctgc tggagacatg agagctgcca acctttggcc aagcccgctc atgatcaaac   1260
gctctaagaa gaacagcctg gccttgtccc tgacggccga ccagatggtc agtgccttgt   1320
tggatgctga gccccccata ctctattccg agtatgatcc taccagaccc ttcagtgaag   1380
cttcgatgat gggcttactg accaacctgg cagacaggga gctggttcac atgatcaact   1440
gggcgaagag ggtgccaggc tttgtggatt tgaccctcca tgatcaggtc caccttctag   1500
aatgtgcctg gctagagatc ctgatgattg gtctcgtctg gcgctccatg gagcacccag   1560
ggaagctact gtttgctcct aacttgctct tggacaggaa ccagggaaaa tgtgtagagg   1620
gcatggtgga gatcttcgac atgctgctgg ctacatcatc tcggttccgc atgatgaatc   1680
tgcagggaga ggagtttgtg tgcctcaaat ctattatttt gcttaattct ggagtgtaca   1740
catttctgtc cagcaccctg aagtctctgg aagagaagga ccatatccac cgagtcctgg   1800
acaagatcac agacactttg atccacctga tggccaaggc aggcctgacc ctgcagcagc   1860
agcaccagcg gctggcccag ctcctcctca tcctctccca catcaggcac atgagtaaca   1920
aaggcatgga gcatctgtac agcatgaagt gcaagaacgt ggtgcccctc tatgacctgc   1980
tgctggagat gctggacgcc caccgcctac atgcgcccac tagccgtgga ggggcatccg   2040
```

-continued

```
tggaggagac ggaccaaagc cacttggcca ctgcgggctc tacttcatcg cattccttgc   2100
aaaagtatta catcacgggg gaggcagagg gtttccctgc cacggtctga gagctccctg   2160
gctcccacac ggttcagata atccctgctg cattttaccc tcatcatgca ccactttagc   2220
caaattctgt ctcctgcata cactccggca tgcatccaac accaatggct ttctagatga   2280
gtggccattc atttgcttgc tcagttctta gtggcacatc ttctgtcttc tgttgggaac   2340
agccaaaggg attccaaggc taaatctttg taacagctct ctttcccct tgctatgtta    2400
ctaagcgtga ggattcccgt agctcttcac agctgaactc agtctatggg ttggggctca   2460
gataactctg tgcatttaag ctacttgtag agacccaggc ctggagagta gacattttgc   2520
ctctgataag cactttttaa atggctctaa gaataagcca cagcaaagaa tttaaagtgg   2580
ctcctttaat tggtgacttg gagaaagcta ggtcaagggt ttattatagc accctcttgt   2640
attcctatgg caatgcatcc ttttatgaaa gtggtacacc ttaaagcttt tatatgactg   2700
tagcagagta tctggtgatt gtcaattcat tcccccctata ggaatacaag gggcacacag  2760
ggaaggcaga tcccctagtt ggcaagacta ttttaacttg atacactgca gattcagatg   2820
tgctgaaagc tctgcctctg gctttccggt catgggttcc agttaattca tgcctcccat   2880
ggacctatgg agagcagcaa gttgatctta gttaagtctc cctatatgag ggataagttc   2940
ctgatttttg tttttatttt tgtgttacaa aagaaagccc tccctccctg aacttgcagt   3000
aaggtcagct tcaggacctg ttccagtggg cactgtactt ggatcttccc ggcgtgtgtg   3060
tgccttacac aggggtgaac tgttcactgt ggtgatgcat gatgagggta aatggtagtt   3120
gaaaggagca ggggccctgg tgttgcattt agccctgggg catggagctg aacagtactt   3180
gtgcaggatt gttgtggcta ctagagaaca agagggaaag tagggcagaa actggataca   3240
gttctgaggc acagccagac ttgctcaggg tggccctgcc acaggctgca gctacctagg   3300
aacattcctt gcagaccccg cattgccctt tgggggtgcc ctgggatccc tggggtagtc   3360
cagctcttct tcatttccca gcgtggccct ggttggaaga agcagctgtc acagctgctg   3420
tagacagctg tgttcctaca attggcccag caccctgggg cacgggagaa gggtggggac   3480
cgttgctgtc actactcagg ctgactgggg cctggtcaga ttacgtatgc ccttggtggt   3540
ttagagataa tccaaaatca gggtttggtt tggggaagaa aatcctcccc cttcctcccc   3600
cgccccgttc cctaccgcct ccactcctgc cagctcattt ccttcaattt cctttgaacc   3660
tataggctaa aaaagaaagg ctcattccag ccacagggca gccttccctg ggcctttgct   3720
tctctagcac aattatgggt tacttccttt ttcttaacaa aaaagaatgt ttgatttcct   3780
ctgggtgacc ttattgtctg taattgaaac cctattgaga ggtgatgtct gtgttagcca   3840
atgacccagg tgagctgctc gggcttctct tggtatgtct tgtttggaaa agtggatttc   3900
attcatttct gattgtccag ttaagtgatc accaaaggac tgagaatctg ggagggcaaa   3960
aaaaaaaaaa aagtttttat gtgcacttaa atttggggac aattttatgt atctgtgtta   4020
aggatatgtt taagaacata attcttttgt tgctgtttgt ttaagaagca ccttagtttg   4080
tttaagaagc accttatata gtataatata tatttttttg aaattacatt gcttgtttat   4140
cagacaattg aatgtagtaa ttctgttctg gatttaattt gactgggtta acatgcaaaa   4200
accaaggaaa aatatttagt tttttttttt ttttttgtat acttttcaag ctaccttgtc   4260
atgtatacag tcatttatgc ctaaagcctg gtgattattc atttaaatga agatcacatt   4320
tcatatcaac ttttgtatcc acagtagaca aaatagcact aatccagatg cctattgttg   4380
gatattgaat gacagacaat cttatgtagc aaagattatg cctgaaaagg aaaattattc   4440
```

```
agggcagcta attttgcttt taccaaaata tcagtagtaa tatttttgga cagtagctaa   4500
tgggtcagtg ggttcttttt aatgtttata cttagatttt cttttaaaaa aattaaaata   4560
aaacaaaaaa aaatttctag gactagacga tgtaatacca gctaaagcca aacaattata   4620
cagtggaagg ttttacatta ttcatccaat gtgtttctat tcatgttaag atactactac   4680
atttgaagtg ggcagagaac atcagatgat tgaaatgttc gcccaggggt ctccagcaac   4740
tttggaaatc tctttgtatt tttacttgaa gtgccactaa tggacagcag atattttctg   4800
gctgatgttg gtattgggtg taggaacatg atttaaaaaa aaactcttgc ctctgctttc   4860
ccccactctg aggcaagtta aaatgtaaaa gatgtgattt atctgggggg ctcaggtatg   4920
gtggggaagt ggattcagga atctggggaa tggcaaatat attaagaaga gtattgaaag   4980
tatttggagg aaaatggtta attctgggtg tgcaccaggg ttcagtagag tccacttctg   5040
ccctggagac cacaaatcaa ctagctccat ttacagccat ttctaaaatg gcagcttcag   5100
ttctagagaa gaaagaacaa catcagcagt aaagtccatg gaatagctag tggtctgtgt   5160
ttcttttcgc cattgcctag cttgccgtaa tgattctata atgccatcat gcagcaatta   5220
tgagaggcta ggtcatccaa agagaagacc ctatcaatgt aggttgcaaa atctaacccc   5280
taaggaagtg cagtctttga tttgatttcc ctagtaacct tgcagatatg tttaaccaag   5340
ccatagccca tgccttttga gggctgaaca aataagggac ttactgataa tttacttttg   5400
atcacattaa ggtgttctca ccttgaaatc ttatacactg aaatggccat tgatttaggc   5460
cactggctta gagtactcct tcccctgcat gacactgatt acaaatactt tcctattcat   5520
actttccaat tatgagatgg actgtgggta ctgggagtga tcactaacac catagtaatg   5580
tctaatattc acaggcagat ctgcttgggg aagctagtta tgtgaaaggc aaatagagtc   5640
atacagtagc tcaaaaggca accataattc tctttggtgc aggtcttggg agcgtgatct   5700
agattacact gcaccattcc caagttaatc ccctgaaaac ttactctcaa ctggagcaaa   5760
tgaactttgg tcccaaatat ccatcttttc agtagcgtta attatgctct gtttccaact   5820
gcatttcctt tccaattgaa ttaaagtgtg gcctcgtttt tagtcattta aaattgtttt   5880
ctaagtaatt gctgcctcta ttatggcact tcaattttgc actgtctttt gagattcaag   5940
aaaaatttct attctttttt ttgcatccaa ttgtgcctga acttttaaaa tatgtaaatg   6000
ctgccatgtt ccaaacccat cgtcagtgtg tgtgtttaga gctgtgcacc ctagaaacaa   6060
catattgtcc catgagcagg tgcctgagac acagacccct ttgcattcac agagaggtca   6120
ttggttatag agacttgaat taataagtga cattatgcca gtttctgttc tctcacaggt   6180
gataaacaat gctttttgtg cactacatac tcttcagtgt agagctcttg ttttatggga   6240
aaaggctcaa atgccaaatt gtgtttgatg gattaatatg ccctttttgcc gatgcatact   6300
attactgatg tgactcggtt ttgtcgcagc tttgctttgt ttaatgaaac acacttgtaa   6360
acctcttttg cactttgaaa aagaatccag cgggatgctc gagcacctgt aaacaatttt   6420
ctcaacctat ttgatgttca aataaagaat taaact                             6456
```

<210> SEQ ID NO 2
<211> LENGTH: 2745
<212> TYPE: DNA
<213> ORGANISM: Homo sapiens
<223> OTHER INFORMATION: ESR2 - Estrogen receptor

<400> SEQUENCE: 2

```
gtgtgagggc gcccggcttc caggcagtaa tgggcgggtc cctgcgcggg agcgtggcgg     60
```

```
gcgctggact ctacagcaga tgtggaactg gagagcttgg cgcgccttcc gactttgtca    120
cacacctgcg ccgccagact ggggtcgggc ccctccgcgt tctgctctgg agtgcctggg    180
tctgggccca gcaccgcgct tttagaatct cctcagctga atctgacgct cagcagtggg    240
tgaagcgcag ccccctgttt caggccctgc cgagctggaa ggagtgtcag agctggagcg    300
cgcgtggccc cctctgtgtt ggggtcaccc cggggttgcc agggctcagg gagggtcgta    360
gtctggattt tgtcacccgc acgtccccac cccccagcag gtctggggtt ggagaatcca    420
cgcgggcttc ataagctaga tgccagttaa ctgtcgagag gggacgctcc ctcctcgtag    480
gcgtccacac tggagaagga ataagatggg cgattgcctg ggaagcctga cagggcggcg    540
gcagctggga tgctggagag gactggcccc ttgagttact gagtccgatg aatgtgcttg    600
ctctgctgga ggaaccgcgc tcaggttaca gtcatcccaa tatggttctg aagccattat    660
acttgcccac gaatctttga gaacattata atgacctttg tgcctcttct tgcaaggtgt    720
tttctcagct gttatctcaa gacatggata taaaaaactc accatctagc cttaattctc    780
cttcctccta caactgcagt caatccatct taccccctgga gcacggctcc atatacatac    840
cttcctccta tgtagacagc caccatgaat atccagccat gacattctat agccctgctg    900
tgatgaatta cagcattccc agcaatgtca ctaacttgga aggtgggcct ggtcggcaga    960
ccacaagccc aaatgtgttg tggccaacac ctgggcacct ttctccttta gtggtccatc   1020
gccagttatc acatctgtat gcggaacctc aaaagagtcc ctggtgtgaa gcaagatcgc   1080
tagaacacac cttacctgta aacagagaga cactgaaaag gaaggttagt gggaaccgtt   1140
gcgccagccc tgttactggt ccaggttcaa agagggatgc tcacttctgc gctgtctgca   1200
gcgattacgc atcgggatat cactatggag tctggtcgtg tgaaggatgt aaggcctttt   1260
ttaaaagaag cattcaagga cataatgatt atatttgtcc agctacaaat cagtgtacaa   1320
tcgataaaaa ccggcgcaag agctgccagg cctgccgact tcggaagtgt tacgaagtgg   1380
gaatggtgaa gtgtggctcc cggagagaga gatgtgggta ccgccttgtg cggagacaga   1440
gaagtgccga cgagcagctg cactgtgccg gcaaggccaa gagaagtggc ggccacgcgc   1500
cccgagtgcg ggagctgctg ctggacgccc tgagccccga gcagctagtg ctcaccctcc   1560
tggaggctga gccgccccat gtgctgatca gccgccccag tgcgcccttc accgaggcct   1620
ccatgatgat gtccctgacc aagttggccg acaaggagtt ggtacacatg atcagctggg   1680
ccaagaagat tcccggcttt gtggagctca gcctgttcga ccaagtgcgg ctcttggaga   1740
gctgttggat ggaggtgtta atgatggggc tgatgtggcg ctcaattgac caccccggca   1800
agctcatctt tgctccagat cttgttctgg acagggatga ggggaaatgc gtagaaggaa   1860
ttctggaaat ctttgacatg ctcctggcaa ctacttcaag gtttcgagag ttaaaactcc   1920
aacacaaaga atatctctgt gtcaaggcca tgatcctgct caattccagt atgtaccctc   1980
tggtcacagc gacccaggat gctgacagca gccggaagct ggctcacttg ctgaacgccg   2040
tgaccgatgc tttggtttgg gtgattgcca agagcggcat ctcctcccag cagcaatcca   2100
tgcgcctggc taacctcctg atgctcctgt cccacgtcag gcatgcgagg gcagaaaagg   2160
cctctcaaac actcacctca tttggaatga agatggagac tcttttgcct gaagcaacga   2220
tggagcagtg accctctaat caactcggtg gcctaaagaa aaatcttggg taacattttc   2280
acttcagttt ccctctggga tcattgtaat ccatgaaaaa aataatttta aagaaagagt   2340
taaaatactt tgaagttagt tatgtggtta aaaaccacct tcctttctat tatcaatcca   2400
```

acaatttgat aactgtaaac gctaaagtga agacggattc tcttcagatg gtctccttaa 2460
ctgcccaggg cttgcagatg tctcacccat gaggggcacc aatgtagaaa gctgaggctt 2520
catctactga tgagcttcac tggtttcccc tgaggtttgt gctttggcag agaaggggag 2580
gaggggactg ggattgtgtg gtcagctgtg cctgccaaca gatgcaggtt aggaactgtg 2640
ttcagtatct tccaataaga aaggggaaat gccgatgcct atcctctttg tttaggtaga 2700
aagtaaaatg ctactggact taaatgggca aaaaaaaaaa aaaaa 2745

<210> SEQ ID NO 3
<211> LENGTH: 13037
<212> TYPE: DNA
<213> ORGANISM: Homo sapiens
<223> OTHER INFORMATION: PGR - Progesterone receptor

<400> SEQUENCE: 3
agtccacagc tgtcactaat cggggtaagc cttgttgtat ttgtgcgtgt gggtggcatt 60
ctcaatgaga actagcttca cttgtcattt gagtgaaatc tacaacccga ggcggctagt 120
gctcccgcac tactgggatc tgagatcttc ggagatgact gtcgcccgca gtacggagcc 180
agcagaagtc cgacccttcc tgggaatggg ctgtaccgag aggtccgact agccccaggg 240
ttttagtgag gggcagtgg aactcagcga gggactgaga gcttcacagc atgcacgagt 300
ttgatgccag agaaaaagtc gggagataaa ggagccgcgt gtcactaaat tgccgtcgca 360
gccgcagcca ctcaagtgcc ggacttgtga gtactctgcg tctccagtcc tcggacagaa 420
gttggagaac tctcttggag aactccccga gttaggagac gagatctcct aacaattact 480
actttttctt gcgctcccca cttgccgctc gctgggacaa acgacagcca cagttcccct 540
gacgacagga tggaggccaa gggcaggagc tgaccagcgc cgccctcccc cgcccccgac 600
ccaggaggtg gagatccctc cggtccagcc acattcaaca cccactttct cctccctctg 660
cccctatatt cccgaaaccc cctcctcctt cccttttccc tcctcctgga gacgggggag 720
gagaaaaggg gagtccagtc gtcatgactg agctgaaggc aaagggtccc cgggctcccc 780
acgtggcggg cggcccgccc tcccccgagg tcggatcccc actgctgtgt cgcccagccg 840
caggtccgtt cccggggagc cagacctcgg acaccttgcc tgaagtttcg gccatacct a 900 tctccctgga cgggctactc ttccctcggc cctgccaggg acaggacccc tccgacgaaa 960
agacgcagga ccagcagtcg ctgtcggacg tggagggcgc atattccaga gctgaagcta 1020
caaggggtgc tggaggcagc agttctagtc ccccagaaaa ggacagcgga ctgctggaca 1080
gtgtcttgga cactctgttg gcgccctcag gtcccgggca gagccaaccc agccctcccg 1140
cctgcgaggt caccagctct tggtgcctgt ttggccccga acttcccgaa gatccaccgg 1200
ctgcccccgc cacccagcgg gtgttgtccc cgctcatgag ccggtccggg tgcaaggttg 1260
gagacagctc cgggacggca gctgcccata aagtgctgcc ccggggcctg tcaccagccc 1320
ggcagctgct gctcccggcc tctgagagcc ctcactggtc cggggcccca gtgaagccgt 1380
ctccgcaggc cgctgcggtg gaggttgagg aggaggatgg ctctgagtcc gaggagtctg 1440
cgggtccgct tctgaagggc aaacctcggg ctctgggtgg cgcggcggct ggaggaggag 1500
ccgcggctgt cccgccgggg gcggcagcag gaggcgtcgc cctggtcccc aaggaagatt 1560
cccgcttctc agcgcccagg gtcgccctgg tggagcagga cgcgccgatg gcgcccgggc 1620
gctccccgct ggccaccacg gtgatggatt tcatccacgt gcctatcctg cctctcaatc 1680
acgccttatt ggcagcccgc actcggcagc tgctggaaga cgaaagttac gacggcgggg 1740

-continued

```
ccggggctgc cagcgccttt gccccgccgc ggagttcacc ctgtgcctcg tccaccccgg   1800
tcgctgtagg cgacttcccc gactgcgcgt acccgcccga cgccgagccc aaggacgacg   1860
cgtaccctct ctatagcgac ttccagccgc ccgctctaaa gataaaggag gaggaggaag   1920
gcgcggaggc ctccgcgcgc tccccgcgtt cctaccttgt ggccggtgcc aaccccgcag   1980
ccttcccgga tttcccgttg gggccaccgc ccccgctgcc gccgcgagcg accccatcca   2040
gacccgggga agcggcggtg acggccgcac ccgccagtgc ctcagtctcg tctgcgtcct   2100
cctcggggtc gaccctggag tgcatcctgt acaaagcgga gggcgcgccg ccccagcagg   2160
gcccgttcgc gccgccgccc tgcaaggcgc cgggcgcgag cggctgcctg ctcccgcggg   2220
acggcctgcc ctccacctcc gcctctgccg ccgccgccgg ggcggccccc gcgctctacc   2280
ctgcactcgg cctcaacggg ctcccgcagc tcggctacca ggccgccgtg ctcaaggagg   2340
gcctgccgca ggtctacccg ccctatctca actacctgag gccggattca gaagccagcc   2400
agagcccaca atacagcttc gagtcattac ctcagaagat ttgtttaatc tgtggggatg   2460
aagcatcagg ctgtcattat ggtgtcctta cctgtgggag ctgtaaggtc ttctttaaga   2520
gggcaatgga agggcagcac aactacttat gtgctggaag aaatgactgc atcgttgata   2580
aaatccgcag aaaaaactgc ccagcatgtc gccttagaaa gtgctgtcag gctggcatgg   2640
tccttggagg tcgaaaattt aaaaagttca ataaagtcag agttgtgaga gcactggatg   2700
ctgttgctct cccacagcca gtgggcgttc caaatgaaag ccaagcccta agccagagat   2760
tcactttttc accaggtcaa gacatacagt tgattccacc actgatcaac ctgttaatga   2820
gcattgaacc agatgtgatc tatgcaggac atgacaacac aaaacctgac acctccagtt   2880
ctttgctgac aagtcttaat caactaggcg agaggcaact tctttcagta gtcaagtggt   2940
ctaaatcatt gccaggtttt cgaaacttac atattgatga ccagataact ctcattcagt   3000
attcttggat gagcttaatg gtgtttggtc taggatggag atcctacaaa cacgtcagtg   3060
ggcagatgct gtattttgca cctgatctaa tactaaatga acagcggatg aaagaatcat   3120
cattctattc attatgcctt accatgtggc agatcccaca ggagtttgtc aagcttcaag   3180
ttagccaaga agagttcctc tgtatgaaag tattgttact tcttaataca attcctttgg   3240
aagggctacg aagtcaaacc cagtttgagg agatgaggtc aagctacatt agagagctca   3300
tcaaggcaat tggtttgagg caaaaaggag ttgtgtcgag ctcacagcgt ttctatcaac   3360
ttacaaaact tcttgataac ttgcatgatc ttgtcaaaca acttcatctg tactgcttga   3420
atacatttat ccagtcccgg gcactgagtg ttgaatttcc agaaatgatg tctgaagtta   3480
ttgctgcaca attacccaag atattggcag ggatggtgaa acccctctc  tttcataaaa   3540
agtgaatgtc atctttttct tttaaagaat taaattttgt ggtatgtctt tttgttttgg   3600
tcaggattat gaggtcttga gtttttataa tgttcttctg aaagccttac atttataaca   3660
tcatagtgtg taaatttaaa agaaaaattg tgaggttcta attattttct tttataaagt   3720
ataattagaa tgtttaactg ttttgtttac ccatattttc ttgaagaatt tacaagattg   3780
aaaaagtact aaaattgtta aagtaaacta tcttatccat attatttcat accatgtagg   3840
tgaggatttt taacttttgc atctaacaaa tcatcgactt aagagaaaaa atcttacatg   3900
taataacaca aagctattat atgttatttc taggtaactc cctttgtgtc aattatattt   3960
ccaaaaatga acctttaaaa tggtatgcaa aattttgtct atatatattt gtgtgaggag   4020
gaaattcata actttcctca gattttcaaa agtattttta atgcaaaaaa tgtagaaaga   4080
gtttaaaacc actaaaatag attgatgttc ttcaaactag gcaaaacaac tcatatgtta   4140
```

```
agaccatttt ccagattgga aacacaaatc tcttaggaag ttaataagta gattcatatc   4200

attatgcaaa tagtattgtg ggttttgtag gtttttaaaa taaccttttt tggggagaga   4260

attgtcctct aatgaggtat tgcgagtgga cataagaaat cagaagatta tggcctaact   4320

gtactcctta ccaactgtgg catgctgaaa gttagtcact cttactgatt ctcaattctc   4380

tcacctttga aagtagtaaa atatctttcc tgccaattgc tcctttgggt cagagcttat   4440

taacatcttt tcaaatcaaa ggaaagaaga aagggagagg aggaggaggg aggtatcaat   4500

tcacatacct ttctcctctt tatcctccac tatcatgaat tcatattatg tttcagccat   4560

gcaaatcttt ttaccatgaa atttcttcca gaattttccc cctttgacac aaattccatg   4620

catgtttcaa ccttcgagac tcagccaaat gtcatttctg taaaatcttc cctgagtctt   4680

ccaagcagta atttgccttc tcctagagtt tacctgccat tttgtgcaca tttgagttac   4740

agtagcatgt tattttacaa ttgtgactct cctgggagtc tgggagccat ataaagtggt   4800

caatagtgtt tgctgactga gagttgaatg acattttctc tctgtcttgg tattactgta   4860

gatttcgatc attctttggt tacatttctg catatttctg tacccatgac tttatcactt   4920

tcttctccca tgctttatct ccatcaatta tcttcattac ttttaaattt tccacctttg   4980

cttcctactt tgtgagatct ctccctttac tgactataac atagaagaat agaagtgtat   5040

tttatgtgtc ttaaggacaa tactttagat tccttgttct aagtttttaa actgaatgaa   5100

tggaatatta tttctctccc taagcaaaat tccacaaaac aattatttct tatgtttatg   5160

tagccttaaa ttgttttgta ctgtaaacct cagcataaaa actttcttca tttctaattt   5220

cattcaacaa atattgattg aatacctggt attagcacaa gaaaaatgtg ctaataagcc   5280

ttatgagaat ttggagctga agaaagacat ataactcagg aaagttacag tccagtagta   5340

ggtataaatt acagtgcctg ataaataggc attttaatat ttgtacactc aacgtatact   5400

aggtaggtgc aaaacattta catataattt tactgatacc catgcagcac aaaggtacta   5460

actttaaata ttaaataaca cctttatgtg tcagtaattc atttgcatta aatcttattg   5520

aaaaggcttt caatatattt tccccacaaa tgtcatccca agaaaaaagt atttttaaca   5580

tctcccaaat ataatagtta caggaaatct acctctgtga gagtgacacc tctcagaatg   5640

aactgtgtga cacaagaaaa tgaatgtagg tctatccaaa aaaaacccca agaaacaaaa   5700

acaatattat tagcccttta tgcttaagtg atggactcag ggaacagttg atgttgtgat   5760

cattttatta tctgattctt gttactttga attaaaccaa tattttgatg atataaatca   5820

tttccaccag catatattta atttccataa taactttaaa attttctaat ttcactcaac   5880

tatgagggaa tagaatgtgg tggccacagg tttggctttt gttaaaatgt ttgatatctt   5940

cgatgttgat ctctgtctgc aatgtagatg tctaaacact aggatttaat atttaaggct   6000

aagctttaaa aataaagtac ctttttaaaa agaatatggc ttcaccaaat ggaaaatacc   6060

taatttctaa atctttttct ctacaaagtc ctatctacta atgtctccat tactatttag   6120

tcatcataac cattatcttc attttacatg tcgtgttctt tctggtagct ctaaaatgac   6180

actaaatcat aagaagacag gttacatatc aggaaatact tgaaggttac tgaaatagat   6240

tcttgagtta atgaaaatat tttctgtaaa aaggtttgaa aagccatttg agtctaaagc   6300

attatacctc cattatcagt agttatgtga caattgtgtg tgtgtttaat gtttaaagat   6360

gtggcacttt ttaataaggc aatgctatgc tattttttcc catttaacat taagataatt   6420

tattgctata cagatgatat ggaaatatga tgaacaatat ttttttgcc aaaactatgc   6480
```

-continued

```
cttgtaagta gccatggaat gtcaacctgt aacttaaatt atccacagat agtcatgtgt   6540
ttgatgatgg gcactgtgga gataactgac ataggactgt gcccccccttc tctgccactt   6600
actagctgga tgagattaag caagtcattt aactgctctg attaaacctg cctttcccaa   6660
gtgctttgta atgaatagaa atggaaacca aaaaaaacgt atacaggcct tcagaaatag   6720
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca ttttaaaata atgacactga ttttaacatt   7020
tttaagtgtc tttttagaac agagagcctg actagaacac agcccctcca aaaacccatg   7080
ctcaaattat ttttactatg gcagcaattc cacaaaaggg aacaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260
catttttagt ttttgctgtg aatacctgag cagtttctct catccatact tatccttcac   7320
acatcagaag tcaggataga atatgaatca ttttaaaaac ttttacaact ccagagccat   7380
gtgcataaga agcattcaaa acttgccaaa acatacattt tttttcaaat ttaaagatac   7440
tctatttttg tattcaatag ctcaacaact gtggtcccca ctgataaagt gaagtggaca   7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaattta agaatttggg ggtgttggta   8160
gtaagttaaa cacagcagct gttcatggca gaaattattc aatacatacc ttctctgaat   8220
atcctataac caaagcaaag aaaaacacca aggggtttgt tctcctcctt ggagttgacc   8280
tcattccaag gcagagctca ggtcacaggc acaggggctg cgcccaagct tgtccgcagc   8340
cttatgcagc tgtggagtct ggaagactgt tgcaggactg ctggcctagt cccagaatgt   8400
cagcctcatt ttcgatttac tggctcttgt tgctgtatgt catgctgacc ttattgttaa   8460
acacaggttt gtttgctttt tttccactca tggagacatg ggagaggcat tatttttaag   8520
ctggttgaaa gctttaaccg ataaagcatt tttagagaaa tgtgaatcag gcagctaaga   8580
aagcatactc tgtccattac ggtaaagaaa atgcacagat tattaactct gcagtgtggc   8640
attagtgtcc tggtcaatat tcggatagat atgaataaaa tatttaaatg gtattgtaaa   8700
tagttttcag gacatatgct atagcttatt tttattatct tttgaaattg ctcttaatac   8760
atcaaatcct gatgtattca atttatcaga tataaattat tctaaatgaa gcccagttaa   8820
atgtttttgt cttgtcagtt atatgttaag tttctgatct ctttgtctat gacgtttact   8880
```

-continued aatctgcatt tttactgtta tgaattattt tagacagcag tggtttcaag ctttttgcca 8940
ctaaaaatac cttttatttt ctcctccccc agaaaagtct ataccttgaa gtatctatcc 9000
accaaactgt acttctatta agaaatagtt attgtgtttt cttaatgttt tgttattcaa 9060
agacatatca atgaaagctg ctgagcagca tgaataacaa ttatatccac acagatttga 9120
tatattttgt gcagccttaa cttgatagta taaaatgtca ttgcttttta aataatagtt 9180
agtcaatgga cttctatcat agctttccta aactaggtta agatccagag ctttggggtc 9240
ataatatatt acatacaatt aagttatctt tttctaaggg ctttaaaatt catgagaata 9300
accaaaaaag gtatgtggag agttaataca aacataccat attcttgttg aaacagagat 9360
gtggctctgc ttgttctcca taaggtagaa atactttcca gaatttgcct aaactagtaa 9420
gccctgaatt tgctatgatt agggatagga agagattttc acatggcaga ctttagaatt 9480
cttcacttta gccagtaaag tatctccttt tgatcttagt attctgtgta ttttaacttt 9540
tctgagttgt gcatgtttat aagaaaaatc agcacaaagg gtttaagtta aagccttttt 9600
actgaaattt gaaagaaaca gaagaaaata tcaaagttct ttgtattttg agaggattaa 9660
atatgattta caaaagttac atggagggct ctctaaaaca ttaaattaat tattttttgt 9720
tgaaaagtct tactttaggc atcattttat tcctcagcaa ctagctgtga agcctttact 9780
gtgctgtatg ccagtcactc tgctagattg tggagattac cagtgttccc gtcttctccg 9840
agcttagagt tggatgggga ataaagacag gtaaacagat agctacaata ttgtactgtg 9900
aatgcttatg ctggaggaag tacagggaac tattggagca cctaagagga gcacctacct 9960
tgaatttagg ggttagcaga ggcatcctga aaaaagtcaa agctaagcca caatctataa 10020
gcagtttagg aattagcaga acgtgcgtgg tgaggagatg ccaaaggcaa gaagagaaga 10080
gtattccaaa caggagggat tccaaagaga gaagagtatc ccaaacaaca tttgcacaaa 10140
cctgatgggg agagagaatg tggggtgggg atggatgatg agactgaaga agaaagccag 10200
gtctagataa tcagtggcct tgtacaccat gttaaagagt gtagacttga ttctgttgta 10260
aacaggaaag cagcacaatt catatgaata ttttagaaga ctcccactgg aatatggaga 10320
ataaagttgg agatgactaa tcctggaagc agggagaaca tttttgagga agttgcacta 10380
ttttggtgaa aatgatgatc ataaacatga agaattgtag gtgatcatga cctcctctct 10440
aattttccag aagggttttg gaagatataa cataggaaca ttgacaggac tgacgaaagg 10500
agatgaaata caccatataa attgtcaaac acaaggccag atgtctaatt attttgctta 10560
tgtgttgaaa ttacaaattt ttcatcagga aaccaaaaac tacaaaactt agtttcccca 10620
agtcccagaa ttctatctgt ccaaacaatc tgtaccactc cacctatatc cctacctttg 10680
catgtctgtc caacctcaaa gtccaggtct atacacacgg gtaagactag agcagttcaa 10740
gtttcagaaa atgagaaaga ggaactgagt tgtgctgaac ccatacaaaa taaacacatt 10800
ctttgtatag attcttggaa cctcgagagg aattcaccta actcataggt atttgatggt 10860
atgaatccat ggctgggctc ggcttttaaa aagccttatc tgggattcct tctatggaac 10920
caagttccat caaagcccat ttaaaagcct acattaaaaa caaaattctt gctgcattgt 10980
atacaaataa tgatgtcatg atcaaataat cagatgccat tatcaagtgg aattacaaaa 11040
tggtataccc actccaaaaa aaaaaaaaaa gctaaattct cagtagaaca ttgtgacttc 11100
atgagccctc cacagccttg gagctgagga gggagcactg gtgagcagta ggttgaagag 11160
aaaacttggc gcttaataat ctatccatgt tttttcatct aaaagagcct tctttttgga 11220

-continued

```
ttaccttatt caatttccat caaggaaatt gttagttcca ctaaccagac agcagctggg  11280

aaggcagaag cttactgtat gtacatggta gctgtgggaa ggaggtttct ttctccaggt  11340

cctcactggc catacaccag tcccttgtta gttatgcctg gtcatagacc cccgttgcta  11400

tcatctcata tttaagtctt tggcttgtga atttatctat tctttcagct tcagcactgc  11460

agagtgctgg gactttgcta acttccattt cttgctggct tagcacattc ctcataggcc  11520

cagctctttt ctcatctggc cctgctgtgg agtcaccttg ccccttcagg agagccatgg  11580

cttaccactg cctgctaagc ctccactcag ctgccaccac actaaatcca agcttctcta  11640

agatgttgca gactttacag gcaagcataa aaggcttgat cttcctggac ttccctttac  11700

ttgtctgaat ctcacctcct tcaactttca gtctcagaat gtaggcattt gtcctctttg  11760

ccctacatct tccttcttct gaatcatgaa agcctctcac ttcctcttgc tatgtgctgg  11820

aggcttctgt caggttttag aatgagttct catctagtcc tagtagcttt tgatgcttaa  11880

gtccaccttt taaggatacc tttgagattt agaccatgtt tttcgcttga gaaagcccta  11940

atctccagac ttgcctttct gtggatttca aagaccaact gaggaagtca aaagctgaat  12000

gttgactttc tttgaacatt tccgctataa caattccaat tctcctcaga gcaatatgcc  12060

tgcctccaac tgaccaggag aaaggtccag tgccaaagag aaaaacacaa agattaatta  12120

tttcagttga gcacatactt tcaaagtggt ttgggtattc atatgaggtt ttctgtcaag  12180

agggtgagac tcttcatcta tccatgtgtg cctgacagtt ctcctggcac tggctggtaa  12240

cagatgcaaa actgtaaaaa ttaagtgatc atgtatttta acgatatcat cacatactta  12300

ttttctatgt aatgttttaa atttccccta acatactttg actgttttgc acatggtaga  12360

tattcacatt tttttgtgtt gaagttgatg caatcttcaa agttatctac cccgttgctt  12420

attagtaaaa ctagtgttaa tacttggcaa gagatgcagg gaatctttct catgactcac  12480

gccctattta gttattaatg ctactaccct attttgagta agtagtaggt ccctaagtac  12540

attgtccaga gttatacttt taaagatatt tagccccata tacttcttga atctaaagtc  12600

atacaccttg ctcctcattt ctgagtggga aagacatttg agagtatgtt gacaattgtt  12660

ctgaaggttt ttgccaagaa ggtgaaactg tcctttcatc tgtgtatgcc tggggctggg  12720

tccctggcag tgatggggtg acaatgcaaa gctgtaaaaa ctaggtgcta gtgggcacct  12780

aatatcatca tcatatactt attttcaagc taatatgcaa aatcccatct ctgtttttaa  12840

actaagtgta gatttcagag aaaatatttt gtggttcaca taagaaaaca gtctactcag  12900

cttgacaagt gttttatgtt aaattggctg gtggtttgaa atgaatcatc ttcacataat  12960

gttttcttta aaaatattgt gaatttaact ctaattcttg ttattctgtg tgataataaa  13020

gaataaacta atttcta                                                 13037
```

<210> SEQ ID NO 4
<211> LENGTH: 4314
<212> TYPE: DNA
<213> ORGANISM: Homo sapiens
<223> OTHER INFORMATION: AR- Androgen receptor (NM_000044+2)

<400> SEQUENCE: 4

```
cgagatcccg gggagccagc ttgctgggag agcgggacgg tccggagcaa gcccagaggc     60

agaggaggcg acagagggaa aaagggccga gctagccgct ccagtgctgt acaggagccg    120

aagggacgca ccacgccagc cccagcccgg ctccagcgac agccaacgcc tcttgcagcg    180

cggcggcttc gaagccgccg cccggagctg ccctttcctc ttcggtgaag tttttaaaag    240
```

-continued

```
ctgctaaaga ctcggaggaa gcaaggaaag tgcctggtag gactgacggc tgcctttgtc    300
ctcctcctct ccaccccgcc tccccccacc ctgccttccc cccctccccc gtcttctctc    360
ccgcagctgc ctcagtcggc tactctcagc caacccccct caccaccctt ctccccaccc    420
gccccccgc ccccgtcggc ccagcgctgc cagcccgagt ttgcagagag gtaactccct    480
ttggctgcga gcgggcgagc tagctgcaca ttgcaaagaa ggctcttagg agccaggcga    540
ctggggagcg gcttcagcac tgcagccacg acccgcctgg ttaggctgca cgcggagaga    600
accctctgtt ttcccccact ctctctccac ctcctcctgc cttccccacc ccgagtgcgg    660
agccagagat caaaagatga aaaggcagtc aggtcttcag tagccaaaaa acaaaacaaa    720
caaaaacaaa aaagccgaaa taaaagaaaa agataataac tcagttctta tttgcaccta    780
cttcagtgga cactgaattt ggaaggtgga ggattttgtt tttttctttt aagatctggg    840
catcttttga atctaccctt caagtattaa gagacagact gtgagcctag cagggcagat    900
cttgtccacc gtgtgtcttc ttctgcacga gactttgagg ctgtcagagc gctttttgcg    960
tggttgctcc cgcaagtttc cttctctgga gcttcccgca ggtgggcagc tagctgcagc   1020
gactaccgca tcatcacagc ctgttgaact cttctgagca agagaagggg aggcggggta   1080
agggaagtag gtggaagatt cagccaagct caaggatgga agtgcagtta gggctgggaa   1140
gggtctaccc tcggccgccg tccaagacct accgaggagc tttccagaat ctgttccaga   1200
gcgtgcgcga agtgatccag aacccgggcc ccaggcaccc agaggccgcg agcgcagcac   1260
ctcccggcgc cagtttgctg ctgctgcagc agcagcagca gcagcagcag cagcagcagc   1320
agcagcagca gcagcagcag cagcagcagc agcaagagac tagccccagg cagcagcagc   1380
agcagcaggg tgaggatggt tctccccaag cccatcgtag aggccccaca ggctacctgg   1440
tcctggatga ggaacagcaa ccttcacagc cgcagtcggc cctggagtgc caccccgaga   1500
gaggttgcgt cccagagcct ggagccgccg tggccgccag caaggggctg ccgcagcagc   1560
tgccagcacc tccggacgag gatgactcag ctgccccatc cacgttgtcc ctgctgggcc   1620
ccactttccc cggcttaagc agctgctccg ctgaccttaa agacatcctg agcgaggcca   1680
gcaccatgca actccttcag caacagcagc aggaagcagt atccgaaggc agcagcagcg   1740
ggagagcgag ggaggcctcg ggggctccca cttcctccaa ggacaattac ttagggggca   1800
cttcgaccat ttctgacaac gccaaggagt tgtgtaaggc agtgtcggtg tccatgggcc   1860
tgggtgtgga ggcgttggag catctgagtc caggggaaca gcttcggggg gattgcatgt   1920
acgccccact tttgggagtt ccacccgctg tgcgtcccac tccttgtgcc ccattggccg   1980
aatgcaaagg ttctctgcta gacgacagcg caggcaagag cactgaagat actgctgagt   2040
attccccttt caagggaggt tacaccaaag ggctagaagg cgagagccta ggctgctctg   2100
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg ccccctccgc cgcctcccca tccccacgct cgcatcaagc   2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtgggggt ggtggcggcg gcggcggcgg cggcggcggc ggcggcggcg   2520
gcggcggcgg cggcgaggcg ggagctgtag ccccctacgg ctacactcgg ccccctcagg   2580
ggctggcggg ccaggaaagc gacttcaccg cacctgatgt gtggtaccct ggcggcatgg   2640
```

tgagcagagt gccctatccc agtcccactt gtgtcaaaag cgaaatgggc ccctggatgg 2700
atagctactc cggaccttac ggggacatgc gtttggagac tgccagggac catgttttgc 2760
ccattgacta ttactttcca ccccagaaga cctgcctgat ctgtggagat gaagcttctg 2820
ggtgtcacta tggagctctc acatgtggaa gctgcaaggt cttcttcaaa agagccgctg 2880
aagggaaaca gaagtacctg tgcgccagca gaaatgattg cactattgat aaattccgaa 2940
ggaaaaattg tccatcttgt cgtcttcgga aatgttatga agcagggatg actctgggag 3000
cccggaagct gaagaaactt ggtaatctga aactacagga ggaaggagag gcttccagca 3060
ccaccagccc cactgaggag acaacccaga agctgacagt gtcacacatt gaaggctatg 3120
aatgtcagcc catctttctg aatgtcctgg aagccattga gccaggtgta gtgtgtgctg 3180
gacacgacaa caaccagccc gactcctttg cagccttgct ctctagcctc aatgaactgg 3240
gagagagaca gcttgtacac gtggtcaagt gggccaaggc cttgcctggc ttccgcaact 3300
tacacgtgga cgaccagatg gctgtcattc agtactcctg gatggggctc atggtgtttg 3360
ccatgggctg gcgatccttc accaatgtca actccaggat gctctacttc gcccctgatc 3420
tggttttcaa tgagtaccgc atgcacaagt cccggatgta cagccagtgt gtccgaatga 3480
ggcacctctc tcaagagttt ggatggctcc aaatcacccc ccaggaattc ctgtgcatga 3540
aagcactgct actcttcagc attattccag tggatgggct gaaaaatcaa aaattctttg 3600
atgaacttcg aatgaactac atcaaggaac tcgatcgtat cattgcatgc aaaagaaaaa 3660
atcccacatc ctgctcaaga cgcttctacc agctcaccaa gctcctggac tccgtgcagc 3720
ctattgcgag agagctgcat cagttcactt ttgacctgct aatcaagtca cacatggtga 3780
gcgtggactt tccggaaatg atggcagaga tcatctctgt gcaagtgccc aagatccttt 3840
ctgggaaagt caagcccatc tatttccaca cccagtgaag cattggaaac cctatttccc 3900
caccccagct catgccccct ttcagatgtc ttctgcctgt tataactctg cactactcct 3960
ctgcagtgcc ttggggaatt tcctctattg atgtacagtc tgtcatgaac atgttcctga 4020
attctatttg ctgggctttt tttttctctt tctctccttt ctttttcttc ttccctccct 4080
atctaaccct cccatggcac cttcagactt tgcttcccat tgtggctcct atctgtgttt 4140
tgaatggtgt tgtatgcctt taaatctgtg atgatcctca tatggcccag tgtcaagttg 4200
tgcttgttta cagcactact ctgtgccagc cacacaaacg tttacttatc ttatgccacg 4260
ggaagtttag agagctaaga ttatctgggg aaatcaaaac aaaaacaagc aaac 4314

<210> SEQ ID NO 5
<211> LENGTH: 1765
<212> TYPE: DNA
<213> ORGANISM: Homo sapiens
<223> OTHER INFORMATION: AR - Androgen receptor (NM_001011645+1)

<400> SEQUENCE: 5
gctgcgagca gagagggatt cctcggaggt catctgttcc atcttcttgc ctatgcaaat 60
gcctgcctga agctgctgga ggctggcttt gtaccggact ttgtacaggg aaccagggaa 120
acgaatgcag agtgctcctg acattgcctg tcactttttc ccatgatact ctggcttcac 180
agtttggaga ctgccaggga ccatgttttg cccattgact attactttcc accccagaag 240
acctgcctga tctgtggaga tgaagcttct gggtgtcact atggagctct cacatgtgga 300
agctgcaagg tcttcttcaa aagagccgct gaagggaaac agaagtacct gtgcgccagc 360
agaaatgatt gcactattga taaattccga aggaaaaatt gtccatcttg tcgtcttcgg 420
aaatgttatg aagcagggat gactctggga gcccggaagc tgaagaaact tggtaatctg 480
aaactacagg aggaaggaga ggcttccagc accaccagcc ccactgagga gacaacccag 540
aagctgacag tgtcacacat tgaaggctat gaatgtcagc ccatctttct gaatgtcctg 600
gaagccattg agccaggtgt agtgtgtgct ggacacgaca acaaccagcc cgactccttt 660
gcagccttgc tctctagcct caatgaactg ggagagagac agcttgtaca cgtggtcaag 720
tgggccaagg ccttgcctgg cttccgcaac ttacacgtgg acgaccagat ggctgtcatt 780
cagtactcct ggatggggct catggtgttt gccatgggct ggcgatcctt caccaatgtc 840
aactccagga tgctctactt cgcccctgat ctggttttca atgagtaccg catgcacaag 900
tcccggatgt acagccagtg tgtccgaatg aggcacctct ctcaagagtt tggatggctc 960
caaatcaccc cccaggaatt cctgtgcatg aaagcactgc tactcttcag cattattcca 1020
gtggatgggc tgaaaaatca aaaattcttt gatgaacttc gaatgaacta catcaaggaa 1080
ctcgatcgta tcattgcatg caaaagaaaa aatcccacat cctgctcaag acgcttctac 1140
cagctcacca agctcctgga ctccgtgcag cctattgcga gagagctgca tcagttcact 1200
tttgacctgc taatcaagtc acacatggtg agcgtggact ttccggaaat gatggcagag 1260
atcatctctg tgcaagtgcc caagatcctt tctgggaaag tcaagcccat ctatttccac 1320
acccagtgaa gcattggaaa ccctatttcc ccaccccagc tcatgccccc tttcagatgt 1380
cttctgcctg ttataactct gcactactcc tctgcagtgc cttggggaat ttcctctatt 1440
gatgtacagt ctgtcatgaa catgttcctg aattctattt gctgggcttt ttttttctct 1500
ttctctcctt tctttttctt cttccctccc tatctaaccc tcccatggca ccttcagact 1560
ttgcttccca ttgtggctcc tatctgtgtt ttgaatggtg ttgtatgcct ttaaatctgt 1620
gatgatcctc atatggccca gtgtcaagtt gtgcttgttt acagcactac tctgtgccag 1680
ccacacaaac gtttacttat cttatgccac gggaagttta gagagctaag attatctggg 1740
gaaatcaaaa caaaaacaag caaac 1765

<210> SEQ ID NO 6
<211> LENGTH: 4422
<212> TYPE: DNA
<213> ORGANISM: Homo sapiens
<223> OTHER INFORMATION: CYP19 (Aromatase)

<400> SEQUENCE: 6
gggagtttct ggagggctga acacgtggag gcaaacagga aggtgaagaa gaacttatcc 60
tatcaggacg gaaggtcctg tgctcgggat cttccagacg tcgcgactct aaattgcccc 120
ctctgaggtc aaggaacaca agatggtttt ggaaatgctg aacccgatac attataacat 180
caccagcatc gtgcctgaag ccatgcctgc tgccaccatg ccagtcctgc tcctcactgg 240
cctttttctc ttggtgtgga attatgaggg cacatcctca ataccaggtc ctggctactg 300
catgggaatt ggacccctca tctcccacgg cagattcctg tggatgggga tcggcagtgc 360
ctgcaactac tacaaccggg tatatggaga attcatgcga gtctggatct ctggagagga 420
aacactcatt atcagcaagt cctcaagtat gttccacata atgaagcaca atcattacag 480
ctctcgattc ggcagcaaac ttgggctgca gtgcatcggt atgcatgaga aaggcatcat 540
atttaacaac aatccagagc tctggaaaac aactcgaccc ttctttatga aagctctgtc 600
aggccccggc cttgttcgta tggtcacagt ctgtgctgaa tccctcaaaa cacatctgga 660
caggttggag gaggtgacca atgaatcggg ctatgtggac gtgttgaccc ttctgcgtcg 720

-continued

```
tgtcatgctg gacacctcta acacgctctt cttgaggatc cctttggacg aaagtgctat    780
cgtggttaaa atccaaggtt attttgatgc atggcaagct ctcctcatca aaccagacat    840
cttctttaag atttcttggc tatacaaaaa gtatgagaag tctgtcaagg atttgaaaga    900
tgccatagaa gttctgatag cagaaaaaag acgcaggatt tccacagaag agaaactgga    960
agaatgtatg gactttgcca ctgagttgat tttagcagag aaacgtggtg acctgacaag   1020
agagaatgtg aaccagtgca tattggaaat gctgatcgca gctcctgaca ccatgtctgt   1080
ctctttgttc ttcatgctat ttctcattgc aaagcaccct aatgttgaag aggcaataat   1140
aaaggaaatc cagactgtta ttggtgagag agacataaag attgatgata tacaaaaatt   1200
aaaagtgatg gaaaacttca tttatgagag catgcggtac cagcctgtcg tggacttggt   1260
catgcgcaaa gccttagaag atgatgtaat cgatggctac ccagtgaaaa aggggacaaa   1320
cattatcctg aatattggaa ggatgcacag actcgagttt ttccccaaac ccaatgaatt   1380
tactcttgaa aattttgcaa agaatgttcc ttataggtac tttcagccat ttggctttgg   1440
gccccgtggc tgtgcaggaa agtacatcgc catggtgatg atgaaagcca tcctcgttac   1500
acttctgaga cgattccacg tgaagacatt gcaaggacag tgtgttgaga gcatacagaa   1560
gatacacgac ttgtccttgc acccagatga gactaaaaac atgctggaaa tgatctttac   1620
cccaagaaac tcagacaggt gtctggaaca ctagagaagg ctggtcagta cccactctgg   1680
agcatttctc atcagtagtt cacatacaaa tcatccatcc ttgccaatag tgtcatcctc   1740
acagtgaaca ctcagtggcc catggcattt tataggcata cctcctatgg gttgtcacca   1800
agctaggtgc tatttgtcat ctgctcctgt tcacaccaga gaaccaggct acaagagaaa   1860
aagcagaggc caagagtttg agggagaaat agtcggtgaa gaaaccgtat ccataaagac   1920
ccgattccac caaatgtgct ttgagaagga taggccttca ttaacaaaat gtatgtctgg   1980
ttccccagta gagctctact gcctcaaccc aaggggattt ttatgtctgg ggcagaaaca   2040
ctcaagttga ttagaaagac caggccaatg tcagggtacc tggggccaaa cccacctgct   2100
agtgtgaatt aaagtacttt aattttgttt tctgtggagg tggaaaagca acattcatag   2160
tctttggaga aatgcttaga aattcagcat ttgacccttg ctgtgaatta agcccaatta   2220
attcctgttt gtctacatat gatctgtctg tggcaaaagt ttaatcagag gaaattcttt   2280
cccagtctgt cgatttatgc ctcagccact tgcctgtgct acaattcatt gtgttacctg   2340
tagattcagg taatacaaac tatatataat catcaagtaa tacaaactaa tttagtaata   2400
gcctgggtta agtattatta gggccctgtg tctgctgtag aaaaaaaaat tcacatgatg   2460
cacttcaaat tcaaataaaa atccttttgg catgttccca tttttgctta gctcaattag   2520
tgtggctaac caagagataa ctgtaaatgt gacattgatt tgctcttact acagcttcag   2580
tgattggggg aggaaaagtc ccaacccaat gggctcaaac ttctaagggg tactcctctc   2640
atccccttat ccttctccct cgacattttc tccctctttc ttcccatgac cccaaagcca   2700
agggcaacag atcagtaaag aacgtggtca gagtagaacc cctgaagtat tttttaatcc   2760
tacctcaaaa tttaacagtt acctgagaga tttaacatta tctagttcat tgaatcattg   2820
tatgtggtca tggataaatt gcacaccttg gaattcgctt tctaaaggaa atcaaatgaa   2880
tggaggaact ttccaaacac cactttactt gtgttatata gccaatataa ctatctctac   2940
tgaatgtcat tgaaaaacta aaaaattaaa cttatttaca aataggtaaa tatttgtcat   3000
tgaatccatt gccatcccat ttgactgttc ttttcatcct actgtctagt aataagctga   3060
```

-continued

```
gtataagatg acagtgtaat ctccctgaaa gcaggagcta ctttctttct tttgtaatct   3120

atttccatcc ccatttccct gtcctgtctc cctgtattca ctcccaagct cagttctgaa   3180

tagacattcc tgctcagaga tactcccaac tgatgcagaa accaaataaa gaggtaggta   3240

ttccaagaat tcaagaatgg acattagtaa agaataaaac atttatttga gcttggaatt   3300

atttggatca tctatatggc ctaaaaatat atggactatg cctgtgtacc tgaatacgta   3360

tgtagtcagg tcaagacaat catccaaata acttagaccc ctaaaagcaa ggccaggatt   3420

tgcaatttaa tgtgtcccaa ttaattcact tgaaaattag taacactctg tttacgttgc   3480

ctctggctgg agctgcatgg tggaagaagc ccaactttgg atccatgtac ttcacccatc   3540

caatactctt gggacattta tgtgtatttt atctgtatat atgaagccaa tgtctatgtc   3600

tacacagtca aagtgaaatg catgtttgat atagctgtac atagatatct attttgcagg   3660

tacaaaaata tcctgggggga aaactgggag tggaagggtg gggggtggga gtgagggaca   3720

tgggggaggg acaggaagag gagaagtgtt ggtttgaacg atccaagcaa actctcccag   3780

aatcaaatta cctgggtagt tgttcaactt ttcactctgc ttagcctgta tagacaaacc   3840

ccatatattt gtagaggctt ggccttggaa ttctggaata ccattggctt ttcagtaggc   3900

tgatgaacac attttgaaaa ttctattatc ttcagaattt tgccccattg ttaagtgctt   3960

aaccgtcact cttgaatgtg caatgtgctg tggattccat tttcatcagt tctgaaagaa   4020

ctgcaatgtg taaattatca gtgaaatgca tgcatataag ggctctatca ttatcaaatt   4080

gtaaggacaa ttgtaccctt ctatatcttt gggcatgcta gacaccccca tgccttcatt   4140

gagatcccat tttccccctc tcaagtggaa aataatcaca tccagcaagc tctctcatta   4200

ttgagaaata ccatttggaa attgccactt tttattccta agcagcacct ttcactgttc   4260

atgatgctaa tgttccacaa aagcatgtgc cattggccca ctgaaggata gagggaccct   4320

tttcaatcta tatcagctgg gctctgggac tgaatctctc acctattctt gcagaaagac   4380

atactaatta aaccttgtca aagtaaaaaa aaaaaaaaaa aa                      4422
```

<210> SEQ ID NO 7
<211> LENGTH: 1708
<212> TYPE: DNA
<213> ORGANISM: Homo sapiens
<223> OTHER INFORMATION: SNAI1-Snail homolog 1

<400> SEQUENCE: 7

```
ggcacggcct agcgagtggt tcttctgcgc tactgctgcg cgaatcggcg accccagtgc     60

ctcgaccact atgccgcgct ctttcctcgt caggaagccc tccgacccca atcggaagcc    120

taactacagc gagctgcagg actctaatcc agagtttacc ttccagcagc cctacgacca    180

ggcccacctg ctggcagcca tcccacctcc ggagatcctc aaccccaccg cctcgctgcc    240

aatgctcatc tgggactctg tcctggcgcc ccaagcccag ccaattgcct gggcctccct    300

tcggctccag gagagtccca gggtggcaga gctgacctcc ctgtcagatg aggacagtgg    360

gaaaggctcc cagcccccca gcccaccctc accggctcct tcgtccttct cctctacttc    420

agtctcttcc ttggaggccg aggcctatgc tgccttccca ggcttgggcc aagtgcccaa    480

gcagctggcc cagctctctg aggccaagga tctccaggct cgaaaggcct tcaactgcaa    540

atactgcaac aaggaatacc tcagcctggg tgccctcaag atgcacatcc gaagccacac    600

gctgccctgc gtctgcggaa cctgcgggaa ggccttctct aggccctggc tgctacaagg    660

ccatgtccgg acccacactg gcgagaagcc cttctcctgt ccccactgca gccgtgcctt    720
```

-continued

```
cgctgaccgc tccaacctgc gggcccacct ccagacccac tcagatgtca agaagtacca    780

gtgccaggcg tgtgctcgga ccttctcccg aatgtccctg ctccacaagc accaagagtc    840

cggctgctca ggatgtcccc gctgaccctc gaggctccct cttcctctcc atacctgccc    900

ctgcctgaca gccttcccca gctccagcag gaaggacccc acatccttct cactgccatg    960

gaattccctc ctgagtgccc cacttctggc cacatcagcc ccacaggact ttgatgaaga   1020

ccattttctg gttctgtgtc ctctgcctgg gctctggaag aggccttccc atggccattt   1080

ctgtggaggg agggcagctg gcccccagcc ctgggggatt cctgagctgg cctgtctgcg   1140

tgggtttttg tatccagagc tgtttggata cagctgcttt gagctacagg acaaaggctg   1200

acagactcac tgggaagctc ccaccccact caggggaccc cactcccctc acacacaccc   1260

ccccacaagg aaccctcagg ccaccctcca cgaggtgtga ctaactatgc aataatccac   1320

ccccaggtgc agccccaggg cctgcggagg cggtggcaga ctagagtctg agatgccccg   1380

agcccaggca gctatttcag cctcctgttt ggtggggtgg cacctgtttc ccgggcaatt   1440

taacaatgtc tgaaaaggga ctgtgagtaa tggctgtcac ttgtcggggg cccaagtggg   1500

gtgctctggt ctgaccgatg tgtctcccag aactattctg gggcccgac aggtgggcct    1560

gggaggaaga tgtttacatt tttaaaggta cactggtatt tatatttcaa acattttgta   1620

tcaaggaaac gttttgtata gttatatgta cagtttattg atattcaata aagcagttaa   1680

tttatatatt aaaaaaaaaa aaaaaaaa                                      1708
```

<210> SEQ ID NO 8
<211> LENGTH: 2101
<212> TYPE: DNA
<213> ORGANISM: Homo sapiens
<223> OTHER INFORMATION: SNAI2 - SLUG; Snail homolog 2

<400> SEQUENCE: 8

```
agttcgtaaa ggagccgggt gacttcagag gcgccggccc gtccgtctgc cgcacctgag     60

cacggcccct gcccgagcct ggcccgccgc gatgctgtag ggaccgccgt gtcctcccgc    120

cggaccgtta tccgcgccgg gcgcccgcca gacccgctgg caagatgccg cgctccttcc    180

tggtcaagaa gcatttcaac gcctccaaaa agccaaacta cagcgaactg gacacacata    240

cagtgattat ttccccgtat ctctatgaga gttactccat gcctgtcata ccacaaccag    300

agatcctcag ctcaggagca tacagcccca tcactgtgtg gactaccgct gctccattcc    360

acgcccagct acccaatggc ctctctcctc tttccggata ctcctcatct ttggggcgag    420

tgagtccccc tcctccatct gacacctcct ccaaggacca cagtggctca gaaagcccca    480

ttagtgatga agaggaaaga ctacagtcca agctttcaga cccccatgcc attgaagctg    540

aaaagtttca gtgcaattta tgcaataaga cctattcaac tttttctggg ctggccaaac    600

ataagcagct gcactgcgat gcccagtcta gaaaatcttt cagctgtaaa tactgtgaca    660

aggaatatgt gagcctgggc gccctgaaga tgcatattcg gacccacaca ttaccttgtg    720

tttgcaagat ctgcggcaag gcgttttcca gaccctggtt gcttcaagga cacattagaa    780

ctcacacggg ggagaagcct tttcttgcc ctcactgcaa cagagcattt gcagacaggt     840

caaatctgag ggctcatctg cagacccatt ctgatgtaaa gaaataccag tgcaaaaact    900

gctccaaaac cttctccaga atgtctctcc tgcacaaaca tgaggaatct ggctgctgtg    960

tagcacactg agtgacgcaa tcaatgttta ctcgaacaga atgcatttct tcactccgaa   1020

gccaaatgac aaataaagtc caaaggcatt ttctcctgtg ctgaccaacc aaataatatg   1080
```

-continued tatagacaca cacacatatg cacacacaca cacacacacc cacagagaga gagctgcaag 1140
agcatggaat tcatgtgttt aaagataatc ctttccatgt gaagtttaaa attactatat 1200
atttgctgat ggctagattg agagaataaa agacagtaac ctttctcttc aaagataaaa 1260
tgaaaagcac attgcatctt ttcttcctaa aaaaatgcaa agatttacat tgctgccaaa 1320
tcatttcaac tgaaaagaac agtattgctt tgtaatagag tctgtaatag gatttcccat 1380
aggaagagat ctgccagacg cgaactcagg tgccttaaaa agtattccaa gtttactcca 1440
ttacatgtcg gttgtctggt tgccattgtt gaactaaagc cttttttga ttacctgtag 1500 tgctttaaag tatattttta aaagggagga aaaaaataac aagaacaaaa cacaggagaa 1560
tgtattaaaa gtatttttgt tttgttttgt ttttgccaat taacagtatg tgccttgggg 1620
gaggagggaa agattagctt tgaacattcc tggcgcatgc tccattgtct tactatttta 1680
aaacatttta ataattttg aaaattaatt aaagatggga ataagtgcaa aagaggattc 1740
ttacaaattc attaatgtac ttaaactatt tcaaatgcat accacaaatg caataataca 1800
ataccccttc caagtgcctt tttaaattgt atagttgatg agtcaatgta aatttgtgtt 1860
tatttttata tgattgaatg agttctgtat gaaactgaga tgttgtctat agctatgtct 1920
ataaacaacc tgaagacttg tgaaatcaat gtttcttttt taaaaaacaa ttttcaagtt 1980 tttttacaa taaacagttt tgatttaaaa tctcgtttgt atactatttt cagagacttt 2040
acttgcttca tgattagtac caaaccactg tacaaagaat tgtttgttaa caagaaaaaa 2100
a 2101

<210> SEQ ID NO 9
<211> LENGTH: 1713
<212> TYPE: DNA
<213> ORGANISM: Homo sapiens
<223> OTHER INFORMATION: SNAI3 SMUC; Snail homolog 3

<400> SEQUENCE: 9
cagcagtccg gacccaggcg cgcccctccc gccccagccc accccggcct gccgcccggg 60
aggggaacat gccgcgctcc ttcctggtga aaacgcactc cagccacagg gtccccaact 120
accggcggct ggagacgcag agagaaatca atggtgcctg ctctgcctgt ggggggctgg 180
tggtgcccct cctcccccga gacaaggagg ccccttctgt gcccggtgac cttccccagc 240
cctgggaccg ctcctcggcc gtcgcctgca tctccctgcc cctcctgcca cggatcgagg 300
aagctctggg ggcctctggg ctggacgcct tggaagtcag cgaggtcgac cctcgggcca 360
gccgggccgc cattgtaccc ctcaaagaca gcctgaacca cctcaacctg cccccactgc 420
tggtgctgcc cacacggtgg tccccgacct tgggcccaga ccggcacggg gctccggaaa 480
aactgcttgg ggctgagcgg atgccccgag ccccgggcgg ctttgagtgc ttccactgcc 540
acaaacccta ccacacgctg gccgggctgg ccaggcaccg gcagctgcac tgccacctgc 600
aggtggggcg tgtcttcacc tgcaagtact gcgacaagga gtacaccagc ctgggtgccc 660
tcaagatgca catccgcact cacacgctgc cctgcacctg caagatctgt ggcaaggcct 720
tctccaggcc ctggttactg cagggccatg tccgcaccca cacaggggag aagccctatg 780
cctgctcgca ctgcagcagg gcctttgccg accgctccaa ccttcgggcc catctgcaaa 840
cgcactcaga cgccaagaag taccggtgcc ggcgctgcac caagaccttc tcccgcatgt 900
ccctcctggc gcggcatgag gagtctggct gctgcccggg cccctgagag gcacgtggtc 960
ggcgcaggta ggagggatgg tcctcaccgg gagagctggc gtccctcctg cccccagagg 1020

-continued

```
agccaggagt ctgggagggc ggggcctggc ctcacacttg gtgcgtcctc cacatctgcg   1080

tccaatcaga accaaagaag tccagcgggg gccactgggc cggaggacac tcccccaggc   1140

atcccaccgc gcggagccca ctcagaggag actcctctcc cggggaaggc tttcatcaga   1200

acaagagcca tggttccatt tcgacacggc caggtctccg gggctaccct tccaagagtc   1260

agagcctcgg ggaggtggcc gccagcatgg gccggcactg ccgccggatg gctggcaagg   1320

ctgcctagtt ccattgcagc agaaatgaac agttctgact tatagtgagc accgccctgt   1380

ggcccttcct cagtaggcac aactacctct cagccagccc ccgccagcct ttggtttggg   1440

gtctgggacg agctgcccca tgtcacacgt ctatgtgcat gtgcacacac actcaaacat   1500

gtacacacac gtgccctccc cacctcacta gactctccgg gagatggggc aggactggga   1560

gagcccacga ttggtgattt gggtgtgttg ggatgaggcg gagtgcctgt gggatttgtc   1620

ccggtcagag cctcaggggg ctggggtctc agggcactca gcttcccagg caataacagc   1680

cgtggggtaa taaatggtct ctgcacacct gca                                1713
```